US010538585B2

(12) United States Patent
Dengl et al.

(10) Patent No.: US 10,538,585 B2
(45) Date of Patent: *Jan. 21, 2020

(54) ANTI-ANG2 ANTIBODIES AND METHODS OF USE

(71) Applicant: Hoffmann-La Roche Inc., Little Falls, NJ (US)

(72) Inventors: Stefan Dengl, Munich (DE); Guy Georges, Habach (DE); Peter Michael Huelsmann, Habach (DE); Hubert Kettenberger, Munich (DE); Joerg Moelleken, Munich (DE); Michael Molhoj, Munich (DE); Joerg Thomas Regula, Munich (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/591,600

(22) Filed: May 10, 2017

(65) Prior Publication Data

US 2017/0247441 A1  Aug. 31, 2017

Related U.S. Application Data

(63) Continuation of application No. PCT/EP2015/075876, filed on Nov. 6, 2015.

(30) Foreign Application Priority Data

Nov. 10, 2014 (EP) .................................... 14192524

(51) Int. Cl.
*C07K 16/22* (2006.01)
*A61K 39/395* (2006.01)
*A61K 39/00* (2006.01)

(52) U.S. Cl.
CPC .......... *C07K 16/22* (2013.01); *A61K 39/3955* (2013.01); *A61K 2039/507* (2013.01); *C07K 2317/31* (2013.01); *C07K 2317/33* (2013.01); *C07K 2317/55* (2013.01); *C07K 2317/56* (2013.01); *C07K 2317/565* (2013.01); *C07K 2317/76* (2013.01); *C07K 2317/92* (2013.01)

(58) Field of Classification Search
CPC .............. C07K 16/22; C07K 2317/565; A61K 2039/507
USPC .................................... 424/133.1, 136, 178.1
See application file for complete search history.

(56) References Cited

U.S. PATENT DOCUMENTS

| | | | |
|---|---|---|---|
| 4,935,343 A | 6/1990 | Allison et al. | |
| 7,993,878 B2 | 8/2011 | Gram et al. | |
| 8,268,314 B2 * | 9/2012 | Baehner | C07K 16/22 424/136.1 |
| 8,703,130 B2 * | 4/2014 | Baehner | C07K 16/22 424/130.1 |
| 9,151,761 B2 * | 10/2015 | Anderson | A61K 31/17 |
| 9,695,233 B2 * | 7/2017 | Duerr | C07K 16/22 |
| 9,708,396 B2 * | 7/2017 | Baehner | C07K 16/22 |
| 2010/0111967 A1 * | 5/2010 | Baehner | C07K 16/22 424/158.1 |
| 2012/0321627 A1 * | 12/2012 | Baehner | C07K 16/22 424/136.1 |
| 2013/0142783 A1 | 6/2013 | Coyle et al. | |
| 2013/0330355 A1 | 12/2013 | Ke et al. | |
| 2014/0093498 A1 * | 4/2014 | Gschwind | A61K 31/404 424/133.1 |
| 2014/0093499 A1 * | 4/2014 | Gschwind | A61K 31/496 424/133.1 |
| 2014/0348824 A1 * | 11/2014 | Anderson | A61K 31/17 424/134.1 |
| 2015/0004166 A1 * | 1/2015 | Baehner | C07K 16/22 424/136.1 |
| 2015/0232548 A1 * | 8/2015 | Klein | C07K 16/22 424/136.1 |
| 2017/0240629 A1 * | 8/2017 | Bedoucha | C07K 16/22 |
| 2017/0247440 A1 | 8/2017 | Bedoucha et al. | |
| 2017/0247447 A1 | 8/2017 | Dengl et al. | |
| 2017/0369566 A1 * | 12/2017 | Baehner | C07K 16/22 |
| 2018/0134780 A1 * | 5/2018 | Klein | C07K 16/22 |
| 2018/0346559 A1 * | 12/2018 | Hilberg | C07K 16/3023 |
| 2019/0004048 A1 * | 1/2019 | Anderson | G01N 33/57438 |

FOREIGN PATENT DOCUMENTS

| | | | |
|---|---|---|---|
| RU | 2368359 | | 9/2009 |
| WO | 2003/073982 | | 9/2003 |
| WO | WO 2004/003019 | * | 6/2004 |
| WO | 2004/067568 A2 | | 8/2004 |
| WO | 2005/087812 A1 | | 9/2005 |
| WO | 2008/024188 A | | 2/2008 |
| WO | 2009/080252 A1 | | 7/2009 |
| WO | 2009/149370 | | 12/2009 |
| WO | 2010/040508 A1 | | 4/2010 |

(Continued)

OTHER PUBLICATIONS

Ward et al. (Nature 341:544-546 (1989)).*
Bogdanovic et al. (J. Cell Sci 119 (17): 3551-3560 (2006)).*
Hansen et al. (Cell Signal 22(3):527-532 (Mar. 2010).*
Fenn et al. (PLoS One. Apr. 17, 2013;8(4):e61953).*
Scheuer et al. (MAbs. Apr. 2016; 8(3): 562-573).*
Gassner et al., (J Pharm Biomed Anal. Jan. 2015;102:144-9).*
Regula et al. (EMBO Mol Med. Nov. 2, 2016;8(11):1265-1288).*
Klein et al. (MAbs. Aug.-Sep. 2016;8(6):1010-20).*
Kienast et al. (Clin Cancer Res; 19(24); 6730-40 (Dec. 2013)).*
Stubenrauch et al. (J Pharm Biomed Anal. Jan. 2015;102:459-67).*
Bessho et al. (Cancer Invest. 2015;33(8):378-86).*
Kloepper et al., ( Proc Natl Acad Sci U S A. Apr. 19, 2016;113(16):4476-81).*

(Continued)

*Primary Examiner* — Lynn A Bristol
(74) *Attorney, Agent, or Firm* — Grant Kalinowski

(57) ABSTRACT

Herein are reported anti-ANG2 antibodies. A specific anti-ANG2 antibody comprises (a) a HVR-H1 comprising the amino acid sequence of SEQ ID NO: 20, (b) a HVR-H2 comprising the amino acid sequence of SEQ ID NO: 21, and (c) a HVR-H3 comprising the amino acid sequence of SEQ ID NO: 23.

6 Claims, No Drawings

Specification includes a Sequence Listing.

(56) References Cited

FOREIGN PATENT DOCUMENTS

| WO | 2011/117329 | | 9/2011 |
|---|---|---|---|
| WO | 2012/021773 | A1 | 2/2012 |
| WO | 2012/034039 | | 3/2012 |
| WO | 2012/125850 | A1 | 9/2012 |
| WO | 2014/001442 | | 1/2014 |
| WO | 2014/009465 | | 1/2014 |
| WO | 2014/072876 | A1 | 5/2014 |
| WO | 2014/074823 | A1 | 5/2014 |
| WO | 2014/109999 | A1 | 7/2014 |
| WO | 2014/177460 | | 11/2014 |
| WO | 2015/107026 | | 7/2015 |

OTHER PUBLICATIONS

Hessen et al., "Dry Eye: and Inflammatory Ocular Disease" Journal of Ophthalmic and Vision Research 9(2):240-250 ( 2014).
IPRP for PCT/EP2015/075879 (dated May 16, 2017).
ISR for PCT/EP2015/075879 (dated Dec. 21, 2015).
Planck et al., "Impact of IL-1 signalling on experimental uveitis and arthritis" Ann Rheum Dis 71(5):753-760 ( 2012).
Solomon et al., "Pro- and Anti-inflammatory Forms of Interleukin-1 in the Tear Fluid and Conjuctiva of Patients with Dry Eye Disease" Investigative Ophthalmology & Visual Science 42(10):2283-2292 ( 2001).
Jo, N. et al., "Inhibition of Platelet-Derived Growth Factor B Signaling Enhances the Efficacy of Anti-Vascular Endothelial Growth Factor Therapy in Multiple Models of Ocular Neovascularization" American Journal of Pathology 168(6):2036-2053 ( 2006).
Kienast et al., "Ang-2-VEGF—A CrossMab, a Novel Bispecific Human IgG1 Antibody Blocking VEGF-A and Ang-Z Functions Simultaneously, Mediates Potent Antitumor, Antiangiogenic, and Antimetastatic Efficacy" Clin Cancer Res 19(24):6730-6740 (Dec. 15, 2013).
Kontermann, "Dual targeting strategies with bispecific antibodies" mAbs (Mar./Apr. 2012), 4(2):182-197.
Leonardzehr et al., "Molecular Partners continues to validate DARPin platform" BioTuesdays: 1-8 ( 2012).
Li, Q. et al., "Therapeutic efficacy of three bispecific antibodies on collagen-induced arthritis mouse model" International Immunopharmacology 21:119-127 ( 2014).

Mabry, R. et al., "A dual-targeting PDGFRβ/VEGF-A molecule assembled from stable antibody fragments demonstrates anti-angiogenic activity in vitro and in vivo" mAbs 2(1):20-34 (2010).
Papadopoulos, K.P. et al., "A phase I first-in-human study of REGN910 (SAR307746), a fully human and selective angiopoietin-2 (Ang2) monoclonal antibody (MAb), in patients with advanced solid tumor malignancies" Abstract (Abstract 2517) ASCO Annual Meeting, (2013) http://meetinglibrary.asco.org/print/1155681.
Schaefer et al., "Immunoglobulin domain crossover as a generic approach for the production of bispecific IgG antibodies" Proceedings of the National Academy of Sciences 108(27):11187-11192 (Jul. 5, 2011).
Thomas et al., "A Novel Angiopoietin-2 Selective Fully Human Antibody with Potent Anti-Tumoral and Anti-Angiogenic Efficacy and Superior Side Effect Profile Compared to Pan-Angiopoietin-1/-2 Inhibitors" PLOS-One 8(2):e54923 (Feb. 2013).
Vassbotn, F.S. et al., "A monoclonal antibody against PDGF B-chain inhibits PDGF-induced DNA synthesis in C3H fibroblasts and prevents binding of PDGF to its receptor" Biochimica et Biophysica Acta 1054(2):246-249 ( 1990).
Wu, C. et al., "Molecular construction and optimization of anti-human IL-1α/β dual variable domain immunoglobulin (DVD-IgTM) molecules" mAbs 1(4):339-347 (2009).
Bezuidenhout et al., "Association of Ang-2 with Integrin Betta2 Controls Ang-2/PDGF-BB-Dependent Upregulation of Human Peripheral Blood Monocyte Fibrinolysis" Inflammation 32(6):393 ( 2009).
Bezuidenthout et al., "Ang-2 and PDGF-BB cooperatively stimulate human peripheral blood monocyte fibrinolysis" Journal of Leukoeyte Biology 81:1496 ( 2007).
Karamysheva, "The Mechanisms of Angiogenesis" Biochimia 73(7):935-948 (Jul. 2008).
Ogawa et al., "Anti-PDGF-B monoclonal antibody reduces liver fibrosis development" Hepatology Research 40:1128-1141 ( 2010).
Pakula et al., "Genetic analysis of protein stability and function" Annu. Rev. Genet. 23:289-310 ( 1989).
Peppercorn et al., "Toward Improved Understanding of the Ethical and Clinical Issues Surrounding Mandatory Research Biopsies" Journal of Clinical Oncology 31(1):1-2 ( 2013).
Rudikoff et al., "Single amino acid substitution altering antigen-binding specificity," Proc. Nat. Acad. Sci. USA, vol. 79, pp. 1979-1983, Mar. 1982.

\* cited by examiner

ANTI-ANG2 ANTIBODIES AND METHODS OF USE

RELATED APPLICATIONS

This application is a continuation of International Application No. PCT/EP2015/075876, filed Nov. 6, 2015, which claims priority to European Application No. EP 14192524.8, filed Nov. 10, 2014, the contents of which are incorporated herein by reference.

FIELD OF THE INVENTION

The present invention relates to anti-ANG2 antibodies and methods of using the same.

SEQUENCE LISTING

This application contains a Sequence Listing which has been submitted via EFS-Web and is hereby incorporated by reference in its entirety. Said ASCII copy, created on Apr. 19, 2017, is named Sequence Listing and is 142,844 bytes in size.

BACKGROUND

Human angiopoietin-2 (ANG-2) (alternatively abbreviated with ANGPT2 or ANG2) (SEQ ID No: 106) is described in Maisonpierre, P. C., et al, Science 277 (1997) 55-60 and Cheung, A. H., et al., Genomics 48 (1998) 389-91. The angiopoietins-1 and -2 (ANG-1 (SEQ ID No: 107) and ANG-2 (SEQ ID No: 106)) were discovered as ligands for the Ties, a family of tyrosine kinases that is selectively expressed within the vascular endothelium. Yancopoulos, G. D., et al., Nature 407 (2000) 242-48. There are now four definitive members of the angiopoietin family. Angiopoietin-3 and -4 (Ang-3 and Ang-4) may represent widely diverged counterparts of the same gene locus in mouse and man. Kim, I., et al., FEBS Let, 443 (1999) 353-56; Kim, I., et al., J. Biol. Chem. 274 (1999) 26523-26528. ANG-1 and ANG-2 were originally identified in tissue culture experiments as agonist and antagonist, respectively (see for ANG-1: Davis, S., et al., Cell 87 (1996) 1161-69; and for ANG-2: Maisonpierre, P. C., et al., Science 277 (1997) 55-60) All of the known angiopoietins bind primarily to Tie2, and both Ang-1 and -2 bind to Tie2 with an affinity of 3 nM (Kd). Maisonpierre, P. C., et al., Science 277 (1997) 55-60. Ang-1 was shown to support EC survival and to promote endothelium integrity, Davis, S., et al., Cell 87 (1996) 1161-69; Kwak, H. J., et al., FEBS Lett 448 (1999) 249-53; Suri, C., et al., Science 282 (1998) 468-71; Thurston, G., et al., Science 286 (1999) 2511-2514; Thurston, G., et al., Nat. Med. 6 (2000) 460-63, whereas ANG-2 had the opposite effect and promoted blood vessel destabilization and regression in the absence of the survival factors VEGF or basic fibroblast growth factor. Maisonpierre, P. C., et al., Science 277 (1997) 55-60. However, many studies of ANG-2 function have suggested a more complex situation. ANG-2 might be a complex regulator of vascular remodeling that plays a role in both vessel sprouting and vessel regression. Supporting such roles for ANG-2, expression analyses reveal that ANG-2 is rapidly induced, together with VEGF, in adult settings of angiogenic sprouting, whereas ANG-2 is induced in the absence of VEGF in settings of vascular regression. Holash, J., et al., Science 284 (1999) 1994-98; Holash, J., et al., Oncogene 18 (1999) 5356-62. Consistent with a context-dependent role, ANG-2 specifically binds to the same endothelial-specific receptor, Tie-2, which is activated by Ang-1, but has context-dependent effects on its activation. Maisonpierre, P. C., et al., Science 277 (1997) 55-60.

Corneal angiogenesis assays have shown that both ANG-1 and ANG-2 had similar effects, acting synergistically with VEGF to promote growth of new blood vessels. Asahara, T., et al., Circ. Res. 83 (1998) 233-40. The possibility that there was a dose-dependent endothelial response was raised by the observation that in vitro at high concentration, ANG-2 can also be pro-angiogenic. Kim, I., et al., Oncogene 19 (2000) 4549-52. At high concentration, ANG-2 acts as an apoptosis survival factor for endothelial cells during serum deprivation apoptosis through activation of Tie2 via PI-3 Kinase and Akt pathway. Kim, I., et al., Oncogene 19 (2000) 4549-52.

Other in vitro experiments suggested that during sustained exposure, the effects of ANG-2 may progressively shift from that of an antagonist to an agonist of Tie2, and at later time points, it may contribute directly to vascular tube formation and neovessel stabilization. Teichert-Kuliszewska, K., et al., Cardiovas. Res. 49 (2001) 659-70. Furthermore, if ECs were cultivated on fibrin gel, activation of Tie2 with ANG-2 was also observed, perhaps suggesting that the action of ANG-2 could depend on EC differentiation state. Teichert-Kuliszewska, K., et al., Cardiovas. Res. 49 (2001) 659-70. In microvascular EC cultured in a three-dimensional collagen gel, ANG-2 can also induce Tie2 activation and promote formation of capillary-like structures. Mochizuki, Y., et al., J. Cell. Sci. 115 (2002) 175-83. Use of a 3-D spheroidal co-culture as an in-vitro model of vessel maturation demonstrated that direct contact between ECs and mesenchymal cells abrogates responsiveness to VEGF, whereas the presence of VEGF and ANG-2 induced sprouting. Korff, T., et al., FASEB J. 15 (2001) 447-457. Etoh, T. H. et al. demonstrated that ECs that constitutively express Tie2, the expression of MMP-1, -9 and u-PA were strongly upregulated by ANG-2 in the presence of VEGF. Etoh, T., et al., Cancer Res. 61 (2001) 2145-53. With an in vivo pupillary membrane model, Lobov, I. B. et al. showed that ANG-2 in the presence of endogenous VEGF promotes a rapid increase in capillary diameter, remodeling of the basal lamina, proliferation and migration of endothelial cells, and stimulates sprouting of new blood vessels. Lobov, I. B., et al., Proc. Natl. Acad. Sci. USA 99 (2002) 11205-10. By contrast, ANG-2 promotes endothelial cell death and vessel regression without endogenous VEGF. Lobov, I. B., et al., Proc. Natl. Acad. Sci. USA 99 (2002) 11205-10. Similarly, with an in vivo tumor model, Vajkoczy, P., et al. demonstrated that multicellular aggregates initiate vascular growth by angiogenic sprouting via the simultaneous expression of VEGFR-2 and ANG-2 by host and tumor endothelium. Vajkoczy, P., et al., J. Clin. Invest. 109 (2002) 777-85. This model illustrated that the established microvasculature of growing tumors is characterized by a continuous remodeling, putatively mediated by the expression of VEGF and ANG-2 (Vajkoczy, P., et al., J. Clin. Invest. 109 (2002) 777-85).

Knock-out mouse studies of Tie-2 and Angiopoietin-1 show similar phenotypes and suggest that Angiopoietin-1 stimulated Tie-2 phosphorylation mediates remodeling and stabilization of developing vessel, promoting blood vessel maturation during angiogenesis and maintenance of endothelial cell-support cell adhesion (Dumont, D. J., et al., Genes & Development, 8 (1994) 1897-1909; Sato, T. N., Nature, 376 (1995) 70-74; (Thurston, G., et al., Nature Medicine 6 (2000) 460-463). The role of Angiopoietin-1 is thought to be conserved in the adult, where it is expressed widely and constitutively (Hanahan, D., Science, 277 (1997)

48-50; Zagzag, D., et al., Exp. Neurol. 159 (1999) 391-400). In contrast, Angiopoietin-2 expression is primarily limited to sites of vascular remodeling where it is thought to block the constitutive stabilizing or maturing function of Angiopoietin-1, allowing vessels to revert to, and remain in, a plastic state which may be more responsive to sprouting signals (Hanahan, D., 1997; Holash, J., et al., Oncogene 18 (199) 5356-62; Maisonpierre, P. C., 1997). Studies of Angiopoietin-2 expression in pathological angiogenesis have found many tumor types to show vascular Angiopoietin-2 expression (Maisonpierre, P. C., et al., Science 277 (1997) 55-60). Functional studies suggest Angiopoietin-2 is involved in tumor angiogenesis and associate Angiopoietin-2 overexpression with increased tumor growth in a mouse xenograft model (Ahmad, S. A., et al., Cancer Res., 61 (2001) 1255-1259). Other studies have associated Angiopoietin-2 overexpression with tumor hyper-vascularity (Etoh, T., et al., Cancer Res. 61 (2001) 2145-53; Tanaka, F., et al., Cancer Res. 62 (2002) 7124-7129).

In recent years Angiopoietin-1, Angiopoietin-2 and/or Tie-2 have been proposed as possible anti-cancer therapeutic targets. For example U.S. Pat. Nos. 6,166,185, 5,650,490 and 5,814,464 each disclose anti-Tie-2 ligand and receptor antibodies. Studies using soluble Tie-2 were reported to decrease the number and size of tumors in rodents (Lin, 1997; Lin 1998). Siemeister, G., et al., Cancer Res. 59:3 (1999) 3185-91 generated human melanoma cell lines expressing the extracellular domain of Tie-2, injected these into nude mice and reported soluble Tie-2 to result in significant inhibition of tumor growth and tumor angiogenesis. Given both Angiopoietin-1 and Angiopoietin-2 bind to Tie-2, it is unclear from these studies whether Angiopoietin-1, Angiopoietin-2 or Tie-2 would be an attractive target for anti-cancer therapy. However, effective anti-Angiopoietin-2 therapy is thought to be of benefit in treating diseases such as cancer, in which progression is dependent on aberrant angiogenesis where blocking the process can lead to prevention of disease advancement (Folkman, J., Nature Medicine. 1 (1995) 27-31).

In addition some groups have reported the use of antibodies and peptides that bind to Angiopoietin-2. See, for example, U.S. Pat. No. 6,166,185 and US 2003/10124129. WO 03/030833, WO 2006/068953, WO 03/057134 or US 2006/0122370.

Study of the effect of focal expression of Angiopoietin-2 has shown that antagonizing the Angiopoietin-1/Tie-2 signal loosens the tight vascular structure thereby exposing ECs to activating signals from angiogenesis inducers, e.g. VEGF (Hanahan, D., Science, 277 (1997) 48-50). This pro-angiogenic effect resulting from inhibition of Angiopoietin-1 indicates that anti-Angiopoietin-1 therapy would not be an effective anti-cancer treatment.

ANG-2 is expressed during development at sites where blood vessel remodeling is occurring. Maisonpierre, P. C., et al., Science 277 (1997) 55-60. In adult individuals, ANG-2 expression is restricted to sites of vascular remodeling as well as in highly vascularized tumors, including glioma, Osada, H., et al., Int. J. Oncol. 18 (2001) 305-09); Koga, K., et al., Cancer Res. 61 (2001) 6248-54, hepatocellular carcinoma, Tanaka, S., et al., J. Clin. Invest. 103 (1999) 341-45, gastric carcinoma, Etoh, T., et al., Cancer Res. 61 (2001) 2145-53; Lee, J. H., et al., Int. J. Oncol. 18 (2001) 355-61, thyroid tumor, Bunone, G., et al., Am J Pathol 155 (1999) 1967-76 non-small cell lung cancer, Wong, M. P., et al., Lung Cancer 29 (2000) 11-22, and cancer of colon, Ahmad, S. A., et al., Cancer 92 (2001) 1138-43, and prostate Wurmbach, J. H., et al., Anticancer Res. 20 (2000) 5217-20.

Some tumor cells are found to express ANG-2. For example, Tanaka, S., et al., J. Clin. Invest. 103 (1999) 341-45 detected ANG-2 mRNA in 10 out of 12 specimens of human hepatocellular carcinoma (HCC). Ellis' group reported that ANG-2 is expressed ubiquitously in tumor epithelium. Ahmad, S. A., et al., Cancer 92 (2001) 1138-43. Other investigators reported similar findings. Chen, L., et al., J. Tongji Med. Univ. 21 (2001) 228-35. By detecting ANG-2 mRNA levels in archived human breast cancer specimens, Sfiligoi, C., et al., Int. J. Cancer 103 (2003) 466-74 reported that ANG-2 mRNA is significantly associated with auxiliary lymph node invasion, short disease-free time and poor overall survival. Tanaka, F., et al., Cancer Res. 62 (2002) 7124-29 reviewed a total of 236 patients of non-small cell lung cancer (NSCLC) with pathological stage-I to -IIIA, respectively. Using immunohistochemistry, they found that 16.9% of the NSCLC patients were ANG-2 positive. The microvessel density for ANG-2 positive tumor is significantly higher than that of ANG-2 negative. Such an angiogenic effect of ANG-2 was seen only when VEGF expression was high. Moreover, positive expression of ANG-2 was a significant factor to predict a poor postoperative survival. Tanaka, F., et al., Cancer Res. 62 (2002) 7124-7129. However, they found no significant correlation between Ang-1 expression and the microvessel density. Tanaka, F., et al., Cancer Res. 62 (2002) 7124-7129. These results suggest that ANG-2 is an indicator of poor prognosis patients with several types of cancer.

Recently, using an ANG-2 knockout mouse model, Yancopoulos' group reported that ANG-2 is required for postnatal angiogenesis. Gale, N. W., et al., Dev. Cell 3 (2002) 411-23. They showed that the developmentally programmed regression of the hyaloid vasculature in the eye does not occur in the ANG-2 knockout mice and their retinal blood vessels fail to sprout out from the central retinal artery. Gale, N. W., et al., Dev. Cell 3 (2002) 411-423. They also found that deletion of ANG-2 results in profound defects in the patterning and function of the lymphatic vasculature. Gale, N. W., et al., Dev. Cell 3 (2002) 411-423. Genetic rescue with Ang-1 corrects the lymphatic, but not the angiogenesis defects. Gale, N. W., et al., Dev. Cell 3 (2002) 411-423.

Peters and his colleagues reported that soluble Tie2, when delivered either as recombinant protein or in a viral expression vector, inhibited in vivo growth of murine mammary carcinoma and melanoma in mouse models. Lin, P., et al., Proc. Natl. Acad. Sci. USA 95 (1998) 8829-34; Lin, P., et al., J. Clin. Invest. 100 (1997) 2072-78. Vascular densities in the tumor tissues so treated were greatly reduced. In addition, soluble Tie2 blocked angiogenesis in the rat corneal stimulated by tumor cell conditioned media. Lin, P., et al., J. Clin. Invest. 100 (1997) 2072-78. Furthermore, Isner and his team demonstrated that addition of ANG-2 to VEGF promoted significantly longer and more circumferential neovascularity than VEGF alone. Asahara, T., et al., Circ. Res. 83 (1998) 233-40. Excess soluble Tie2 receptor precluded modulation of VEGF-induced neovascularization by ANG-2. Asahara, T., et al., Circ. Res. 83 (1998) 233-40. Siemeister, G., et al., Cancer Res. 59:3 (1999) 3185-91 showed with nude mouse xenografts that overexpression of the extracellular ligand-binding domains of either Flt-1 or Tie2 in the xenografts results in significant inhibition of pathway could not be compensated by the other one, suggesting that the VEGF receptor pathway and the Tie2 pathway should be considered as two independent mediators essential for the process of in vivo angiogenesis. Siemeister, G., et al., Cancer Res. 59:3 (1999) 3185-3191. This is proven by a more recent publication by White, R., R., et al., Proc. Natl. Acad. Sci. USA 100 (2003) 5028-33. In their study, it was demonstrated that a nuclease-resistant RNA aptamer that specifically binds and inhibits ANG-2 significantly inhibited neovascularization induced by bFGF in the rat corneal micropocket angiogenesis model.

Ocular vascular diseases such as age related macular degeneration (AMD) and diabetic retinopathy (DR) are due to abnormal choroidal or retinal neovascularization, respectively. They are the leading causes of visual loss in industrialized nations. Since the retina consists of well-defined layers of neuronal, glial, and vascular elements, relatively small disturbances such as those seen in vascular proliferation or edema can lead to significant loss of visual function. Inherited retinal degenerations, such as Retinitis Pigmentosa (RP), are also associated with vascular abnormalities, such as arteriolar narrowing and vascular atrophy. They affect as many as 1 in 3,500 individuals and are characterized by progressive night blindness, visual field loss, optic nerve atrophy, arteriolar attenuation, and central loss of vision often progressing to complete blindness.

Ischemic retinopathies are characterized by loss or dysfunction of the retinal vasculature which results in a reduction of blood flow and hypoxia. The retina responds to hypoxia by generating signals to grow new blood vessels, but these new vessels are usually fragile and disorganized. It is the growth of these abnormal new vessels that creates most of the threat to vision since they can leak, lead to hemorrhage or lead to scarring that may end in retinal detachment. Current treatments for ischemic retinopathies seek to halt the growth of the pathological vessels but do not address the underlying ischemia that drives their growth. Furthermore, standard treatment for diabetic retinopathy, an ischemic retinopathy that affects millions, involves destruction of a portion of the retina with a laser in an attempt to stop new vessel growth and preserve central vision. Strategies have been employed to block the function of vascular endothelial growth factor (VEGF), a major promoter of vessel growth. In the short term, anti-VEGF therapy can improve vision, but it does not address the underlying ischemia and in fact may exacerbate this condition as it inhibits all vessel growth, including beneficial collaterals. There is also the serious concern of systemic exposure of these drugs in elderly and/or diabetic patients where new vessel growth may be required in ischemic brains, hearts or limbs.

Typically for ocular diseases via intravitreal application smaller antibody fragments like Fab or $Fab_2$ are often used as they have a low serum half-life and the risk of systemic toxicities is lower. However this smaller fragments typically have also lower intravitreal half-lives (e.g. due to the faster diffusion into serum) and have to be dosed typically more often.

Multispecific antibodies with a domain replacement/exchange in one binding arm (CrossMabVH-VL) are described in detail in WO 2009/080252 and Schaefer, W. et al, Proc. Natl. Acad. Sci. USA, 108 (2011) 11187-11191 (which are incorporated as reference herein). They clearly reduce the byproducts caused by the mismatch of a light chain against a first antigen with the wrong heavy chain against the second antigen (compared to approaches without such domain exchange). However their preparation is not completely free of side products. The main side product is based on a Bence-Jones-type interaction. See also Schaefer, W. et al, Proc. Natl. Acad. Sci. USA, 108 (2011) 11187-11191; in Figure S1I of the Supplement).

In WO 2010/040508 bispecific anti-VEGF/anti-ANG-2 antibodies are reported. Human FcRn-binding modified antibodies and methods of use are reported in WO 2014/177460.

Thomas, M., et al. reported a novel angiopoietin-2 selective fully human antibody with potent anti-tumoral and anti-angiogenic efficacy and superior side effect profile compared to pan-angiopoietin-1/-2 inhibitors (PLOS One 8 (2013) E54923). Papadopoulos, K. P., et al. reported a phase I first-in-human study of REGN910 (SAR307746), a fully human and selective angiopoietin-2 (Ang2) monoclonal antibody (MAb), in patients with advanced solid tumor malignancies (abstract 2517, ASCO Annual Meeting 2013).

SUMMARY

The invention provides anti-ANG2 antibodies and methods of using the same. In specific embodiments the antibody is an affinity matured antibody.

One aspect as reported herein is an antibody that specifically binds to human ANG2, wherein the antibody comprises (a) a HVR-H1 comprising the amino acid sequence of SEQ ID NO: 20, (b) a HVR-H2 comprising the amino acid sequence of SEQ ID NO: 21, and (c) a HVR-H3 comprising the amino acid sequence of SEQ ID NO: 23.

In one embodiment of all aspects as reported herein the antibody further comprises (a) a HVR-L1 comprising the amino acid sequence of SEQ ID NO: 25; (b) a HVR-L2 comprising the amino acid sequence of SEQ ID NO: 26; and (c) HVR-L3 comprising the amino acid sequence of SEQ ID NO: 27.

One aspect as reported herein is an antibody that specifically binds to human ANG2, wherein the antibody comprises (a) a HVR-H1 comprising the amino acid sequence of SEQ ID NO: 29, (b) a HVR-H2 comprising the amino acid sequence of SEQ ID NO: 30, and (c) a HVR-H3 comprising the amino acid sequence of SEQ ID NO: 32.

In one embodiment of all aspects as reported herein the antibody further comprises (a) a HVR-L1 comprising the amino acid sequence of SEQ ID NO: 34; (b) a HVR-L2 comprising the amino acid sequence of SEQ ID NO: 35; and (c) HVR-L3 comprising the amino acid sequence of SEQ ID NO: 36.

One aspect as reported herein is an antibody that specifically binds to human ANG2, wherein the antibody comprises (a) a HVR-H1 comprising the amino acid sequence of SEQ ID NO: 38, (b) a HVR-H2 comprising the amino acid sequence of SEQ ID NO: 39, and (c) a HVR-H3 comprising the amino acid sequence of SEQ ID NO: 41.

In one embodiment of all aspects as reported herein the antibody further comprises (a) a HVR-L1 comprising the amino acid sequence of SEQ ID NO: 43; (b) a HVR-L2 comprising the amino acid sequence of SEQ ID NO: 44; and (c) HVR-L3 comprising the amino acid sequence of SEQ ID NO: 45.

In one embodiment the antibody comprises a heavy chain variable domain that has the amino acid sequence of SEQ ID NO: 19 and a light chain variable domain that has the amino acid sequence of SEQ ID NO: 6 or SEQ ID NO: 33.

One aspect as reported herein is an antibody that specifically binds to human ANG2, wherein the antibody
  i) comprises a heavy chain variable domain that has a sequence identity to SEQ ID NO: 19 of more than 70%, or 85%, or 90%, or 95%, and a light chain variable domain that has a sequence identity to SEQ ID NO: 6 of more than 70%, or 85%, or 90%, or 95%,
  ii) has in the heavy chain variable domain at position 28 the amino acid residue asparagine (N), at position 30 the amino acid residue alanine (A), at position 100b the amino acid residue proline (P) and at position 100j the amino acid residue alanine (A) and in the light chain variable domain at position 51 the amino acid residue threonine (T) (numbering according to Kabat), and iii) the antibody has a lower $EC_{50}$ value for the inhibition of the binding of ANG2 to its receptor Tie2 in a cell based assay using HEK293 cells stably expressing human Tie2 determined using a Tie2 phosphorylation ELISA compared to an antibody comprising a heavy chain variable domain that has the sequence of SEQ ID NO: 19 and a light chain variable domain that has the sequence of SEQ ID NO: 6 or SEQ ID NO: 33.

In one embodiment of all aspects as reported herein the antibody is of the human subclass IgG1 or the human subclass IgG4.

In one embodiment of all aspects as reported herein the antibody is of the human subclass IgG1 with a kappa light chain.

In one embodiment of all aspects as reported herein the antibody is of the human subclass IgG1 with a lambda light chain.

In one embodiment of all aspects as reported herein the antibody is a monoclonal antibody.

One aspect as reported herein is an antibody comprising a VH sequence of SEQ ID NO: 19 and a VL sequence of SEQ ID NO: 24.

One aspect as reported herein is an antibody comprising a VH sequence of SEQ ID NO: 28 and a VL sequence of SEQ ID NO: 33.

One aspect as reported herein is an antibody comprising a VH sequence of SEQ ID NO: 37 and a VL sequence of SEQ ID NO: 42.

In one embodiment the antibody is a bispecific antibody.

In one embodiment of all aspects the humanized antibody blocks the biological activity of human ANG2 by inhibiting the binding of human ANG2 to the Tie2 receptors.

One aspect as reported herein is an antibody Fab fragment that specifically binds to human ANG2, wherein the antibody Fab fragment comprises (a) a HVR-H1 comprising the amino acid sequence of SEQ ID NO: 20, (b) a HVR-H2 comprising the amino acid sequence of SEQ ID NO: 21, and (c) a HVR-H3 comprising the amino acid sequence of SEQ ID NO: 23.

In one embodiment of all aspects as reported herein the antibody Fab fragment further comprises (a) a HVR-L1 comprising the amino acid sequence of SEQ ID NO: 25; (b) a HVR-L2 comprising the amino acid sequence of SEQ ID NO: 26; and (c) HVR-L3 comprising the amino acid sequence of SEQ ID NO: 27.

One aspect as reported herein is an antibody Fab fragment that specifically binds to human ANG2, wherein the antibody Fab fragment comprises (a) a HVR-H1 comprising the amino acid sequence of SEQ ID NO: 29, (b) a HVR-H2 comprising the amino acid sequence of SEQ ID NO: 30, and (c) a HVR-H3 comprising the amino acid sequence of SEQ ID NO: 32.

In one embodiment of all aspects as reported herein the antibody Fab fragment further comprises (a) a HVR-L1 comprising the amino acid sequence of SEQ ID NO: 34; (b) a HVR-L2 comprising the amino acid sequence of SEQ ID NO: 35; and (c) HVR-L3 comprising the amino acid sequence of SEQ ID NO: 36.

One aspect as reported herein is an antibody Fab fragment that specifically binds to human ANG2, wherein the antibody Fab fragment comprises (a) a HVR-H1 comprising the amino acid sequence of SEQ ID NO: 38, (b) a HVR-H2 comprising the amino acid sequence of SEQ ID NO: 39, and (c) a HVR-H3 comprising the amino acid sequence of SEQ ID NO: 41.

In one embodiment of all aspects as reported herein the antibody Fab fragment further comprises (a) a HVR-L1 comprising the amino acid sequence of SEQ ID NO: 43; (b) a HVR-L2 comprising the amino acid sequence of SEQ ID NO: 44; and (c) HVR-L3 comprising the amino acid sequence of SEQ ID NO: 45.

One aspect as reported herein is an antibody Fab fragment comprising a VH sequence of SEQ ID NO: 19 and a VL sequence of SEQ ID NO: 24.

One aspect as reported herein is an antibody Fab fragment comprising a VH sequence of SEQ ID NO: 28 and a VL sequence of SEQ ID NO: 33.

One aspect as reported herein is an antibody Fab fragment comprising a VH sequence of SEQ ID NO: 37 and a VL sequence of SEQ ID NO: 42.

One aspect as reported herein is a scFv antibody fragment that specifically binds to human ANG2, wherein the scFv antibody fragment comprises (a) a HVR-H1 comprising the amino acid sequence of SEQ ID NO: 20, (b) a HVR-H2 comprising the amino acid sequence of SEQ ID NO: 21, and (c) a HVR-H3 comprising the amino acid sequence of SEQ ID NO: 23.

In one embodiment of all aspects as reported herein the scFv antibody fragment further comprises (a) a HVR-L1 comprising the amino acid sequence of SEQ ID NO: 25; (b) a HVR-L2 comprising the amino acid sequence of SEQ ID NO: 26; and (c) HVR-L3 comprising the amino acid sequence of SEQ ID NO: 27.

One aspect as reported herein is a scFv antibody fragment that specifically binds to human ANG2, wherein the scFv antibody fragment comprises (a) a HVR-H1 comprising the amino acid sequence of SEQ ID NO: 29, (b) a HVR-H2 comprising the amino acid sequence of SEQ ID NO: 30, and (c) a HVR-H3 comprising the amino acid sequence of SEQ ID NO: 32.

In one embodiment of all aspects as reported herein the scFv antibody fragment further comprises (a) a HVR-L1 comprising the amino acid sequence of SEQ ID NO: 34; (b) a HVR-L2 comprising the amino acid sequence of SEQ ID NO: 35; and (c) HVR-L3 comprising the amino acid sequence of SEQ ID NO: 36.

One aspect as reported herein is a scFv antibody fragment that specifically binds to human ANG2, wherein the scFv antibody fragment comprises (a) a HVR-H1 comprising the amino acid sequence of SEQ ID NO: 38, (b) a HVR-H2 comprising the amino acid sequence of SEQ ID NO: 39, and (c) a HVR-H3 comprising the amino acid sequence of SEQ ID NO: 41.

In one embodiment of all aspects as reported herein the scFv antibody fragment further comprises (a) a HVR-L1 comprising the amino acid sequence of SEQ ID NO: 43; (b) a HVR-L2 comprising the amino acid sequence of SEQ ID NO: 44; and (c) HVR-L3 comprising the amino acid sequence of SEQ ID NO: 45.

One aspect as reported herein is a scFv antibody fragment comprising a VH sequence of SEQ ID NO: 19 and a VL sequence of SEQ ID NO: 24.

One aspect as reported herein is a scFv antibody fragment comprising a VH sequence of SEQ ID NO: 28 and a VL sequence of SEQ ID NO: 33.

One aspect as reported herein is a scFv antibody fragment comprising a VH sequence of SEQ ID NO: 37 and a VL sequence of SEQ ID NO: 42.

One aspect as reported herein is an anti-ANG2 antibody that interacts with at least 90% of the residues of ANG2 as an antibody as reported herein when determined by X-ray crystallography.

One aspect as reported herein is an anti-ANG2 antibody that interacts with at least the same residues of ANG2 as an antibody as reported herein when determined by X-ray crystallography.

One aspect as reported herein is an anti-ANG2 antibody that interacts with at least 90% of the residues of ANG2 as an antibody as reported herein when determined by X-ray crystallography and inhibits the binding of ANG2 to its receptor.

One aspect as reported herein is an anti-ANG2 antibody that interacts with at least the same residues of ANG2 as an antibody as reported herein when determined by X-ray crystallography and inhibits the binding of ANG2 to its receptor.

One aspect as reported herein is an (isolated) nucleic acid encoding the antibody as reported herein.

One aspect as reported herein is a host cell comprising the nucleic acid as reported herein.

One aspect as reported herein is a method of producing an antibody as reported herein comprising culturing the host cell as reported herein to produce the antibody and recovering the antibody from the host cell or the cultivation medium.

One aspect as reported herein is a pharmaceutical formulation comprising an antibody as reported herein and a pharmaceutically acceptable carrier.

In one embodiment the pharmaceutical formulation further comprises an additional therapeutic agent. In one embodiment the additional therapeutic agent is an anti-VEGF antibody, an anti-IL-1beta antibody or an anti-PDGF-B antibody.

One aspect as reported herein is the antibody as reported herein for use as a medicament.

One aspect as reported herein is the antibody as reported herein for the treatment of vascular diseases.

One aspect as reported herein a pharmaceutical composition for the treatment of vascular diseases.

One aspect as reported herein is the use of an antibody as reported herein for the manufacture of a medicament for the treatment of vascular diseases.

One aspect as reported herein is a method of treatment of a patient suffering from a vascular disease by administering an antibody as reported herein to a patient in the need of such treatment.

One aspect as reported herein is the antibody as reported herein for use in treating a vascular disease, preferably for use in treating cancer.

One embodiment of the invention is the antibody as reported herein for the treatment of cancer.

One aspect as reported herein is for use as a medicament for use in the treatment of cancer.

One aspect as reported herein is the use of an antibody as reported herein for the manufacture of a medicament for the treatment of cancer.

One aspect as reported herein is a method of treatment of a patient suffering from cancer by administering an antibody as reported herein to a patient in the need of such treatment.

One aspect as reported herein is for use as a medicament for the prevention of metastasis.

One aspect as reported herein is the use of an antibody as reported herein for the manufacture of a medicament for the prevention of metastasis.

One aspect as reported herein is a method of prevention of metastasis in a patient suffering from primary cancer by administering an antibody as reported herein to a patient in the need of such preventive treatment.

One aspect as reported herein is the antibody as reported herein for use in treating an ocular vascular disease, preferably for use in treating macular degeneration.

The antibody as reported herein for use in inhibiting the interaction between ANG2 and the Tie2 receptor.

One aspect as reported herein is the use of the antibody as reported herein in the manufacture of a medicament.

In one embodiment the medicament is for the treatment of an ocular vascular disease, preferably for the treatment of macular degeneration.

In one embodiment the medicament is for inhibiting the interaction between ANG2 and the Tie2 receptor.

One aspect as reported herein is a method of treating an individual having on ocular vascular disease, preferably macular degeneration, comprising administering to the individual an effective amount of the antibody as reported herein.

One aspect as reported herein is a method of inhibiting the interaction between ANG2 and the Tie2 receptor in an individual comprising administering to the individual an effective amount of the antibody as reported herein to inhibiting the interaction between ANG2 and the Tie2 receptor.

DETAILED DESCRIPTION OF EMBODIMENTS OF THE INVENTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($k_d$). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-ANG2 antibody" and "an antibody that binds to ANG2" refer to an antibody that is capable of binding ANG2 with sufficient affinity such that the antibody is useful as a diagnostic and/or therapeutic agent in targeting ANG2. In one embodiment, the extent of binding of an anti-ANG2 antibody to an unrelated, non-ANG2 protein is less than about 10% of the binding of the antibody to ANG2 as measured, e.g., by ELISA or surface plasmon resonance. In certain embodiments, an antibody that binds to ANG2 has a dissociation constant (KD) of ≤1 μM, ≤100 nM, or ≤10 nM (e.g. $10^{-8}$M or less). In certain embodiments, an anti-ANG2 antibody binds to an epitope of ANG2 that is conserved among ANG2 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that has interactions with at least the same amino acid residues as the reference antibody. These interactions are e.g. ionic interactions between charged amino acid residues or hydrophobic interactions between hydrophobic amino acid residues.

The term "chimeric" antibody refers to an antibody in which a portion of the heavy and/or light chain is derived from a particular source or species, while the remainder of the heavy and/or light chain is derived from a different source or species.

The term "cancer" as used herein refers to proliferative diseases, such as lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewing's sarcoma, including refractory versions of any of the above cancers, or a combination of one or more of the above cancers.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "immunoconjugate" denotes a covalent conjugate between an antibody and a non-antibody moiety. Such a non-antibody moiety can be a detectable label, an effector molecule or a cytotoxic agent.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) or the C-terminal glycyl-lysine dipeptide (Gly446Lys447) of the Fc-region may or may not be present. Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody," and "whole antibody" are used herein interchangeably to refer to an antibody having a structure substantially similar to a native antibody structure or having heavy chains that contain an Fc-region as defined herein.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs herein include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242.);
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
(d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s).

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-ANG2 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "metastasis" according to the invention refers to the transmission of cancerous cells from the primary tumor to one or more sites elsewhere in a patient where then secondary tumors develop. Means to determine if a cancer has metastasized are known in the art and include bone scan, chest X-ray, CAT scan, MRI scan, and tumor marker tests.

The term "prevention of metastasis" or "prevention of secondary tumors" as used herein have the same meaning and refers a prophylactic agent against metastasis in patient suffering from cancer in this way inhibiting or reducing a further transmission of cancerous cells from the primary tumor to one or more sites elsewhere in a patient. This means that the metastasis of the primary, tumor or cancer is prevented, delayed, or reduced and thus the development of secondary tumors is prevented, delayed, or reduced. Preferably the metastasis i.e. secondary tumors of the lung are prevented or reduced, which means that metastatic transmission of cancerous cells from the primary tumor to the lung is prevented or reduced.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "ANG2" as used herein refers to human angiopoietin-2 (ANG-2) (alternatively abbreviated with ANGPT2 or ANG2) (SEQ ID NO: 54) which is described e.g. in Maisonpierre, P. C., et al, Science 277 (1997) 55-60 and Cheung, A. H., et al., Genomics 48 (1998) 389-91. The angiopoietins-1 and -2 were discovered as ligands for the Ties, a family of tyrosine kinases that is selectively expressed within the vascular endothelium (Yancopoulos, G. D., et al., Nature 407 (2000) 242-248). There are now four definitive members of the angiopoietin family. Angiopoietin-3 and -4 (ANG3 and ANG4) may represent widely diverged counterparts of the same gene locus in mouse and man (see e.g. Kim, I., et al., FEBS Lett., 443 (1999) 353-56; Kim, I., et al., J. Biol. Chem. 274 (1999) 26523-26528). ANG1 and ANG2 were originally identified in tissue culture experiments as agonist and antagonist, respectively (see for ANG1: Davis, S., et al., Cell 87 (1996) 1161-69; for ANG2: Maisonpierre, P. C., et al., Science 277 (1997) 55-60) All of the known angiopoietins bind primarily to Tie2, and both ANG1 and ANG2 bind to Tie2 with an affinity of 3 nM (Kd) (Maisonpierre, P. C., et al., Science 277 (1997) 55-60).

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "vascular diseases" includes Cancer, Inflammatory diseases, Atherosclerosis, Ischemia, Trauma, Sepsis, COPD, Asthma, Diabetes, AMD, Retinopathy, Stroke, Adipositas, Acute lung injury, Hemorrhage, Vascular leak e.g. Cytokine induced, Allergy, Graves' Disease, Hashimoto's Autoimmune Thyroiditis, Idiopathic Thrombocytopenic Purpura, Giant Cell Arteritis, Rheumatoid Arthritis, Systemic Lupus Erythematosus (SLE), Lupus Nephritis, Crohn's Disease, Multiple Sclerosis, Ulcerative Colitis, especially to solid tumors, intraocular neovascular syndromes such as proliferative retinopathies or age-related macular degeneration (AMD), rheumatoid arthritis, and psoriasis (Folkman, J., et al., J. Biol. Chem. 267 (1992) 10931-10934; Klagsbrun, M., et al., Annu. Rev. Physiol. 53 (1991) 217-239; and Garner, A., Vascular diseases, In: Pathobiology of ocular disease, A dynamic approach, Garner, A., and Klintworth, G. K., (eds.), 2nd edition, Marcel Dekker, New York (1994), pp 1625-1710).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Compositions and Methods

Herein are reported anti-ANG2 antibodies with improved affinity.

Antibodies of the invention are useful, e.g., for the treatment of vascular diseases, such as ocular vascular diseases, e.g. macular degeneration, or cancer.

The antibodies according to the invention have highly valuable properties causing a benefit for a patient suffering from such a disease, especially suffering from cancer or macular degeneration. The antibodies as reported herein are highly effective in inhibition of angiogenesis or vascular diseases.

The antibodies according to the invention will be effective in a) tumor growth inhibition, and/or
b) inhibition of tumor angiogenesis or vascular diseases, and/or
c) inhibition of macular degeneration.

A. Exemplary Anti-ANG2 Antibodies as Reported Herein

Herein are reported anti-ANG2 antibodies and fragments thereof with improved binding properties.

TABLE 1

Human ANG2 binding kinetics:

| molecule | $k_a$ (1/Ms) | $k_d$ (1/s) | $K_D$ (nM)* | t1/2 (s) |
|---|---|---|---|---|
| 0009 | 1.92E+06 | 0.07565 | 39 | 9 |
| 0041 | 3.85E+06 | 3.17E−03 | 1 | 219 |
| 0075 | 2.22E+06 | 3.10E−02 | 14 | 22 |

TABLE 1-continued

Human ANG2 binding kinetics:

| molecule | $k_a$ (1/Ms) | $k_d$ (1/s) | $K_D$ (nM)* | t1/2 (s) |
|---|---|---|---|---|
| 0090 | 2.16E+06 | 2.53E−03 | 1 | 274 |
| 0098 | 1.56E+07 | 1.58E−04 | 10* | |
| 0099 | 2.61E+07 | 1.10E−04 | 4* | |
| 0100 | 2.06E+07 | 1.67E−04 | 8* | |
| 0101 | 1.83E+07 | 1.20E−04 | 7* | |

*Avidity.

TABLE 2

Cynomolgus ANG2 binding kinetics:

| molecule | $k_a$ (1/Ms) | $k_d$ (1/s) | $K_D$ (nM)* | t1/2 (s) |
|---|---|---|---|---|
| 0009 | 1.45E+06 | 8.81E−02 | 61 | 8 |
| 0041 | 2.14E+06 | 3.60E−03 | 2 | 193 |
| 0075 | 1.34E+06 | 3.25E−02 | 24 | 21 |
| 0090 | 2.02E+06 | 3.08E−03 | 2 | 225 |

The relative biological activities as determined with an assay according to Example 6 of the antibodies as reported herein are given in Table 3.

TABLE 3

Relative biological activity of different antibodies

| molecule | relative biological activity [%] |
|---|---|
| 0009 | 72 |
| 0041 | 838 |
| 0075 | 128 |
| 0090 | 706 |
| 0098 | 100 |

The thermal stability of the different antibodies has been evaluated by determining the aggregation onset temperature (Tagg) and the melting temperature (Tm) (see Table 4).

TABLE 4

Tagg and Tm of different antibodies

| molecule | Tagg [° C.] | Tm [° C.] |
|---|---|---|
| 0009 | 62.2 | 65.9 |
| 0041 | 63.1 | 66.0 |
| 0075 | 63.6 | 67.0 |
| 0090 | 64.0 | 67.4 |

In addition, the antibodies show good stability in stress tests. The binding activity has been determined using surface plasmon resonance (see Table 5).

TABLE 5

Binding activity of different antibodies using surface plasmon resonance

| | relative binding activity | |
|---|---|---|
| molecule | 2 weeks at 37° C. pH 7.4 | 2 weeks at 40° C. pH 6.0 |
| 0009 | 99% | 91% |
| 0041 | 100% | 101% |

TABLE 5-continued

Binding activity of different antibodies using surface plasmon resonance

| molecule | relative binding activity | |
|---|---|---|
| | 2 weeks at 37° C. pH 7.4 | 2 weeks at 40° C. pH 6.0 |
| 0075 | 101% | 105% |
| 0090 | 112% | 100% |

The same stability can be seen in the CE-SDS analysis (see Table 6).

TABLE 6

Stability of different antibodies by CE-SDS analysis

| molecule | relative area % | | |
|---|---|---|---|
| | start | 2 weeks at 37° C. pH 7.4 | 2 weeks at 40° C. pH 6.0 |
| 0009 | 98.9 | 98.5 | 98.8 |
| 0041 | 98.9 | 98.6 | 98.6 |
| 0090 | 99.2 | 98.5 | 98.2 |

Tables 7-12 summarize the properties of the antibodies as reported herein.

TABLE 7

| | molecule | | | | | | |
|---|---|---|---|---|---|---|---|
| | 0009 | 0015 | 0016 | 0017 | 0021 | 0025 | 0026 |
| format | CrossFab CL-CH1 | CrossFab CL-CH1 | CrossFab CL-CH1 | CrossFab CL-CH1 | CrossFab CL-CH1 | CrossFab CL-CH1 | CrossFab CL-CH1 |
| valency for ANG2 | 1 | 1 | 1 | 1 | 1 | 1 | 1 |
| differences | reference molecule | VH: S100dP VL: wt | VH: S100dP Y100fP VL: wt | VH: S54C D100bC VL: wt | VH: G100jA VL: wt | VH: T28N T30V VL: wt | VH: T28N T30A VL: wt |
| SEQ ID NOs: | HC: 46 LC: 49 | HC: 57 LC: 49 | HC: 58 LC: 49 | HC: 59 LC: 49 | HC: 60 LC: 49 | HC: 61 LC: 49 | HC: 62 LC: 49 |
| ka [1/Ms] | 2.15E+06 | 1.87E+06 | 2.28E+06 | 3.03E+06 | 3.35E+06 | 1.87E+06 | 2.03E+06 |
| kd [1/s] | 7.23E−02 | 1.49E−02 | 2.21E−01 | 3.57E−02 | 3.00E−02 | 7.02E−02 | 3.71E−02 |
| KD [nM] | 34 | 8 | 97 | 12 | 9 | 38 | 18 |
| $t_{1/2}$ (s) | 10 | 46 | 3 | 19 | 23 | 10 | 19 |
| first purification step | kappa select | kappa select | kappa select | kappa select | kappa select | kappa select | kappa select |
| scale [l] | 0.3 | 0.3 | 0.3 | 0.3 | 0.3 | 0.3 | 0.3 |
| yield [mg/l supernatant] | 123 | 153 | 153 | 136 | 103 | 30 | 77 |
| monomer (SEC) [%] | 78 | 76 | 72 | 72 | 74 | 82 | 87 |
| monomer (CE-SDS) [%] | 80 | 66 | 64 | 92 | 77 | 82 | 89 |
| further purification step(s) | SEC | SEC | SEC | SEC | SEC | SEC | SEC |
| yield [mg/l supernatant] | 80 | 77 | 75 | 60 | 60 | 22.8 | 54 |
| monomer (SEC) [%] | >99 | 98 | 99 | 96 | >99 | >99 | >99 |
| monomer (CE-SDS) [%] | >99 | 99 | 99 | 99 | 99 | 98 | 98 |
| binding inhibition ANG2 tie2 receptor EC50 [nM] | 69 | | | | | | |
| T_agg [° C.] | 62 | | | | | | |
| T_m [° C.] | 66 | | | | | | |
| loss of ANG2 binding after 2 weeks incubation at pH 6.0 | 9 | | | | | | |
| loss of ANG2 binding after 2 weeks incubation at pH 7.4 | 1 | | | | | | |

TABLE 8

| | molecule | | | | | | |
|---|---|---|---|---|---|---|---|
| | 0027 | 0028 | 0029 | 0031 | 0032 | 0033 | 0039 |
| format | CrossFab CL-CH1 | CrossFab CL-CH1 | CrossFab CL-CH1 | CrossFab CL-CH1 | CrossFab CL-CH1 | CrossFab CL-CH1 | CrossFab CL-CH1 |
| valency for ANG2 | 1 | 1 | 1 | 1 | 1 | 1 | 1 |
| differences | VH: T28N T30K VL: wt | VH: T30K VL: wt | VH: S100dP G100jA VL: wt | VH: wt VL: Y48W | VH: wt VL: D49S | VH: T28N S100dP G100jA VL: wt | VH: D100bT VL: D50T |
| SEQ ID Nos: | HC: 63 LC: 49 | HC: 64 LC: 49 | HC: 65 LC: 49 | HC: 46 LC: 66 | HC: 46 LC: 67 | HC: 68 LC: 49 | HC: 69 LC: 50 |
| ka [1/Ms] | 2.40E+06 | 1.81E+06 | 2.41E+06 | 1.15E+06 | 8.90E+05 | 7.53E+05 | 1.14E+06 |
| kd [1/s] | 1.65E−01 | 2.59E−01 | 4.24E−03 | 4.48E−01 | 1.38E−01 | 2.25E−03 | 0.1848 |
| $K_D$ [nM] | 69 | 143 | 2 | 391 | 154 | 3 | 162 |
| $t_{1/2}$ (s) | 4 | 3 | 164 | 2 | 5 | 308 | 4 |
| first purification step | kappa select | kappa select | kappa select | kappa select | kappa select | kappa select | kappa select |
| scale [l] | 0.3 | 0.3 | 0.3 | 0.3 | 0.3 | 0.3 | 0.3 |
| yield [mg/l supernatant] | 150 | 155 | 136 | 140 | 47.6 | | 163.8 |
| monomer (SEC) [%] | 80 | 84 | 80 | 93 | 89 | 48 | 86 |
| monomer (CE-SDS) [%] | 80 | 85 | 76 | 92 | 92 | 16 + 41 | 92 |
| further purification step(s) | SEC | SEC | SEC | SEC | SEC | SEC | SEC |
| yield [mg/l supernatant] | 109.6 | 116.5 | 89 | 118.5 | 38.5 | 54 | 115 |
| monomer (SEC) [%] | >99 | >99 | >99 | >99 | >99 | >99 | >95 |
| monomer (CE-SDS) [%] | 98 | 99 | 98 | 98 | 99 | 27 + 72 | 98 |
| binding inhibition ANG2 tie2 receptor EC50 [nM] | | | | | | | |
| T_agg [° C.] | | | | | | | |
| T_m [° C.] | | | | | | | |
| loss of ANG2 binding after 2 weeks incubation at pH 6.0 | | | | | | | |
| loss of ANG2 binding after 2 weeks incubation at pH 7.4 | | | | | | | |

TABLE 9

| | molecule | | | | | | |
|---|---|---|---|---|---|---|---|
| | 0040 | 0041 | 0042 | 0057 | 0058 | 0060 | 0061 |
| format | CrossFab CL-CH1 | CrossFab CL-CH1 | CrossFab CL-CH1 | CrossFab CL-CH1 | CrossFab CL-CH1 | CrossFab CL-CH1 | CrossFab CL-CH1 |
| valency for ANG2 | 1 | 1 | 1 | 1 | 1 | 1 | 1 |
| differences | VH: S100dP G100jA T28N T30V VL: wt | VH: S100dP G100jA T28N T30A VL: wt | VH: S100dP G100jA T28N T30K VL: wt | VH: S100dP G100jA T28N T30A D100bE VL: wt | VH: S100dP G100jA T28N T30A D100bT VL: wt | VH: S100dP G100jA T28N T30A D100bE VL: D50T | VH: S100dP G100jA T28N T30A D100bT VL: D50T |
| SEQ ID NOs: | HC: 70 LC: 49 | HC: 47 LC: 49 | HC: 71 LC: 49 | HC: 72 LC: 49 | HC: 73 LC: 49 | HC: 72 LC: 50 | HC: 73 LC: 50 |
| ka [1/Ms] | 2.59E+06 | 3.85E+06 | 3.22E+06 | 3.28E+06 | 1.80E+06 | 3.72E+06 | 1.80E+06 |
| kd [1/s] | 5.92E−03 | 3.17E−03 | 1.28E−02 | 0.09483 | 0.03832 | 0.0786 | 0.03145 |
| KD [nM] | 23 | 1 | 4 | 29 | 21 | 21 | 18 |
| $t_{1/2}$ (s) | 117 | 219 | 54 | 7 | 18 | 9 | 22 |
| first purification step | kappa select | kappa select | kappa select | kappa select | kappa select | kappa select | kappa select |
| scale [l] | 0.3 | 0.3 | 0.3 | 0.3 | 0.3 | 0.3 | 0.3 |
| yield [mg/l supernatant] | | | | 118.3 | 114.3 | 144.9 | 176.6 |
| monomer (SEC) [%] | | | | 67 | 77 | 70 | 75 |
| monomer (CE-SDS) [%] | | | | 72 | 77 | 76 | 82 |
| further purification step(s) | SEC | SEC | SEC | SEC | SEC | SEC | SEC |
| yield [mg/l supernatant] | 28.5 | 34.8 | 30.2 | 56 | 54 | 76 | 116.6 |
| monomer (SEC) [%] | 99 | 98 | 99 | >95 | >95 | >95 | >95 |
| monomer (CE-SDS) [%] | 99 | 99 | 99 | 98 | 98 | 98 | 96 |
| binding inhibition ANG2 tie2 receptor EC50 [nM] | | 5.4 | | | | | |
| T_agg [° C.] | | 63 | | | | 64 | 64 |
| T_m [° C.] | | 67 | | | | 67 | 67 |
| loss of ANG2 binding after 2 weeks incubation at pH 6.0 | | 0 | | | | 0 | 3 |
| loss of ANG2 binding after 2 weeks incubation at pH 7.4 | | 0 | | | | 1 | 3 |

TABLE 10

| | molecule | | | | | | |
|---|---|---|---|---|---|---|---|
| | 0074 | 0075 | 0076 | 0077 | 0090 | IgG | 0098 |
| format | CrossFab CL-CH1 | CrossFab CL-CH1 | CrossFab CL-CH1 | CrossFab CL-CH1 | CrossFab CL-CH1 | MAb | CrossMab CL-CH1 |
| valency for ANG2 | 1 | 1 | 1 | 1 | 1 | 2 | 2 |
| differences | VH: S100dP G100jA T28N T30A D100bS VL: wt | VH: S100dP G100jA T28N T30A D100bS VL: D50T | VH: D100bS VL: wt | VH: D100bS VL: D50T | VH: S100dP G100jA T28N T30A VL: D50T | reference molecule | VH: wt VL: wt |
| SEQ ID NOs: | HC: 48 LC: 49 | HC: 48 LC: 50 | HC: 74 LC: 49 | HC: 74 LC: 50 | HC: 47 LC: 50 | HC: 75 LC: 76 | HC: 51 LC: 49 |
| ka [1/Ms] | 2.27E+06 | 2.22E+06 | 1.06E+06 | 1.05E+06 | 2.16E+06 | | 1.56E+07 |
| kd [1/s] | 3.66E−02 | 3.10E−02 | 2.60E−01 | 2.58E−01 | 2.53E−03 | | 1.58E−04 |
| KD [nM] | 16 | 14 | 247 | 247 | 1 | | 0.01 |
| $t_{1/2}$ (s) | 19 | 22 | 3 | 3 | 274 | | 4381 |
| first purification step | kappa select | kappa select | kappa select | kappa select | kappa select | | MabSelectSuRe |
| scale [l] | 0.3 | 0.3 | 0.3 | 0.3 | 0.5 | | 1 |
| yield [mg/l supernatant] | 164 | 157 | 153.4 | 172.5 | 92 | | 302 |
| monomer (SEC) [%] | 67 | 70 | 72 | 79 | 80 | | |
| monomer (CE-SDS) [%] | 68 | 77 | 76 | 83 | 95 | | |
| further purification step(s) | SEC | SEC | SEC | SEC | SEC | | HIC + SEC |
| yield [mg/l supernatant] | 86.6 | 95 | 99 | 132 | 69 | | 42 |
| monomer (SEC) [%] | >98 | >98 | >98 | >98 | >98 | | >98 |
| monomer (CE-SDS) [%] | >99 | >99 | >99 | >99 | 99 | | 99 |
| binding inhibition ANG2 tie2 receptor EC50 [nM] | | 39 | | | 7 | 3.9 | 3.1 |
| T_agg [° C.] | | 64 | | | 64 | | |
| T_m [° C.] | | 67 | | | 67 | | |
| loss of ANG2 binding after 2 weeks incubation at pH 6.0 | | 0 | | | 0 | | |
| loss of ANG2 binding after 2 weeks incubation at pH 7.4 | | 0 | | | 0 | | |

TABLE 11

| | molecule | | | | | | |
|---|---|---|---|---|---|---|---|
| | 0099 | 0100 | 0101 | 0154 | 0155 | 0156 | 0157 |
| format | CrossMab CL-CH1 | CrossMab CL-CH1 | CrossMab CL-CH1 | CrossFab CL-CH1 | CrossFab CL-CH1 | CrossFab CL-CH1 | CrossFab CL-CH1 |
| valency for ANG2 | 2 | 2 | 2 | 1 | 1 | 1 | 1 |
| differences | VH: S100dP G100jA T28N T30A VL: wt | VH: S100dP G100jA T28N T30A VL: D50T | VH: S100dP G100jA T28N T30A D100bE VL: D50T | VH: wt VL: wt | VH: S100dP G100jA T28N T30A VL: D50T | VH: S100dP G100jA T28N T30A D100bS VL: D50T | VH: wt VL: D50T |
| SEQ ID NOs: | HC: 52 LC: 49 | HC: 52 LC: 50 | HC: 53 LC: 50 | HC: 46 LC: 77 | HC: 47 LC: 78 | HC: 48 LC: 78 | HC: 46 LC: 50 |
| ka [1/Ms] | 2.61E+07 | 2.06E+07 | 1.83E+07 | 8.48E+05 | 7.46E+05 | 6.75E+05 | 5.80E+05 |
| kd [1/s] | 1.10E−04 | 1.67E−04 | 1.20E−04 | 3.77E−02 | 3.19E−02 | 3.10E−03 | 2.32E−02 |
| KD [nM] | 0.004 | 0.008 | 0.007 | 44 | 43 | 5 | 40 |
| $t_{1/2}$ (s) | 6284 | 4156 | 5771 | 18 | 22 | 224 | 30 |
| first purification step | MabSelectSuRe | MabSelectSuRe | MabSelectSuRe | Capture select IgG-CH1 | Capture select IgG-CH1 | Capture select IgG-CH1 | Capture select IgG-CH1 |
| scale [l] | 1 | 1 | 1 | 0.3 | 0.3 | 0.3 | 0.3 |
| yield [mg/l supernatant] | 270 | 221 | 153 | 73.3 | 77.3 | 56.6 | 55.5 |
| monomer (SEC) [%] | 33 | 34 | | 68 | 64 | 77 | 64 |
| monomer (CE-SDS) [%] | | | 83 | 96 | 97 | 97 | 98 |
| further purification step(s) | HIC + SEC | HIC + SEC | HIC + SEC | SEC | SEC | SEC | SEC |
| yield [mg/l supernatant] | 52 | 78 | 74 | 33.8 | 36.1 | 28.2 | 31.7 |
| monomer (SEC) [%] | >98 | >98 | >99 | 96 | 95 | 96 | 96 |
| monomer (CE-SDS) [%] | 99 | 99 | 95 | 96 | 99 | 99.7 | >99 |
| binding inhibition ANG2 tie2 receptor EC50 [nM] | 3.2 | 3.2 | 3 | | | | |
| T_agg [° C.] | | | | 61 | 61 | 61 | 61 |
| T_m [° C.] | | | | 63 | 64 | 64 | 64 |
| loss of ANG2 binding after 2 weeks incubation at pH 6.0 | | | | | | | |
| loss of ANG2 binding after 2 weeks incubation at pH 7.4 | | | | | | | |

TABLE 12

| | molecule | | | | | |
|---|---|---|---|---|---|---|
| | 0162 | 0163 | 0164 | 0165 | 0166 | 0167 |
| format | CrossMab CL-CH1 | CrossMab CL-CH1 | CrossMab CL-CH1 | CrossMab CL-CH1 | CrossMab CL-CH1 | CrossMab CL-CH1 |
| valency for ANG2 | 1 | 1 | 1 | 1 | 1 | 1 |
| differences | reference molecule ANG2: wt1 VEGF: wt1 | ANG2: VH: S100dP G100jA T30A T28N VEGF: VH: wt1 VL: wt1 | ANG2: VH: S100dP G100jA T30A T28N VL: D100bS VL: D50T VEGF: VH: wt1 VL: wt1 | ANG2: VH: S100dP G100jA T30A T28N VL: D50T VEGF: VH: wt2 VL: wt2 | ANG2: VH: S100dP G100jA T30A T28N VL: D100bS VL: D50T VEGF: VH: wt2 VL: wt2 | reference molecule ANG2: wt2 VEGF: wt2 |
| SEQ ID NOs: | ANG2: HC: 79 LC: 80 VEGF: LC: 81 HC: 82 | ANG2: HC: 83 LC: 84 VEGF: LC: 81 HC: 82 | ANG2: HC: 85 LC: 86 VEGF: LC: 81 HC: 82 | ANG2: HC: 89 LC: 90 VEGF: HC: 87 LC: 88 | ANG2: HC: 91 LC: 92 VEGF: HC: 87 LC: 88 | ANG2: HC: 93 LC: 94 VEGF: HC: 87 LC: 88 |
| ka [1/Ms] | 3.65E+05 | 3.14E+05 | 2.76E+05 | 3.02E+05 | 2.75E+05 | 4.11E+05 |
| kd [1/s] | 1.56E−02 | 1.11E−03 | 1.08E−02 | 1.12E−03 | 1.35E−02 | 4.09E−02 |
| KD [nM] | 43 | 4 | 39 | 4 | 49 | 99 |
| $t_{1/2}$ (s) | 44 | 623 | 64 | 619 | 51 | 17 |
| first purification step | Capture select IgG-CH1 | Capture select IgG-CH1 | Capture select IgG-CH1 | Capture select IgG-CH1 | Capture select IgG-CH1 | Capture select IgG-CH1 |
| scale [l] | 0.4 | 0.4 | 0.4 | 0.4 | 0.4 | 0.4 |
| yield [mg/l supernatant] | 59.4 | 31.3 | 28.1 | 25 | 31.3 | 25 |
| monomer (SEC) [%] | 53 | 47 | 49 | 54 | 61 | 70 |
| monomer (CE-SDS) [%] | 65 | 58 | 57 | 59 | 63 | 62 |
| further purification step(s) | SEC + HIC + CEX | HIC + CEX | IEX | HIC + CEX | IEX | IEX |
| yield [mg/l supernatant] | 15.6 | 9.1 | 4.65 | 2.8 | 4.1 | 3.5 |
| monomer (SEC) [%] | 99 | 99 | 97 | 97 | 94 | 97 |
| monomer (CE-SDS) [%] | 98 | 99 | 96 | 96 | 93 | 97 |
| binding inhibition ANG2 tie2 receptor EC50 [nM] | | | | | | |
| T_agg [° C.] | 60 | 60 | 60 | 60 | 60 | 60 |

TABLE 12-continued

| | molecule | | | | | |
|---|---|---|---|---|---|---|
| | 0162 | 0163 | 0164 | 0165 | 0166 | 0167 |
| T_m [° C.] | 64 | 65 | 65 | 66 | 66 | 66 |
| loss of ANG2 binding after 2 weeks incubation at pH 6.0 | | | | | | |
| loss of ANG2 binding after 2 weeks incubation at pH 7.4 | | | | | | |

Aspects as reported herein are all the individual combinations of heavy chains and light chains as given in the Tables above.

One aspect as reported herein is a humanized anti-human ANG2 antibody comprising (a) a HVR-H1 comprising the amino acid sequence of SEQ ID NO: 29; (b) a HVR-H2 comprising the amino acid sequence of SEQ ID NO: 30; and (c) a HVR-H3 comprising the amino acid sequence of SEQ ID NO: 32. In one embodiment the antibody further comprises (d) a HVR-L1 comprising the amino acid sequence of SEQ ID NO: 34; (e) a HVR-L2 comprising the amino acid sequence of SEQ ID NO: 35; and (f) a HVR-L3 comprising the amino acid sequence of SEQ ID NO: 36.

One aspect as reported herein is a humanized anti-human ANG2 antibody comprising (a) a HVR-H1 comprising the amino acid sequence of SEQ ID NO: 29; (b) a HVR-H2 comprising the amino acid sequence of SEQ ID NO: 31; and (c) a HVR-H3 comprising the amino acid sequence of SEQ ID NO: 32. In one embodiment the antibody further comprises (d) a HVR-L1 comprising the amino acid sequence of SEQ ID NO: 34; (e) a HVR-L2 comprising the amino acid sequence of SEQ ID NO: 35; and (f) a HVR-L3 comprising the amino acid sequence of SEQ ID NO: 36.

In one aspect, the invention provides an anti-ANG2 antibody comprising at least one, two, three, four, five, or six HVRs selected from (a) a HVR-H1 comprising the amino acid sequence of SEQ ID NO: 29; (b) a HVR-H2 comprising the amino acid sequence of SEQ ID NO: 30; (c) a HVR-H3 comprising the amino acid sequence of SEQ ID NO: 32; (d) a HVR-L1 comprising the amino acid sequence of SEQ ID NO: 34; (e) a HVR-L2 comprising the amino acid sequence of SEQ ID NO: 35; and (f) a HVR-L3 comprising the amino acid sequence of SEQ ID NO: 36.

In one aspect, the invention provides an antibody comprising at least one, at least two, or all three VH HVR sequences selected from (a) a HVR-H1 comprising the amino acid sequence of SEQ ID NO: 29; (b) a HVR-H2 comprising the amino acid sequence of SEQ ID NO: 30; and (c) a HVR-H3 comprising the amino acid sequence of SEQ ID NO: 32. In one embodiment, the antibody comprises a HVR-H3 comprising the amino acid sequence of SEQ ID NO: 32. In another embodiment, the antibody comprises a HVR-H3 comprising the amino acid sequence of SEQ ID NO: 32 and a HVR-L3 comprising the amino acid sequence of SEQ ID NO: 36. In a further embodiment, the antibody comprises a HVR-H3 comprising the amino acid sequence of SEQ ID NO: 32, a HVR-L3 comprising the amino acid sequence of SEQ ID NO: 36, and a HVR-H2 comprising the amino acid sequence of SEQ ID NO: 30. In a further embodiment, the antibody comprises (a) a HVR-H1 comprising the amino acid sequence of SEQ ID NO: 29; (b) a HVR-H2 comprising the amino acid sequence of SEQ ID NO: 30; and (c) a HVR-H3 comprising the amino acid sequence of SEQ ID NO: 32.

In another aspect, the invention provides an antibody comprising at least one, at least two, or all three VL HVR sequences selected from (a) a HVR-L1 comprising the amino acid sequence of SEQ ID NO: 34; (b) a HVR-L2 comprising the amino acid sequence of SEQ ID NO: 35; and (c) a HVR-L3 comprising the amino acid sequence of SEQ ID NO: 36. In one embodiment, the antibody comprises (a) a HVR-L1 comprising the amino acid sequence of SEQ ID NO: 34; (b) a HVR-L2 comprising the amino acid sequence of SEQ ID NO: 35; and (c) a HVR-L3 comprising the amino acid sequence of SEQ ID NO: 36.

In another aspect, an antibody of the invention comprises (a) a VH domain comprising at least one, at least two, or all three VH HVR sequences selected from (i) a HVR-H1 comprising the amino acid sequence of SEQ ID NO: 29, (ii) a HVR-H2 comprising the amino acid sequence of SEQ ID NO: 30, and (iii) a HVR-H3 comprising an amino acid sequence selected from SEQ ID NO: 32; and (b) a VL domain comprising at least one, at least two, or all three VL HVR sequences selected from (i) a HVR-L1 comprising the amino acid sequence of SEQ ID NO: 34, (ii) a HVR-L2 comprising the amino acid sequence of SEQ ID NO: 35, and (c) a HVR-L3 comprising the amino acid sequence of SEQ ID NO: 36.

In another aspect, the invention provides an antibody comprising (a) a HVR-H1 comprising the amino acid sequence of SEQ ID NO: 29; (b) a HVR-H2 comprising the amino acid sequence of SEQ ID NO: 31; (c) a HVR-H3 comprising the amino acid sequence of SEQ ID NO: 32; (d) a HVR-L1 comprising the amino acid sequence of SEQ ID NO: 34; (e) a HVR-L2 comprising the amino acid sequence of SEQ ID NO: 35; and (f) a HVR-L3 comprising an amino acid sequence selected from SEQ ID NO: 36.

In another aspect, an anti-ANG2 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 28. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-ANG2 antibody comprising that sequence retains the ability to bind to ANG2. In certain embodiments, a total of 1 to 10 amino acids have been substituted, inserted and/or deleted in SEQ ID NO: 28. In certain embodiments, substitutions, insertions, or deletions occur in regions outside the HVRs (i.e., in the FRs). Optionally, the anti-ANG2 antibody comprises the VH sequence in SEQ ID NO: 28, including post-translational modifications of that sequence. In a particular embodiment, the VH comprises one, two or three HVRs selected from: (a) HVR-H1 comprising the amino acid sequence of SEQ ID NO: 29, (b) HVR-H2 comprising the amino acid sequence of SEQ ID NO: 30, and (c) HVR-H3 comprising the amino acid sequence of SEQ ID NO: 32.

In another aspect, an anti-ANG2 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 33. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-ANG2 antibody comprising that sequence retains the ability to bind to ANG2. In certain embodiments, a total of 1 to 10 amino acids have been substituted, inserted and/or deleted in SEQ ID NO: 33. In certain embodiments, the substitutions, insertions, or deletions occur in regions outside the HVRs (i.e., in the FRs). Optionally, the anti-ANG2 antibody comprises the VL sequence in SEQ ID NO: 33, including post-translational modifications of that sequence. In a particular embodiment, the VL comprises one, two or three HVRs selected from (a) HVR-L1 comprising the amino acid sequence of SEQ ID NO: 34; (b) HVR-L2 comprising the amino acid sequence of SEQ ID NO: 35; and (c) HVR-L3 comprising the amino acid sequence of SEQ ID NO: 36.

In another aspect, an anti-ANG2 antibody is provided, wherein the antibody comprises a VH as in any of the embodiments provided above, and a VL as in any of the embodiments provided above. In one embodiment, the antibody comprises the VH and VL sequences in SEQ ID NO: 28 and SEQ ID NO: 33, respectively, including post-translational modifications of those sequences.

In a further aspect of the invention, an anti-ANG2 antibody according to any of the above embodiments is a monoclonal antibody. In one embodiment, an anti-ANG2 antibody is an antibody fragment, e.g., an Fv, Fab, Fab', scFv, diabody, or F(ab')$_2$ fragment. In another embodiment, the antibody is a full length antibody, e.g., an intact IgG1 antibody or other antibody class or isotype as defined herein.

In one embodiment of all aspects as reported herein the anti-ANG2 antibody is an effector silent anti-ANG2 antibody. In one embodiment of all aspects as reported herein the anti-ANG2 antibody is an effector silent anti-ANG2 antibody and does not bind to human FcRn. In one embodiment of all aspects as reported herein is the anti-ANG2 antibody of the human subclass IgG1 and has the mutations L234A, L235A, P329G, I253A, H310A and H434A in both heavy chains (numbering according to the Kabat index).

In one embodiment of all aspects as reported herein the anti-ANG2 antibody is a bispecific antibody.

One aspect as reported herein is a bivalent, bispecific antibody comprising a) a first light chain and a first heavy chain of an antibody specifically binding to a first antigen, and
b) a second light chain and a second heavy chain of an antibody specifically binding to a second antigen, wherein the variable domains VL and VH of the second light chain and the second heavy chain are replaced by each other, wherein the first antigen or the second antigen is human ANG2.

The antibody under a) does not contain a modification as reported under b) and the heavy chain and the light chain under a) are isolated chains.

In the antibody under b)
within the light chain
the variable light chain domain VL is replaced by the variable heavy chain domain VH of said antibody,
and
within the heavy chain
the variable heavy chain domain VH is replaced by the variable light chain domain VL of said antibody.

In one embodiment
i) in the constant domain CL of the first light chain under a) the amino acid at position 124 (numbering according to Kabat) is substituted by a positively charged amino acid, and wherein in the constant domain CH1 of the first heavy chain under a) the amino acid at position 147 or the amino acid at position 213 (numbering according to Kabat EU index) is substituted by a negatively charged amino acid,
or
ii) in the constant domain CL of the second light chain under b) the amino acid at position 124 (numbering according to Kabat) is substituted by a positively charged amino acid, and wherein in the constant domain CH1 of the second heavy chain under b) the amino acid at position 147 or the amino acid at position 213 (numbering according to Kabat EU index) is substituted by a negatively charged amino acid.

In one preferred embodiment
i) in the constant domain CL of the first light chain under a) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the first heavy chain under a) the amino acid at position 147 or the amino acid at position 213 is substituted independently by glutamic acid (E) or aspartic acid (D) (numbering according to Kabat EU index),
or
ii) in the constant domain CL of the second light chain under b) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the second heavy chain under b) the amino acid at position 147 or the amino acid at position 213 is substituted independently by glutamic acid (E) or aspartic acid (D) (numbering according to Kabat EU index).

In one embodiment in the constant domain CL of the second heavy chain the amino acids at position 124 and 123 are substituted by K (numbering according to Kabat EU index).

In one embodiment in the constant domain CH1 of the second light chain the amino acids at position 147 and 213 are substituted by E (numbering according to EU index of Kabat).

In one preferred embodiment in the constant domain CL of the first light chain the amino acids at position 124 and 123 are substituted by K, and in the constant domain CH1 of the first heavy chain the amino acids at position 147 and 213 are substituted by E (numbering according to Kabat EU index).

In one embodiment in the constant domain CL of the second heavy chain the amino acids at position 124 and 123 are substituted by K, and wherein in the constant domain CH1 of the second light chain the amino acids at position 147 and 213 are substituted by E, and in the variable domain VL of the first light chain the amino acid at position 38 is substituted by K, in the variable domain VH of the first heavy chain the amino acid at position 39 is substituted by E, in the variable domain VL of the second heavy chain the amino acid at position 38 is substituted by K, and in the variable domain VH of the second light chain the amino acid at position 39 is substituted by E (numbering according to Kabat EU index).

One aspect as reported herein is a bivalent, bispecific antibody comprising
  a) a first light chain and a first heavy chain of an antibody specifically binding to a first antigen, and
  b) a second light chain and a second heavy chain of an antibody specifically binding to a second antigen, wherein the variable domains VL and VH of the second light chain and the second heavy chain are replaced by each other, and wherein the constant domains CL and CH1 of the second light chain and the second heavy chain are replaced by each other,
  wherein the first antigen or the second antigen is human ANG2.

The antibody under a) does not contain a modification as reported under b) and the heavy chain and the light chain and a) are isolated chains.

In the antibody under b)
  within the light chain
    the variable light chain domain VL is replaced by the variable heavy chain domain VH of said antibody, and the constant light chain domain CL is replaced by the constant heavy chain domain CH1 of said antibody;
  and
  within the heavy chain
    the variable heavy chain domain VH is replaced by the variable light chain domain VL of said antibody, and the constant heavy chain domain CH1 is replaced by the constant light chain domain CL of said antibody.

One aspect as reported herein is a bivalent, bispecific antibody comprising
  a) a first light chain and a first heavy chain of an antibody specifically binding to a first antigen, and
  b) a second light chain and a second heavy chain of an antibody specifically binding to a second antigen, wherein the constant domains CL and CH1 of the second light chain and the second heavy chain are replaced by each other,
  wherein the first antigen or the second antigen is human ANG2.

The antibody under a) does not contain a modification as reported under b) and the heavy chain and the light chain under a) are isolated chains.

In the antibody under b)
  within the light chain
    the constant light chain domain CL is replaced by the constant heavy chain domain CH1 of said antibody;
  and within the heavy chain
    the constant heavy chain domain CH1 is replaced by the constant light chain domain CL of said antibody.

One aspect as reported herein is a multispecific antibody comprising
  a) a full length antibody specifically binding to a first antigen and consisting of two antibody heavy chains and two antibody light chains, and
  b) one, two, three or four single chain Fab fragments specifically binding to one to four further antigens (i.e. a second and/or third and/or fourth and/or fifth antigen, preferably specifically binding to one further antigen, i.e. a second antigen),
  wherein said single chain Fab fragments under b) are fused to said full length antibody under a) via a peptidic linker at the C- or N-terminus of the heavy or light chain of said full length antibody,
  wherein the first antigen or one of the further antigens is human ANG2.

In one embodiment one or two identical single chain Fab fragments binding to a second antigen are fused to said full length antibody via a peptidic linker at the C-terminus of the heavy or light chains of said full length antibody.

In one embodiment one or two identical single chain Fab fragments binding to a second antigen are fused to said full length antibody via a peptidic linker at the C-terminus of the heavy chains of said full length antibody.

In one embodiment one or two identical single chain Fab fragments binding to a second antigen are fused to said full length antibody via a peptidic linker at the C-terminus of the light chains of said full length antibody.

In one embodiment two identical single chain Fab fragments binding to a second antigen are fused to said full length antibody via a peptidic linker at the C-terminus of each heavy or light chain of said full length antibody.

In one embodiment two identical single chain Fab fragments binding to a second antigen are fused to said full length antibody via a peptidic linker at the C-terminus of each heavy chain of said full length antibody.

In one embodiment two identical single chain Fab fragments binding to a second antigen are fused to said full length antibody via a peptidic linker at the C-terminus of each light chain of said full length antibody.

One aspect as reported herein is a trivalent, bispecific antibody comprising
  a) a full length antibody specifically binding to a first antigen and consisting of two antibody heavy chains and two antibody light chains,
  b) a first polypeptide consisting of
    ba) an antibody heavy chain variable domain (VH), or
    bb) an antibody heavy chain variable domain (VH) and an antibody constant domain 1 (CH1),
    wherein said first polypeptide is fused with the N-terminus of its VH domain via a peptidic linker to the C-terminus of one of the two heavy chains of said full length antibody,
  c) a second polypeptide consisting of
    ca) an antibody light chain variable domain (VL), or
    cb) an antibody light chain variable domain (VL) and an antibody light chain constant domain (CL), wherein said second polypeptide is fused with the N-terminus of the VL domain via a peptidic linker to the C-terminus of the other of the two heavy chains of said full length antibody,
and
wherein the antibody heavy chain variable domain (VH) of the first polypeptide and the antibody light chain variable domain (VL) of the second polypeptide together form an antigen-binding site specifically binding to a second antigen,
and
wherein the first antigen or the second antigen is human ANG2.

In one embodiment the antibody heavy chain variable domain (VH) of the polypeptide under b) and the antibody light chain variable domain (VL) of the polypeptide under c) are linked and stabilized via an interchain disulfide bridge by introduction of a disulfide bond between the following positions:
  i) heavy chain variable domain position 44 to light chain variable domain position 100, or
  ii) heavy chain variable domain position 105 to light chain variable domain position 43, or
  iii) heavy chain variable domain position 101 to light chain variable domain position 100 (numbering always according to Kabat EU index).

Techniques to introduce unnatural disulfide bridges for stabilization are described e.g. in WO 94/029350, Rajagopal, V., et al., Prot. Eng. (1997) 1453-59; Kobayashi, H., et al., Nuclear Medicine & Biology, Vol. 25, (1998) 387-393; or Schmidt, M., et al., Oncogene (1999) 18 1711-1721. In one embodiment the optional disulfide bond between the variable domains of the polypeptides under b) and c) is between heavy chain variable domain position 44 and light chain variable domain position 100. In one embodiment the optional disulfide bond between the variable domains of the polypeptides under b) and c) is between heavy chain variable domain position 105 and light chain variable domain position 43. (numbering always according to EU index of Kabat) In one embodiment a trivalent, bispecific antibody without said optional disulfide stabilization between the variable domains VH and VL of the single chain Fab fragments is preferred.

One aspect as reported herein is a trispecific or tetraspecific antibody, comprising
  a) a first light chain and a first heavy chain of a full length antibody which specifically binds to a first antigen, and
  b) a second (modified) light chain and a second (modified) heavy chain of a full length antibody which specifically binds to a second antigen, wherein the variable domains VL and VH are replaced by each other, and/or wherein the constant domains CL and CH1 are replaced by each other, and
  c) wherein one to four antigen binding peptides which specifically bind to one or two further antigens (i.e. to a third and/or fourth antigen) are fused via a peptidic linker to the C- or N-terminus of the light chains or heavy chains of a) and/or b),
  wherein the first antigen or the second antigen or one of the further antigens is human ANG2.

The antibody under a) does not contain a modification as reported under b) and the heavy chain and the light chain and a) are isolated chains.

In one embodiment the trispecific or tetraspecific antibody comprises under c) one or two antigen binding peptides which specifically bind to one or two further antigens.

In one embodiment the antigen binding peptides are selected from the group of a scFv fragment and a scFab fragment.

In one embodiment the antigen binding peptides are scFv fragments.

In one embodiment the antigen binding peptides are scFab fragments.

In one embodiment the antigen binding peptides are fused to the C-terminus of the heavy chains of a) and/or b).

In one embodiment the trispecific or tetraspecific antibody comprises under c) one or two antigen binding peptides which specifically bind to one further antigen.

In one embodiment the trispecific or tetraspecific antibody comprises under c) two identical antigen binding peptides which specifically bind to a third antigen. In one preferred embodiment such two identical antigen binding peptides are fused both via the same peptidic linker to the C-terminus of the heavy chains of a) and b). In one preferred embodiment the two identical antigen binding peptides are either a scFv fragment or a scFab fragment.

In one embodiment the trispecific or tetraspecific antibody comprises under c) two antigen binding peptides which specifically bind to a third and a fourth antigen. In one embodiment said two antigen binding peptides are fused both via the same peptide connector to the C-terminus of the heavy chains of a) and b). In one preferred embodiment said two antigen binding peptides are either a scFv fragment or a scFab fragment.

One aspect as reported herein is a bispecific, tetravalent antibody comprising
  a) two light chains and two heavy chains of an antibody, which specifically bind to a first antigen (and comprise two Fab fragments),
  b) two additional Fab fragments of an antibody, which specifically bind to a second antigen, wherein said additional Fab fragments are fused both via a peptidic linker either to the C- or N-termini of the heavy chains of a),
  and
  wherein in the Fab fragments the following modifications were performed
    i) in both Fab fragments of a), or in both Fab fragments of b), the variable domains VL and VH are replaced by each other, and/or the constant domains CL and CH1 are replaced by each other,
    or
    ii) in both Fab fragments of a) the variable domains VL and VH are replaced by each other, and the constant domains CL and CH1 are replaced by each other,
    and
    in both Fab fragments of b) the variable domains VL and VH are replaced by each other, or the constant domains CL and CH1 are replaced by each other,
    or
    iii) in both Fab fragments of a) the variable domains VL and VH are replaced by each other, or the constant domains CL and CH1 are replaced by each other,
    and
    in both Fab fragments of b) the variable domains VL and VH are replaced by each other, and the constant domains CL and CH1 are replaced by each other,
    or
    iv) in both Fab fragments of a) the variable domains VL and VH are replaced by each other, and in both Fab fragments of b) the constant domains CL and CH1 are replaced by each other, or v) in both Fab fragments of a) the constant domains CL and CH1 are replaced by each other, and in both Fab fragments of b) the variable domains VL and VH are replaced by each other, wherein the first antigen or the second antigen is human ANG2.

In one embodiment said additional Fab fragments are fused both via a peptidic linker either to the C-termini of the heavy chains of a), or to the N-termini of the heavy chains of a).

In one embodiment said additional Fab fragments are fused both via a peptidic linker either to the C-termini of the heavy chains of a).

In one embodiment said additional Fab fragments are fused both via a peptide connector to the N-termini of the heavy chains of a).

In one embodiment in the Fab fragments the following modifications are performed:
i) in both Fab fragments of a), or in both Fab fragments of b), the variable domains VL and VH are replaced by each other,
and/or
the constant domains CL and CH1 are replaced by each other.

In one embodiment in the Fab fragments the following modifications are performed:
i) in both Fab fragments of a) the variable domains VL and VH are replaced by each other,
and/or
the constant domains CL and CH1 are replaced by each other.

In one embodiment in the Fab fragments the following modifications are performed:
i) in both Fab fragments of a) the constant domains CL and CH1 are replaced by each other.

In one embodiment in the Fab fragments the following modifications are performed:
i) in both Fab fragments of b) the variable domains VL and VH are replaced by each other,
and/or
the constant domains CL and CH1 are replaced by each other.

In one embodiment in the Fab fragments the following modifications are performed:
i) in both Fab fragments of b) the constant domains CL and CH1 are replaced by each other.

One aspect as reported herein is a bispecific, tetravalent antibody comprising:
a) a (modified) heavy chain of a first antibody, which specifically binds to a first antigen and comprises a first VH—CH1 domain pair, wherein to the C-terminus of said heavy chain the N-terminus of a second VH—CH1 domain pair of said first antibody is fused via a peptidic linker,
b) two light chains of said first antibody of a),
c) a (modified) heavy chain of a second antibody, which specifically binds to a second antigen and comprises a first VH-CL domain pair, wherein to the C-terminus of said heavy chain the N-terminus of a second VH-CL domain pair of said second antibody is fused via a peptidic linker, and
d) two (modified) light chains of said second antibody of c), each comprising a CL-CH1 domain pair,
wherein the first antigen or the second antigen is human ANG2.

One aspect as reported herein is a bispecific antibody comprising
a) the heavy chain and the light chain of a first full length antibody that specifically binds to a first antigen, and
b) the heavy chain and the light chain of a second full length antibody that specifically binds to a second antigen, wherein the N-terminus of the heavy chain is connected to the C-terminus of the light chain via a peptidic linker,
wherein the first antigen or the second antigen is human ANG2.

The antibody under a) does not contain a modification as reported under b) and the heavy chain and the light chain are isolated chains.

One aspect as reported herein is a bispecific antibody comprising
a) a full length antibody specifically binding to a first antigen and consisting of two antibody heavy chains and two antibody light chains, and
b) an Fv fragment specifically binding to a second antigen comprising a $VH^2$ domain and a $VL^2$ domain, wherein both domains are connected to each other via a disulfide bridge,
wherein only either the $VH^2$ domain or the $VL^2$ domain is fused via a peptidic linker to the heavy or light chain of the full length antibody specifically binding to a first antigen,
wherein the first antigen or the second antigen is human ANG2.

In the bispecific the heavy chains and the light chains under a) are isolated chains.

In one embodiment the other of the $VH^2$ domain or the $VL^2$ domain is not fused via a peptide linker to the heavy or light chain of the full length antibody specifically binding to a first antigen.

In all aspects as reported herein the first light chain comprises a VL domain and a CL domain and the first heavy chain comprises a VH domain, a CH1 domain, a hinge region, a CH2 domain and a CH3 domain.

In one embodiment of all aspects the antibody as reported herein is a multispecific antibody, which requires heterodimerization of at least two heavy chain polypeptides, and wherein the antibody specifically binds to human ANG2 and a second non-human ANG2 antigen.

Several approaches for CH3-modifications in order to support heterodimerization have been described, for example in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291, which are herein included by reference. Typically, in the approaches known in the art, the CH3 domain of the first heavy chain and the CH3 domain of the second heavy chain are both engineered in a complementary manner so that the heavy chain comprising one engineered CH3 domain can no longer homodimerize with another heavy chain of the same structure (e.g. a CH3-engineered first heavy chain can no longer homodimerize with another CH3-engineered first heavy chain; and a CH3-engineered second heavy chain can no longer homodimerize with another CH3-engineered second heavy chain). Thereby the heavy chain comprising one engineered CH3 domain is forced to heterodimerize with another heavy chain comprising the CH3 domain, which is engineered in a complementary manner. For this embodiment of the invention, the CH3 domain of the first heavy chain and the CH3 domain of the second heavy chain are engineered in a complementary manner by amino acid substitutions, such that the first heavy chain and the second heavy chain are forced to heterodimerize, whereas the first heavy chain and the second heavy chain can no longer homodimerize (e.g. for steric reasons).

The different approaches for supporting heavy chain heterodimerization known in the art, that were cited and included above, are contemplated as different alternatives used in a multispecific antibody according to the invention, which comprises a "non-crossed Fab region" derived from a first antibody, which specifically binds to a first antigen, and a "crossed Fab region" derived from a second antibody, which specifically binds to a second antigen, in combination with the particular amino acid substitutions described above for the invention.

The CH3 domains of the multispecific antibody as reported herein can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

In one preferred embodiment the multispecific antibody as reported herein comprises a T366W mutation in the CH3 domain of the "knobs chain" and T366S, L368A, Y407V mutations in the CH3 domain of the "hole-chain" (numbering according to Kabat EU index). An additional interchain disulfide bridge between the CH3 domains can also be used (Merchant, A. M., et al., Nature Biotech. 16 (1998) 677-681) e.g. by introducing a Y349C mutation into the CH3 domain of the "knobs chain" and a E356C mutation or a S354C mutation into the CH3 domain of the "hole chain". Thus in a another preferred embodiment, the multispecific antibody as reported herein comprises the Y349C and T366W mutations in one of the two CH3 domains and the E356C, T366S, L368A and Y407V mutations in the other of the two CH3 domains or the multispecific antibody as reported herein comprises the Y349C and T366W mutations in one of the two CH3 domains and the S354C, T366S, L368A and Y407V mutations in the other of the two CH3 domains (the additional Y349C mutation in one CH3 domain and the additional E356C or S354C mutation in the other CH3 domain forming a interchain disulfide bridge) (numbering according to Kabat EU index).

But also other knobs-in-holes technologies as described by EP 1 870 459A1, can be used alternatively or additionally. In one embodiment the multispecific antibody as reported herein comprises the R409D and K370E mutations in the CH3 domain of the "knobs chain" and the D399K and E357K mutations in the CH3 domain of the "hole-chain" (numbering according to Kabat EU index).

In one embodiment the multispecific antibody as reported herein comprises a T366W mutation in the CH3 domain of the "knobs chain" and the T366S, L368A and Y407V mutations in the CH3 domain of the "hole chain" and additionally the R409D and K370E mutations in the CH3 domain of the "knobs chain" and the D399K and E357K mutations in the CH3 domain of the "hole chain" (numbering according to the Kabat EU index).

In one embodiment the multispecific antibody as reported herein comprises the Y349C and T366W mutations in one of the two CH3 domains and the S354C, T366S, L368A and Y407V mutations in the other of the two CH3 domains, or the multispecific antibody as reported herein comprises the Y349C and T366W mutations in one of the two CH3 domains and the S354C, T366S, L368A and Y407V mutations in the other of the two CH3 domains and additionally the R409D and K370E mutations in the CH3 domain of the "knobs chain" and the D399K and E357K mutations in the CH3 domain of the "hole chain" (numbering according to the Kabat EU index).

Apart from the "knob-into-hole technology" other techniques for modifying the CH3 domains of the heavy chains of a multispecific antibody to enforce heterodimerization are known in the art. These technologies, especially the ones described in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954 and WO 2013/096291 are contemplated herein as alternatives to the "knob-into-hole technology" in combination with a multispecific antibody as reported herein.

In one embodiment of a multispecific antibody as reported herein the approach described in EP 1870459 is used to support heterodimerization of the first heavy chain and the second heavy chain of the multispecific antibody. This approach is based on the introduction of charged amino acids with opposite charges at specific amino acid positions in the CH3/CH3-domain-interface between both, the first and the second heavy chain.

Accordingly, this embodiment relates to a multispecific antibody as reported herein, wherein in the tertiary structure of the antibody the CH3 domain of the first heavy chain and the CH3 domain of the second heavy chain form an interface that is located between the respective antibody CH3 domains, wherein the respective amino acid sequences of the CH3 domain of the first heavy chain and the CH3 domain of the second heavy chain each comprise a set of amino acids that is located within said interface in the tertiary structure of the antibody, wherein from the set of amino acids that is located in the interface in the CH3 domain of one heavy chain a first amino acid is substituted by a positively charged amino acid and from the set of amino acids that is located in the interface in the CH3 domain of the other heavy chain a second amino acid is substituted by a negatively charged amino acid. The multispecific antibody according to this embodiment is herein also referred to as "CH3(+/−)-engineered multispecific antibody" (wherein the abbreviation "+/−" stands for the oppositely charged amino acids that were introduced in the respective CH3 domains).

In one embodiment of said CH3(+/−)-engineered multispecific antibody as reported herein the positively charged amino acid is selected from K, R and H, and the negatively charged amino acid is selected from E or D.

In one embodiment of said CH3(+/−)-engineered multispecific antibody as reported herein the positively charged amino acid is selected from K and R, and the negatively charged amino acid is selected from E or D.

In one embodiment of said CH3(+/−)-engineered multispecific antibody as reported herein the positively charged amino acid is K, and the negatively charged amino acid is E.

In one embodiment of said CH3(+/−)-engineered multispecific antibody as reported herein in the CH3 domain of one heavy chain the amino acid R at position 409 is substituted by D and the amino acid K at position is substituted by E, and in the CH3 domain of the other heavy chain the amino acid D at position 399 is substituted by K and the amino acid E at position 357 is substituted by K (numbering according to Kabat EU index).

In one embodiment of a multispecific antibody as reported herein the approach described in WO 2013/157953 is used to support heterodimerization of the first heavy chain and the second heavy chain of the multispecific antibody. In one embodiment of said multispecific antibody as reported herein, in the CH3 domain of one heavy chain the amino acid T at position 366 is substituted by K, and in the CH3 domain of the other heavy chain the amino acid L at position 351 is substituted by D (numbering according to Kabat EU index). In another embodiment of said multispecific antibody as reported herein, in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index).

In another embodiment of said multispecific antibody as reported herein, in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index). Additionally at least one of the following substitutions is comprised in the CH3 domain of the other heavy chain: the amino acid Y at position 349 is substituted by E, the amino acid Y at position 349 is substituted by D and the amino acid L at position 368 is substituted by E (numbering according to Kabat EU index). In one embodiment the amino acid L at position 368 is substituted by E (numbering according to Kabat EU index).

In one embodiment of a multispecific antibody as reported herein the approach described in WO 2012/058768 is used to support heterodimerization of the first heavy chain and the second heavy chain of the multispecific antibody. In one embodiment of said multispecific antibody as reported herein, in the CH3 domain of one heavy chain the amino acid L at position 351 is substituted by Y and the amino acid Y at position 407 is substituted by A, and in the CH3 domain of the other heavy chain the amino acid T at position 366 is substituted by A and the amino acid K at position 409 is substituted by F (numbering according to Kabat EU index). In another embodiment, in addition to the aforementioned substitutions, in the CH3 domain of the other heavy chain at least one of the amino acids at positions 411 (originally T), 399 (originally D), 400 (originally S), 405 (originally F), 390 (originally N) and 392 (originally K) is substituted (numbering according to Kabat EU index). Preferred substitutions are:
substituting the amino acid T at position 411 by an amino acid selected from N, R, Q, K, D, E and W (numbering according to Kabat EU index),
substituting the amino acid D at position 399 by an amino acid selected from R, W, Y, and K (numbering according to Kabat EU index),
substituting the amino acid S at position 400 by an amino acid selected from E, D, R and K (numbering according to Kabat EU index),
substituting the amino acid F at position 405 by an amino acid selected from I, M, T, S, V and W (numbering according to Kabat EU index;
substituting the amino acid N at position 390 by an amino acid selected from R, K and D (numbering according to Kabat EU index; and
substituting the amino acid K at position 392 by an amino acid selected from V, M, R, L, F and E (numbering according to Kabat EU index).

In another embodiment of said multispecific antibody as reported herein (engineered according to WO 2012/058768), in the CH3 domain of one heavy chain the amino acid L at position 351 is substituted by Y and the amino acid Y at position 407 is substituted by A, and in the CH3 domain of the other heavy chain the amino acid T at position 366 is substituted by V and the amino acid K at position 409 is substituted by F (numbering according to Kabat EU index). In another embodiment of said multispecific antibody as reported herein, in the CH3 domain of one heavy chain the amino acid Y at position 407 is substituted by A, and in the CH3 domain of the other heavy chain the amino acid T at position 366 is substituted by A and the amino acid K at position 409 is substituted by F (numbering according to Kabat EU index). In said last aforementioned embodiment, in the CH3 domain of said other heavy chain the amino acid K at position 392 is substituted by E, the amino acid T at position 411 is substituted by E, the amino acid D at position 399 is substituted by R and the amino acid S at position 400 is substituted by R (numbering according to Kabat EU index).

In one embodiment of a multispecific antibody as reported herein the approach described in WO 2011/143545 is used to support heterodimerization of the first heavy chain and the second heavy chain of the multispecific antibody. In one embodiment of said multispecific antibody as reported herein, amino acid modifications in the CH3 domains of both heavy chains are introduced at positions 368 and/or 409 (numbering according to Kabat EU index).

In one embodiment of a multispecific antibody as reported herein the approach described in WO 2011/090762 is used to support heterodimerization of the first heavy chain and the second heavy chain of the multispecific antibody. WO 2011/090762 relates to amino acid modifications according to the "knob-into-hole" technology. In one embodiment of said CH3(KiH)-engineered multispecific antibody as reported herein, in the CH3 domain of one heavy chain the amino acid T at position 366 is substituted by W, and in the CH3 domain of the other heavy chain the amino acid Y at position 407 is substituted by A (numbering according to Kabat EU index). In another embodiment of said CH3 (KiH)-engineered multispecific antibody as reported herein, in the CH3 domain of one heavy chain the amino acid T at position 366 is substituted by Y, and in the CH3 domain of the other heavy chain the amino acid Y at position 407 is substituted by T (numbering according to Kabat EU index).

In one embodiment of a multispecific antibody as reported herein, which is of IgG2 isotype, the approach described in WO 2011/090762 is used to support heterodimerization of the first heavy chain and the second heavy chain of the multispecific antibody.

In one embodiment of a multispecific antibody as reported herein, the approach described in WO 2009/089004 is used to support heterodimerization of the first heavy chain and the second heavy chain of the multispecific antibody. In one embodiment of said multispecific antibody as reported herein, in the CH3 domain of one heavy chain the amino acid K or N at position 392 is substituted by a negatively charged amino acid (in one preferred embodiment by E or D, in one preferred embodiment by D), and in the CH3 domain of the other heavy chain the amino acid D at position 399 the amino acid E or D at position 356 or the amino acid E at position 357 is substituted by a positively charged amino acid (in one preferred embodiment K or R, in one preferred embodiment by K, in one preferred embodiment the amino acids at positions 399 or 356 are substituted by K) (numbering according to Kabat EU index). In one further embodiment, in addition to the aforementioned substitutions, in the CH3 domain of the one heavy chain the amino acid K or R at position 409 is substituted by a negatively charged amino acid (in one preferred embodiment by E or D, in one preferred embodiment by D) (numbering according to Kabat EU index). In one even further embodiment, in addition to or alternatively to the aforementioned substitutions, in the CH3 domain of the one heavy chain the amino acid K at position 439 and/or the amino acid K at position 370 is substituted independently from each other by a negatively charged amino acid (in one preferred embodiment by E or D, in one preferred embodiment by D) (numbering according to Kabat EU index).

In one embodiment of a multispecific antibody as reported herein, the approach described in WO 2007/147901 is used to support heterodimerization of the first heavy chain and the second heavy chain of the multispecific antibody. In one embodiment of said multispecific antibody as reported herein, in the CH3 domain of one heavy chain the amino acid K at position 253 is substituted by E, the amino acid D at position 282 is substituted by K and the amino acid K at position 322 is substituted by D, and in the CH3 domain of the other heavy chain the amino acid D at position 239 is substituted by K, the amino acid E at position 240 is substituted by K and the amino acid K at position 292 is substituted by D (numbering according to Kabat EU index).

In one embodiment of a multispecific antibody as reported herein, the approach described in WO 2007/110205 is used to support heterodimerization of the first heavy chain and the second heavy chain of the multispecific antibody.

In one embodiment of all aspects and embodiments as reported herein the multispecific antibody is a bispecific antibody or a trispecific antibody. In one preferred embodiment of the invention the multispecific antibody is a bispecific antibody.

In one embodiment of all aspects as reported herein, the antibody is a bivalent or trivalent antibody. In one embodiment the antibody is a bivalent antibody.

In one embodiment of all aspects as reported herein, the multispecific antibody has a constant domain structure of an IgG type antibody. In one further embodiment of all aspects as reported herein, the multispecific antibody is characterized in that said multispecific antibody is of human subclass IgG1, or of human subclass IgG1 with the mutations L234A and L235A. In one further embodiment of all aspects as reported herein, the multispecific antibody is characterized in that said multispecific antibody is of human subclass IgG2. In one further embodiment of all aspects as reported herein, the multispecific antibody is characterized in that said multispecific antibody is of human subclass IgG3. In one further embodiment of all aspects as reported herein, the multispecific antibody is characterized in that said multispecific antibody is of human subclass IgG4 or, of human subclass IgG4 with the additional mutation S228P. In one further embodiment of all aspects as reported herein, the multispecific antibody is characterized in that said multispecific antibody is of human subclass IgG1 or human subclass IgG4. In one further embodiment of all aspects as reported herein, the multispecific antibody is characterized in that said multispecific antibody is of human subclass IgG1 with the mutations L234A and L235A (numbering according to Kabat EU index). In one further embodiment of all aspects as reported herein, the multispecific antibody is characterized in that said multispecific antibody is of human subclass IgG1 with the mutations L234A, L235A and P329G (numbering according to Kabat EU index). In one further embodiment of all aspects as reported herein, the multispecific antibody is characterized in that said multispecific antibody is of human subclass IgG4 with the mutations S228P and L235E (numbering according to Kabat EU index). In one further embodiment of all aspects as reported herein, the multispecific antibody is characterized in that said multispecific antibody is of human subclass IgG4 with the mutations S228P, L235E and P329G (numbering according to Kabat EU index).

In one embodiment of all aspects as reported herein, an antibody comprising a heavy chain including a CH3 domain as specified herein, comprises an additional C-terminal glycine-lysine dipeptide (G446 and K447, numbering according to Kabat EU index). In one embodiment of all aspects as reported herein, an antibody comprising a heavy chain including a CH3 domain, as specified herein, comprises an additional C-terminal glycine residue (G446, numbering according to Kabat EU index).

In a further aspect, an anti-ANG2 antibody according to any of the above embodiments may incorporate any of the features, singly or in combination, as described in Sections 1-5 below.

1. Antibody Affinity

In certain embodiments, an antibody provided herein has a dissociation constant (KD) of $\leq 1$ µM, $\leq 100$ nM, or $\leq 10$ nM (e.g. $10^{-8}$ M or less).

Methods for the determination of the KD value are outlined in the Examples below.

When using a BIACORE® surface plasmon resonance assay the KD value can be measured alternatively as follows: Binding of the antibodies or antibody fragments to human ANG2-RBD-Fc-region fusion can be investigated by surface plasmon resonance using a BIACORE T200 instrument (GE Healthcare). Around 4000 RU of anti-human antibody (10 µg/ml anti-human IgG (Fc) antibody; ordering code BR-1008-39; GE Healthcare) are coupled on a Series S CM5 chip (GE Healthcare BR-1005-30) at pH 5.0 by using an amine coupling kit supplied by the GE Healthcare. HBS-N (10 mM HEPES, 150 mM NaCl pH 7.4, GE Healthcare) is used as running buffer during the immobilization procedure. For the following kinetic characterization, sample and running buffer is HBS-P (10 mM HEPES, 150 mM NaCl pH 7.4, 0.05% Surfactant P20; GE Healthcare). The flow cell is set to 25° C.—and the sample block is set to 12° C.—and primed with running buffer twice prior to kinetic characterization.

ANG2-RBD-Fc-region fusion is captured by injecting a 1 µg/ml solution for 30 sec. at a flow rate of 5 µl/min. Association is measured by injection of the Cross-Fabs in various concentrations in solution for 90 sec. at a flow rate of 90 µl/min starting with 300 nM in serial 1:3 dilutions. The dissociation phase is monitored for up to 600 sec. and triggered by switching from the sample solution to running buffer. All surfaces are regenerated by 60 sec. washing with a 3 M $MgCl_2$ solution at a flow rate of 5 µl/min. Bulk refractive index differences are corrected by subtracting the response obtained from an anti-human IgG antibody (Fc) surface. Blank injections are also subtracted (=double referencing). For calculation of KD and other kinetic parameters the Langmuir 1:1 model is used.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (2003) 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

4. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for ANG2 and the other is for any other antigen. In certain embodiments, bispecific antibodies may bind to two different epitopes of ANG2. Bispecific antibodies may also be used to localize cytotoxic agents to cells which express ANG2. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to ANG2 as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

5. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 13 under the heading of "preferred substitutions". More substantial changes are provided in Table 13 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 13

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; norleucine | Leu |
| Leu (L) | norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; norleucine | Leu |

Amino acids may be grouped according to common side-chain properties:
(1) hydrophobic: norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region (see, e.g., Wright, A. and Morrison, S. L., TIBTECH 15 (1997) 26-32). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-Region Variants

In certain embodiments, one or more amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc (RIII only, whereas monocytes express FcγRI, FcγRII and FcγRIII FcR expression on hematopoietic cells is summarized in Table 3 on page 464 of Ravetch, J. V. and Kinet, J. P., Annu. Rev. Immunol. 9 (1991) 457-492.

Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity (see, e.g., C1q and C3c binding ELISA in WO 2006/029879 and WO 2005/100402). To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006: 1759-1769).

Antibodies with reduced effector function include those with substitution of one or more of Fc-region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604)

In certain embodiments, an antibody variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc-region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-ANG2 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-ANG2 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-ANG2 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in E. coli) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized", resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts (see, e.g., U.S. Pat. Nos. 5,959,177, 6,040,498, 6,420,548, 7,125,978, and 6,417,429 (describing PLANTIBODIES™ technology for producing antibodies in transgenic plants)).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR$^-$ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays

Anti-ANG2 antibodies provided herein may be identified, screened for, or characterized for their physical/chemical properties and/or biological activities by various assays known in the art. Exemplary assays are reported in the Examples.

D. Immunoconjugates

The invention also provides immunoconjugates comprising an anti-ANG2 antibody as reported herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, L. M. et al., Cancer Res. 53 (1993) 3336-3342; and Lode, H. N. et al., Cancer Res. 58 (1998) 2925-2928); an anthracycline such as daunomycin or doxorubicin (see Kratz, F. et al., Curr. Med. Chem. 13 (2006) 477-523; Jeffrey, S. C., et al., Bioorg. Med. Chem. Lett. 16 (2006) 358-362; Torgov, M. Y., et al., Bioconjug. Chem. 16 (2005) 717-721; Nagy, A., et al., Proc. Natl. Acad. Sci. USA 97 (2000) 829-834; Dubowchik, G. M., et al., Bioorg. & Med. Chem. Letters 12 (2002) 1529-1532; King, H. D., et al., J. Med. Chem. 45 (2002) 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S. et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V. et al., Cancer Res. 52 (1992) 127-131; U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-ANG2 antibodies provided herein is useful for detecting the presence of ANG2 in a biological sample. The term "detecting" as used herein encompasses quantitative or qualitative detection.

In one embodiment, an anti-ANG2 antibody for use in a method of diagnosis or detection is provided. In a further aspect, a method of detecting the presence of ANG2 in a biological sample is provided. In certain embodiments, the method comprises contacting the biological sample with an anti-ANG2 antibody as described herein under conditions permissive for binding of the anti-ANG2 antibody to ANG2, and detecting whether a complex is formed between the anti-ANG2 antibody and ANG2. Such method may be an in vitro or in vivo method. In one embodiment, an anti-ANG2 antibody is used to select subjects eligible for therapy with an anti-ANG2 antibody, e.g. where ANG2 is a biomarker for selection of patients.

In certain embodiments, labeled anti-ANG2 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-ANG2 antibody as described herein are prepared by mixing such antibody having the desired degree of purity with one or more optional pharmaceutically acceptable carriers (Remington's Pharmaceutical Sciences, 16$^{th}$ edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an anti-IL-1beta antibody or an anti-PDGF-B antibody. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16$^{th}$ edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-ANG2 antibodies provided herein may be used in therapeutic methods.

In one aspect, an anti-ANG2 antibody for use as a medicament is provided. In further aspects, an anti-ANG2 antibody for use in treating an ocular vascular disease, preferably macular degeneration, is provided. In certain embodiments, an anti-ANG2 antibody for use in a method of treatment is provided. In certain embodiments, the invention provides an anti-ANG2 antibody for use in a method of treating an individual having an ocular vascular disease, preferably macular degeneration, comprising administering to the individual an effective amount of the anti-ANG2 antibody. In one such embodiment, the method further comprises administering to the individual an effective amount of at least one additional therapeutic agent, e.g., as described below. In further embodiments, the invention provides an anti-ANG2 antibody for use in inhibiting angiogenesis. In certain embodiments, the invention provides an anti-ANG2 antibody for use in a method of inhibiting angiogenesis in an individual comprising administering to the individual an effective of the anti-ANG2 antibody to inhibit angiogenesis. An "individual" according to any of the above embodiments is preferably a human.

In a further aspect, the invention provides for the use of an anti-ANG2 antibody in the manufacture or preparation of a medicament. In one embodiment, the medicament is for treatment of an ocular vascular disease, preferably macular degeneration. In a further embodiment, the medicament is for use in a method of treating an ocular vascular disease, preferably macular degeneration, comprising administering to an individual having an ocular vascular disease, preferably macular degeneration, an effective amount of the medicament. In one such embodiment, the method further comprises administering to the individual an effective amount of at least one additional therapeutic agent, e.g., as described below. In a further embodiment, the medicament is for inhibiting angiogenesis. In a further embodiment, the medicament is for use in a method of inhibiting angiogenesis in an individual comprising administering to the individual an amount effective of the medicament to inhibit angiogenesis. An "individual" according to any of the above embodiments may be a human.

In a further aspect, the invention provides a method for treating an ocular vascular disease, preferably macular degeneration. In one embodiment, the method comprises administering to an individual having such an ocular vascular disease, preferably macular degeneration, an effective amount of an anti-ANG2 antibody. In one such embodiment, the method further comprises administering to the individual an effective amount of at least one additional therapeutic agent, as described below. An "individual" according to any of the above embodiments may be a human.

In a further aspect, the invention provides a method for inhibiting angiogenesis in an individual. In one embodiment, the method comprises administering to the individual an effective amount of an anti-ANG2 antibody to inhibit angiogenesis. In one embodiment, an "individual" is a human.

In a further aspect, the invention provides pharmaceutical formulations comprising any of the anti-ANG2 antibodies provided herein, e.g., for use in any of the above therapeutic methods. In one embodiment, a pharmaceutical formulation comprises any of the anti-ANG2 antibodies provided herein and a pharmaceutically acceptable carrier. In another embodiment, a pharmaceutical formulation comprises any of the anti-ANG2 antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is an anti-IL-1beta antibody or an anti-PDGF-B antibody.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-ANG2 antibody and administration of an additional therapeutic agent occur within about one month, or within about one, two or three weeks, or within about one, two, three, four, five, or six days, of each other.

An antibody of the invention (and any additional therapeutic agent) can be administered by any suitable means, including parenteral, intravenous, intravitreal, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 50 mg/kg (e.g. 0.5 mg/kg-30 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg, 10 mg/kg, 30 mg/kg or 50 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-ANG2 antibody.

III. Articles of Manufacture

In another aspect of the invention, an article of manufacture containing materials useful for the treatment, prevention and/or diagnosis of the disorders described above is provided. The article of manufacture comprises a container and a label or package insert on or associated with the container.

Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-ANG2 antibody.

IV. Specific Embodiments

1. An antibody that specifically binds to human ANG2, wherein the antibody comprises (a) a HVR-H1 comprising the amino acid sequence of SEQ ID NO: 20, (b) a HVR-H2 comprising the amino acid sequence of SEQ ID NO: 21, and (c) a HVR-H3 comprising the amino acid sequence of SEQ ID NO: 23.
2. An antibody that specifically binds to human ANG2, wherein the antibody comprises (a) a HVR-H1 comprising the amino acid sequence of SEQ ID NO: 20, (b) a HVR-H2 comprising the amino acid sequence of SEQ ID NO: 22, and (c) a HVR-H3 comprising the amino acid sequence of SEQ ID NO: 23.
3. The antibody according to any one of embodiments 1 to 2, wherein the antibody comprises (a) a HVR-L1 comprising the amino acid sequence of SEQ ID NO: 25; (b) a HVR-L2 comprising the amino acid sequence of SEQ ID NO: 26; and (c) HVR-L3 comprising the amino acid sequence of SEQ ID NO: 27.
4. The antibody according to any one of embodiments 1 to 2, wherein the antibody comprises (a) a HVR-L1 comprising the amino acid sequence of SEQ ID NO: 34; (b) a HVR-L2 comprising the amino acid sequence of SEQ ID NO: 35; and (c) HVR-L3 comprising the amino acid sequence of SEQ ID NO: 36.
5. The antibody according to any one of embodiments 1 to 4, wherein the antibody comprises (a) a VH sequence having at least 95% sequence identity to the amino acid sequence of SEQ ID NO: 19, (b) a VL sequence having at least 95% sequence identity to the amino acid sequence of SEQ ID NO: 06 or SEQ ID NO: 33, or (c) a VH sequence as in (a) and a VL sequence as in (b).
6. An antibody that specifically binds to human ANG2, wherein the antibody comprises (a) a HVR-H1 comprising the amino acid sequence of SEQ ID NO: 38, (b) a HVR-H2 comprising the amino acid sequence of SEQ ID NO: 39, and (c) a HVR-H3 comprising the amino acid sequence of SEQ ID NO: 41.
7. An antibody that specifically binds to human ANG2, wherein the antibody comprises (a) a HVR-H1 comprising the amino acid sequence of SEQ ID NO: 38, (b) a HVR-H2 comprising the amino acid sequence of SEQ ID NO: 40, and (c) a HVR-H3 comprising the amino acid sequence of SEQ ID NO: 41.
8. The antibody according to any one of embodiments 6 to 7, wherein the antibody comprises (a) a HVR-L1 comprising the amino acid sequence of SEQ ID NO: 43; (b) a HVR-L2 comprising the amino acid sequence of SEQ ID NO: 44; and (c) HVR-L3 comprising the amino acid sequence of SEQ ID NO: 45.
9. The antibody according to any one of embodiments 6 to 8, wherein the antibody comprises (a) a VH sequence having at least 95% sequence identity to the amino acid sequence of SEQ ID NO: 37, (b) a VL sequence having at least 95% sequence identity to the amino acid sequence of SEQ ID NO: 42, or (c) a VH sequence as in (a) and a VL sequence as in (b).
10. An antibody that specifically binds to human ANG2, wherein the antibody
    i) comprises a heavy chain variable domain that has a sequence identity to SEQ ID NO: 19 of more than 70% and a light chain variable domain that has a sequence identity to SEQ ID NO: 6 of more than 70%,
    ii) has in the heavy chain variable domain at position 28 the amino acid residue asparagine (N), at position 30 the amino acid residue alanine (A), at position 100b the amino acid residue proline (P) and at position 100j the amino acid residue alanine (A) and in the light chain variable domain at position 51 the amino acid residue threonine (T) (numbering according to Kabat), and
    iii) the antibody has a lower $EC_{50}$ value for the inhibition of the binding of ANG2 to its receptor Tie2 in a cell based assay using HEK293 cells stably expressing human Tie2 determined using a Tie2 phosphorylation ELISA compared to an antibody comprising a heavy chain variable domain that has a sequence identity to SEQ ID NO: 19 and a light chain variable domain that has a sequence identity to SEQ ID NO: 6 or SEQ ID NO: 33.
11. The antibody according to embodiment 10, wherein the sequence identity is more than 80%, preferably more than 90%, most preferably 95% or more.
12. The antibody according to any one of embodiments 1 to 11, wherein the antibody is of the human subclass IgG1 or the human subclass IgG4.
13. The antibody according to any one of embodiments 1 to 12, wherein the antibody is a monoclonal antibody.
14. An antibody comprising a VH sequence of SEQ ID NO: 28 and a VL sequence of SEQ ID NO: 33.
15. An antibody comprising a VH sequence of SEQ ID NO: 19 and a VL sequence of SEQ ID NO: 24.
16. An antibody comprising a VH sequence of SEQ ID NO: 37 and a VL sequence of SEQ ID NO: 42.
17. The antibody according to any one of embodiments 1 to 16, wherein the antibody is a bispecific antibody.
18. The antibody according to embodiment 17, wherein the bispecific antibody is a CrossMab.
19. The antibody according to any one of embodiments 1 to 18, wherein the antibody blocks the biological activity of human ANG2 by inhibiting the binding of human ANG2 to human Tie2 receptor.

20. The antibody according to any one of embodiments 1 to 19, wherein the antibody is a bivalent, bispecific antibody comprising
   a) a first light chain and a first heavy chain of an antibody specifically binding to a first antigen, and
   b) a second light chain and a second heavy chain of an antibody specifically binding to a second antigen, wherein the variable domains VL and VH of the second light chain and the second heavy chain are replaced by each other,
   wherein the first antigen or the second antigen is human ANG2.
21. The antibody according to embodiment 20, wherein the antibody comprises
   i) in the constant domain CL of the first light chain under a) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the first heavy chain under a) the amino acid at position 147 or the amino acid at position 213 is substituted independently by glutamic acid (E) or aspartic acid (D) (numbering according to Kabat EU index),
   or
   ii) in the constant domain CL of the second light chain under b) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the second heavy chain under b) the amino acid at position 147 or the amino acid at position 213 is substituted independently by glutamic acid (E) or aspartic acid (D) (numbering according to Kabat EU index).
22. The antibody according to any one of embodiment 20 to 21, wherein the antibody comprises in the constant domain CL of the second heavy chain the amino acids at position 124 and 123 are substituted by K (numbering according to Kabat EU index).
23. The antibody according to any one of embodiment 20 to 22, wherein the antibody comprises in the constant domain CH1 of the second light chain the amino acids at position 147 and 213 are substituted by E (numbering according to EU index of Kabat).
24. The antibody according to any one of embodiment 20 to 23, wherein the antibody comprises in the constant domain CL of the first light chain the amino acids at position 124 and 123 are substituted by K, and in the constant domain CH1 of the first heavy chain the amino acids at position 147 and 213 are substituted by E (numbering according to Kabat EU index).
25. The antibody according to any one of embodiment 20 to 24, wherein the antibody comprises in the constant domain CL of the second heavy chain the amino acids at position 124 and 123 are substituted by K, and wherein in the constant domain CH1 of the second light chain the amino acids at position 147 and 213 are substituted by E, and in the variable domain VL of the first light chain the amino acid at position 38 is substituted by K, in the variable domain VH of the first heavy chain the amino acid at position 39 is substituted by E, in the variable domain VL of the second heavy chain the amino acid at position 38 is substituted by K, and in the variable domain VH of the second light chain the amino acid at position 39 is substituted by E (numbering according to Kabat EU index).

26. The antibody according to any one of embodiments 1 to 19, wherein the antibody is a bivalent, bispecific antibody, comprising
   a) a first light chain and a first heavy chain of an antibody specifically binding to a first antigen, and
   b) a second light chain and a second heavy chain of an antibody specifically binding to a second antigen, wherein the variable domains VL and VH of the second light chain and the second heavy chain are replaced by each other, and wherein the constant domains CL and CH1 of the second light chain and the second heavy chain are replaced by each other, wherein the first antigen or the second antigen is human ANG2.
27. The antibody according to any one of embodiments 1 to 19, wherein the antibody is a bivalent, bispecific antibody, comprising
   a) a first light chain and a first heavy chain of an antibody specifically binding to a first antigen, and
   b) a second light chain and a second heavy chain of an antibody specifically binding to a second antigen, wherein the constant domains CL and CH1 of the second light chain and the second heavy chain are replaced by each other, wherein the first antigen or the second antigen is human ANG2.
28. The antibody according to any one of embodiments 1 to 19, wherein the antibody is a multispecific antibody comprising
   a) a full length antibody specifically binding to a first antigen and consisting of two antibody heavy chains and two antibody light chains, and
   b) one, two, three or four single chain Fab fragments specifically binding to one to four further antigens (i.e. a second and/or third and/or fourth and/or fifth antigen, preferably specifically binding to one further antigen, i.e. a second antigen),
   wherein said single chain Fab fragments under b) are fused to said full length antibody under a) via a peptidic linker at the C- or N-terminus of the heavy or light chain of said full length antibody,
   wherein the first antigen or one of the further antigens is human ANG2.
29. The antibody according to any one of embodiments 1 to 19, wherein the antibody is a trivalent, bispecific antibody comprising
   a) a full length antibody specifically binding to a first antigen and consisting of two antibody heavy chains and two antibody light chains,
   b) a first polypeptide consisting of
      ba) an antibody heavy chain variable domain (VH), or
      bb) an antibody heavy chain variable domain (VH) and an antibody constant domain 1 (CH1),
   wherein said first polypeptide is fused with the N-terminus of its VH domain via a peptidic linker to the C-terminus of one of the two heavy chains of said full length antibody,
   c) a second polypeptide consisting of
      ca) an antibody light chain variable domain (VL), or
      cb) an antibody light chain variable domain (VL) and an antibody light chain constant domain (CL),
      wherein said second polypeptide is fused with the N-terminus of the VL domain via a peptidic linker to the C-terminus of the other of the two heavy chains of said full length antibody, and
wherein the antibody heavy chain variable domain (VH) of the first polypeptide and the antibody light chain variable domain (VL) of the second polypeptide together form an antigen-binding site specifically binding to a second antigen,
and
wherein the first antigen or the second antigen is human ANG2.

30. The antibody according to embodiment 29, wherein the antibody heavy chain variable domain (VH) of the polypeptide under b) and the antibody light chain variable domain (VL) of the polypeptide under c) are linked and stabilized via an interchain disulfide bridge by introduction of a disulfide bond between the following positions:
   i) heavy chain variable domain position 44 to light chain variable domain position 100, or
   ii) heavy chain variable domain position 105 to light chain variable domain position 43, or
   iii) heavy chain variable domain position 101 to light chain variable domain position 100 (numbering always according to Kabat EU index).

31. The antibody according to any one of embodiments 1 to 19, wherein the antibody is a trispecific or tetraspecific antibody, comprising
   a) a first light chain and a first heavy chain of a full length antibody which specifically binds to a first antigen, and
   b) a second (modified) light chain and a second (modified) heavy chain of a full length antibody which specifically binds to a second antigen, wherein the variable domains VL and VH are replaced by each other, and/or wherein the constant domains CL and CH1 are replaced by each other, and
   c) wherein one to four antigen binding peptides which specifically bind to one or two further antigens (i.e. to a third and/or fourth antigen) are fused via a peptidic linker to the C- or N-terminus of the light chains or heavy chains of a) and/or b),
   wherein the first antigen or the second antigen or one of the further antigens is human ANG2.

32. The antibody according to any one of embodiments 1 to 19, wherein the antibody is a bispecific, tetravalent antibody comprising
   a) two light chains and two heavy chains of an antibody, which specifically bind to a first antigen (and comprise two Fab fragments),
   b) two additional Fab fragments of an antibody, which specifically bind to a second antigen, wherein said additional Fab fragments are fused both via a peptidic linker either to the C- or N-termini of the heavy chains of a),
   and
   wherein in the Fab fragments the following modifications were performed
      i) in both Fab fragments of a), or in both Fab fragments of b), the variable domains VL and VH are replaced by each other, and/or the constant domains CL and CH1 are replaced by each other,
      or
      ii) in both Fab fragments of a) the variable domains VL and VH are replaced by each other, and the constant domains CL and CH1 are replaced by each other,
      and
      in both Fab fragments of b) the variable domains VL and VH are replaced by each other, or the constant domains CL and CH1 are replaced by each other,
      or
      iii) in both Fab fragments of a) the variable domains VL and VH are replaced by each other, or the constant domains CL and CH1 are replaced by each other,
      and
      in both Fab fragments of b) the variable domains VL and VH are replaced by each other, and the constant domains CL and CH1 are replaced by each other,
      or
      iv) in both Fab fragments of a) the variable domains VL and VH are replaced by each other, and in both Fab fragments of b) the constant domains CL and CH1 are replaced by each other,
      or
      v) in both Fab fragments of a) the constant domains CL and CH1 are replaced by each other, and in both Fab fragments of b) the variable domains VL and VH are replaced by each other,
   wherein the first antigen or the second antigen is human ANG2.

33. The antibody according to any one of embodiments 1 to 19, wherein the antibody is a bispecific, tetravalent antibody comprising:
   a) a (modified) heavy chain of a first antibody, which specifically binds to a first antigen and comprises a first VH—CH1 domain pair, wherein to the C-terminus of said heavy chain the N-terminus of a second VH—CH1 domain pair of said first antibody is fused via a peptidic linker,
   b) two light chains of said first antibody of a),
   c) a (modified) heavy chain of a second antibody, which specifically binds to a second antigen and comprises a first VH-CL domain pair, wherein to the C-terminus of said heavy chain the N-terminus of a second VH-CL domain pair of said second antibody is fused via a peptidic linker, and
   d) two (modified) light chains of said second antibody of c), each comprising a CL-CH1 domain pair,
   wherein the first antigen or the second antigen is human ANG2.

34. The antibody according to any one of embodiments 1 to 19, wherein the antibody is a bispecific antibody comprising
   a) the heavy chain and the light chain of a first full length antibody that specifically binds to a first antigen, and
   b) the heavy chain and the light chain of a second full length antibody that specifically binds to a second antigen, wherein the N-terminus of the heavy chain is connected to the C-terminus of the light chain via a peptidic linker,
   wherein the first antigen or the second antigen is human ANG2.

35. The antibody according to any one of embodiments 1 to 19, wherein the antibody is a bispecific antibody comprising
   a) a full length antibody specifically binding to a first antigen and consisting of two antibody heavy chains and two antibody light chains, and
   b) an Fv fragment specifically binding to a second antigen comprising a $VH^2$ domain and a $VL^2$ domain, wherein both domains are connected to each other via a disulfide bridge,
   wherein only either the $VH^2$ domain or the $VL^2$ domain is fused via a peptidic linker to the heavy or light chain of the full length antibody specifically binding to a first antigen, wherein the first antigen or the second antigen is human ANG2.

36. The antibody according to any one of embodiments 1 to 35, wherein the antibody comprises a first Fc-region polypeptide and a second Fc-region polypeptide, and wherein
    i) the first Fc-region polypeptide is selected from the group comprising
        human IgG1 Fc-region polypeptide,
        human IgG2 Fc-region polypeptide,
        human IgG3 Fc-region polypeptide,
        human IgG4 Fc-region polypeptide,
        human IgG1 Fc-region polypeptide with the mutations L234A, L235A,
        human IgG1 Fc-region polypeptide with the mutations Y349C, T366S, L368A, Y407V,
        human IgG1 Fc-region polypeptide with the mutations S354C, T366S, L368A, Y407V,
        human IgG1 Fc-region polypeptide with the mutations L234A, L235A, Y349C, T366S, L368A, Y407V,
        human IgG1 Fc-region polypeptide with the mutations L234A, L235A, S354C, T366S, L368A, Y407V,
        human IgG1 Fc-region polypeptide with the mutations P329G,
        human IgG1 Fc-region polypeptide with the mutations L234A, L235A, P329G,
        human IgG1 Fc-region polypeptide with the mutations P329G, Y349C, T366S, L368A, Y407V,
        human IgG1 Fc-region polypeptide with the mutations P329G, S354C, T366S, L368A, Y407V,
        human IgG1 Fc-region polypeptide with the mutations L234A, L235A, P329G, Y349C, T366S, L368A, Y407V,
        human IgG1 Fc-region polypeptide with the mutations L234A, L235A, P329G, S354C, T366S, L368A, Y407V,
        human IgG4 Fc-region polypeptide with the mutations S228P, L235E,
        human IgG4 Fc-region polypeptide with the mutations S228P, L235E, P329G,
        human IgG4 Fc-region polypeptide with the mutations Y349C, T366S, L368A, Y407V,
        human IgG4 Fc-region polypeptide with the mutations S354C, T366S, L368A, Y407V,
        human IgG4 Fc-region polypeptide with the mutations S228P, L235E, Y349C, T366S, L368A, Y407V,
        human IgG4 Fc-region polypeptide with the mutations S228P, L235E, S354C, T366S, L368A, Y407V,
        human IgG4 Fc-region polypeptide with the mutations P329G,
        human IgG4 Fc-region polypeptide with the mutations P329G, Y349C, T366S, L368A, Y407V,
        human IgG4 Fc-region polypeptide with the mutations P329G, S354C, T366S, L368A, Y407V,
        human IgG4 Fc-region polypeptide with the mutations S228P, L235E, P329G, Y349C, T366S, L368A, Y407V,
        human IgG4 Fc-region polypeptide with the mutations S228P, L235E, P329G, S354C, T366S, L368A, Y407V,
        human IgG1, IgG2 or IgG4 with the mutations K392D, and
        human IgG3 with the mutation N392D, and
    ii) the second Fc-region polypeptide is selected from the group comprising
        human IgG1 Fc-region polypeptide,
        human IgG2 Fc-region polypeptide,
        human IgG3 Fc-region polypeptide,
        human IgG4 Fc-region polypeptide,
        human IgG1 Fc-region polypeptide with the mutations L234A, L235A,
        human IgG1 Fc-region polypeptide with the mutations S354C, T366W,
        human IgG1 Fc-region polypeptide with the mutations Y349C, T366W,
        human IgG1 Fc-region polypeptide with the mutations L234A, L235A, S354C, T366W,
        human IgG1 Fc-region polypeptide with the mutations L234A, L235A, Y349C, T366W,
        human IgG1 Fc-region polypeptide with the mutations P329G,
        human IgG1 Fc-region polypeptide with the mutations L234A, L235A, P329G,
        human IgG1 Fc-region polypeptide with the mutations P329G, S354C, T366W,
        human IgG1 Fc-region polypeptide with the mutations P329G, Y349C, T366W,
        human IgG1 Fc-region polypeptide with the mutations L234A, L235A, P329G, S354C, T366W,
        human IgG1 Fc-region polypeptide with the mutations L234A, L235A, P329G, Y349C, T366W,
        human IgG4 Fc-region polypeptide with the mutations S228P, L235E,
        human IgG4 Fc-region polypeptide with the mutations S228P, L235E, P329G,
        human IgG4 Fc-region polypeptide with the mutations S354C, T366W,
        human IgG4 Fc-region polypeptide with the mutations Y349C, T366W,
        human IgG4 Fc-region polypeptide with the mutations S228P, L235E, S354C, T366W,
        human IgG4 Fc-region polypeptide with the mutations S228P, L235E, Y349C, T366W,
        human IgG4 Fc-region polypeptide with the mutations P329G,
        human IgG4 Fc-region polypeptide with the mutations P329G, S354C, T366W,
        human IgG4 Fc-region polypeptide with the mutations P329G, Y349C, T366W,
        human IgG4 Fc-region polypeptide with the mutations S228P, L235E, P329G, S354C, T366W,
        human IgG4 Fc-region polypeptide with the mutations S228P, L235E, P329G, Y349C, T366W,
        human IgG1 with the mutations D399K, D356K, and/or E357K, and
        human IgG2, IgG3 or IgG4 with the mutations D399K, E356K, and/or E357K.

37. The antibody according to any one of embodiments 1 to 35, wherein the antibody comprises a first Fc-region polypeptide and a second Fc-region polypeptide, and wherein
    i) the first Fc-region polypeptide is a human IgG1 Fc-region polypeptide and the second Fc-region polypeptide is a human IgG1 Fc-region polypeptide, or
    ii) the first Fc-region polypeptide is a human IgG1 Fc-region polypeptide with the mutations L234A, L235A and the second Fc-region polypeptide is a human IgG1 Fc-region polypeptide with the mutations L234A, L235A, or iii) the first Fc-region polypeptide is a human IgG1 Fc-region polypeptide with the mutations L234A, L235A, P329G and the second Fc-region polypeptide is a human IgG1 Fc-region polypeptide with the mutations L234A, L235A, P329G, or iv) the first Fc-region polypeptide is a human IgG1 Fc-region polypeptide with the mutations L234A, L235A, S354C, T366W and the second Fc-region polypeptide is a human IgG1 Fc-region polypeptide with the mutations L234A, L235A, Y349C, T366S, L368A, Y407V, or v) the first Fc-region polypeptide is a human IgG1 Fc-region polypeptide with the mutations L234A, L235A, P329G, S354C, T366W and the second Fc-region polypeptide is a human IgG1 Fc-region polypeptide with the mutations L234A, L235A, P329G, Y349C, T366S, L368A, Y407V, or vi) the first Fc-region polypeptide is a human IgG4 Fc-region polypeptide and the second Fc-region polypeptide is a human IgG4 Fc-region polypeptide, or vii) the first Fc-region polypeptide is a human IgG4 Fc-region polypeptide with the mutations S228P, L235E and the second Fc-region polypeptide is a human IgG4 Fc-region polypeptide with the mutations S228P, L235E, or viii) the first Fc-region polypeptide is a human IgG4 Fc-region polypeptide with the mutations S228P, L235E, P329G and the second Fc-region polypeptide is a human IgG4 Fc-region polypeptide with the mutations S228P, L235E, P329G, or ix) the first Fc-region polypeptide is a human IgG4 Fc-region polypeptide with the mutations S228P, L235E, S354C, T366W and the second Fc-region polypeptide is a human IgG4 Fc-region polypeptide with the mutations S228P, L235E, Y349C, T366S, L368A, Y407V, or x) the first Fc-region polypeptide is a human IgG4 Fc-region polypeptide with the mutations S228P, L235E, P329G, S354C, T366W and the second Fc-region polypeptide is a human IgG4 Fc-region polypeptide with the mutations S228P, L235E, P329G, Y349C, T366S, L368A, Y407V.

38. The antibody according to any one of embodiments 1 to 37, wherein the antibody comprises a first Fc-region polypeptide and a second Fc-region polypeptide, and wherein the antibody comprises the combination of mutations
    i) I253A, H310A, and H435A, or
    ii) H310A, H433A, and Y436A, or
    iii) L251D, L314D, and L432D, or
    iv) combinations of i) to iii)
    in the first Fc-region polypeptide and in the second Fc-region polypeptide.

39. The antibody according to any one of embodiments 1 to 37, wherein the antibody comprises a first Fc-region polypeptide and a second Fc-region polypeptide, and wherein
    a) the first and a second Fc-region polypeptide are both of human IgG1 or human IgG4 subclass (derived from human origin) and comprise one or two of the mutations selected from i) the group I253A, H310A and H435A, or ii) the group H310A, H433A and Y436A, or iii) the group L251D, L314D and L432D (numbering according to Kabat EU index numbering system) in the first Fc-region polypeptide and one or two of the mutations selected from the group comprising the mutations L251D, I253A, H310A, L314D, L432D, H433A, H435A and Y436A (numbering according to Kabat EU index numbering system) in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D are comprised in the variant (human) IgG class Fc-region,
    or
    b) the first and a second Fc-region polypeptide both of human IgG1 or human IgG4 subclass (i.e. derived from human origin) and both comprise the mutations I253A/H310A/H435A or H310A/H433A/Y436A or L251D/L314D/L432D or combinations thereof in the Fc-region (numbering according to Kabat EU index numbering system), whereby either all mutations are in the first or the second Fc-region polypeptide, or one or two mutations are in the first Fc-region polypeptide and one or two mutations are in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D are comprised in the Fc-region,
    or
    c) the first and a second Fc-region polypeptide both of human IgG1 or human IgG4 subclass (i.e. derived from human origin) and comprise the mutations I253A/H310A/H435A or H310A/H433A/Y436A or L251D/L314D/L432D in the first as well as in the second Fc-region polypeptide (numbering according to Kabat EU index numbering system), or comprises the combinations of the mutations I253A/H310A/H435A in the first Fc-region polypeptide and the combination of the mutations H310A/H433A/Y436A in the second Fc-region polypeptide (numbering according to Kabat EU index numbering system).

40. The antibody according to any one of embodiments 1 to 37, wherein the antibody comprises a first Fc-region polypeptide and a second Fc-region polypeptide, and wherein
    a) the first variant Fc-region polypeptide is derived from a first parent IgG class Fc-region polypeptide and the second variant Fc-region polypeptide is derived from a second parent IgG class Fc-region polypeptide, whereby the first parent IgG class Fc-region polypeptide is identical to or different from the second parent IgG class Fc-region polypeptide, and
    b) the first variant Fc-region polypeptide differs from the second variant Fc-region polypeptide in one or more amino acid residues other than those amino acid residues in which the first parent IgG class Fc-region polypeptide differs from the second parent IgG class Fc-region polypeptide, and
    c) the IgG class Fc-region comprising the first variant Fc-region polypeptide and the second variant Fc-region polypeptide has an affinity to a human Fc-receptor that is different than that of an IgG class Fc-region comprising the first parent IgG class Fc-region polypeptide of a) and the second parent IgG class Fc-region polypeptide of a),
    wherein either the first Fc-region polypeptide or the second Fc-region polypeptide or both Fc-region polypeptides comprise independently of each other one of the following mutations or combination of mutations: T307H, or Q311H, or
E430 H, or
N434H, or
T307H and Q311H, or
T307H and E430H, or
T307H and N434A, or
T307H and N434H, or
T307Q and Q311H, or
T307Q and E430H, or
T307Q and N434H, or
T307H and Q311H and E430H and N434A, or
T307H and Q311H and E430H and N434H, or
T307H and Q311H and E430H and N434Y, or
T307Q and Q311H and E430H and N434A, or
T307Q and Q311H and E430H and N434H, or
T307Q and Q311H and E430H and N434Y, or
T307Q and V308P and N434Y and Y436H, or
T307H and M252Y and S254T and T256E, or
T307Q and M252Y and S254T and T256E, or
Q311H and M252Y and S254T and T256E, or
E430 H and M252Y and S254T and T256E, or
N434H and M252Y and S254T and T256E, or
T307H and Q311H and M252Y and S254T and T256E, or
T307H and E430H and M252Y and S254T and T256E, or
T307H and N434A and M252Y and S254T and T256E, or
T307H and N434H and M252Y and S254T and T256E, or
T307Q and Q311H and M252Y and S254T and T256E, or
T307Q and E430H and M252Y and S254T and T256E, or
T307Q and N434H and M252Y and S254T and T256E, or
T307H and Q311H and E430H and N434A and M252Y and S254T and T256E, or
T307H and Q311H and E430H and N434H and M252Y and S254T and T256E, or
T307H and Q311H and E430H and N434Y and M252Y and S254T and T256E, or
T307Q and Q311H and E430H and N434A and M252Y and S254T and T256E, or
T307Q and Q311H and E430H and N434H and M252Y and S254T and T256E, or
T307Q and Q311H and E430H and N434Y and M252Y and S254T and T256E, or
T307Q and V308P and N434Y and Y436H and M252Y and S254T and T256E.

41. The antibody according to any one of embodiments 1 to 37, wherein the antibody comprises a first Fc-region polypeptide and a second Fc-region polypeptide, and wherein the first Fc-region polypeptide comprises the mutations Y349C, T366S, L368A and Y407V (hole-chain) and the second Fc-region polypeptide comprises the mutations S354C and T366W (knob-chain), and wherein the first Fc-region polypeptide (hole-chain) comprises the mutations
   i) I253A or I253G, and
   ii) L314A or L314G or L314D,
and wherein the first Fc-region polypeptide and the second Fc-region polypeptide are connected by one or more disulfide bridges,
and wherein the CH3-domain of the first polypeptide and the CH3-domain of the second polypeptide both bind or both do not bind to protein A
(numbering according to the Kabat EU index).

42. The antibody according to embodiment 41, wherein the antibody comprises the mutations
   i) I253A or I253G, and
   ii) L314A or L314G or L314D, and
   iii) T250Q, and/or
   iv) T256E or T256A.

43. The antibody according to any one of embodiments 41 to 42, wherein the antibody comprises the mutations
   i) I253A or I253G, and
   ii) L314A or L314G or L314D, and
   iii) optionally a) T250Q, and/or T256E or T256A, and.
   iv) a) L251A or L251G or L251D, and/or b) H310A or H310G.

44. The antibody according to any one of embodiments 41 to 43, wherein the antibody comprises the mutation
   i) I253A or I253G, and
   ii) L314A or L314G or L314D, and
   iii) a) T250Q, and/or T256E or T256A, and.
   iv) a) L251A or L251G or L251D, and/or b) H310A or H310G.
   v) optionally a) T307A or T307H or T307Q or T307P, and/or b) Q311H, and/or c) M252Y, and/or d) S254T.

45. The antibody according to any one of embodiments 41 to 44, wherein the antibody comprises the mutation
   i) T250Q, and/or
   ii) M252Y, and/or
   iii) S254T, and/or
   iv) T256E or T256A, and/or
   v) T307A or T307H or T307Q or T307P, and/or
   vi) Q311H.

46. An isolated antibody or an isolated antibody Fab fragment comprising
   a) a heavy chain that has the amino acid sequence of SEQ ID NO: 57 and a light chain that has the amino acid sequence of SEQ ID NO: 49, or
   b) a heavy chain that has the amino acid sequence of SEQ ID NO: 58 and a light chain that has the amino acid sequence of SEQ ID NO: 49, or
   c) a heavy chain that has the amino acid sequence of SEQ ID NO: 59 and a light chain that has the amino acid sequence of SEQ ID NO: 49, or
   d) a heavy chain that has the amino acid sequence of SEQ ID NO: 60 and a light chain that has the amino acid sequence of SEQ ID NO: 49, or
   e) a heavy chain that has the amino acid sequence of SEQ ID NO: 61 and a light chain that has the amino acid sequence of SEQ ID NO: 49, or
   f) a heavy chain that has the amino acid sequence of SEQ ID NO: 62 and a light chain that has the amino acid sequence of SEQ ID NO: 49, or
   g) a heavy chain that has the amino acid sequence of SEQ ID NO: 63 and a light chain that has the amino acid sequence of SEQ ID NO: 49, or
   h) a heavy chain that has the amino acid sequence of SEQ ID NO: 64 and a light chain that has the amino acid sequence of SEQ ID NO: 49, or
   i) a heavy chain that has the amino acid sequence of SEQ ID NO: 65 and a light chain that has the amino acid sequence of SEQ ID NO: 49, or
   j) a heavy chain that has the amino acid sequence of SEQ ID NO: 46 and a light chain that has the amino acid sequence of SEQ ID NO: 66, or
   k) a heavy chain that has the amino acid sequence of SEQ ID NO: 46 and a light chain that has the amino acid sequence of SEQ ID NO: 67, or l) a heavy chain that has the amino acid sequence of SEQ ID NO: 68 and a light chain that has the amino acid sequence of SEQ ID NO: 49, or
m) a heavy chain that has the amino acid sequence of SEQ ID NO: 69 and a light chain that has the amino acid sequence of SEQ ID NO: 50, or
n) a heavy chain that has the amino acid sequence of SEQ ID NO: 70 and a light chain that has the amino acid sequence of SEQ ID NO: 49, or
o) a heavy chain that has the amino acid sequence of SEQ ID NO: 47 and a light chain that has the amino acid sequence of SEQ ID NO: 49, or
p) a heavy chain that has the amino acid sequence of SEQ ID NO: 71 and a light chain that has the amino acid sequence of SEQ ID NO: 49, or
q) a heavy chain that has the amino acid sequence of SEQ ID NO: 72 and a light chain that has the amino acid sequence of SEQ ID NO: 49, or
r) a heavy chain that has the amino acid sequence of SEQ ID NO: 73 and a light chain that has the amino acid sequence of SEQ ID NO: 49, or
s) a heavy chain that has the amino acid sequence of SEQ ID NO: 72 and a light chain that has the amino acid sequence of SEQ ID NO: 50, or
t) a heavy chain that has the amino acid sequence of SEQ ID NO: 73 and a light chain that has the amino acid sequence of SEQ ID NO: 50, or
u) a heavy chain that has the amino acid sequence of SEQ ID NO: 48 and a light chain that has the amino acid sequence of SEQ ID NO: 49, or
v) a heavy chain that has the amino acid sequence of SEQ ID NO: 48 and a light chain that has the amino acid sequence of SEQ ID NO: 50, or
w) a heavy chain that has the amino acid sequence of SEQ ID NO: 74 and a light chain that has the amino acid sequence of SEQ ID NO: 49, or
x) a heavy chain that has the amino acid sequence of SEQ ID NO: 74 and a light chain that has the amino acid sequence of SEQ ID NO: 50, or
y) a heavy chain that has the amino acid sequence of SEQ ID NO: 47 and a light chain that has the amino acid sequence of SEQ ID NO: 50, or
z) a heavy chain that has the amino acid sequence of SEQ ID NO: 51 and a light chain that has the amino acid sequence of SEQ ID NO: 49, or
aa) a heavy chain that has the amino acid sequence of SEQ ID NO: 52 and a light chain that has the amino acid sequence of SEQ ID NO: 49, or
ab) a heavy chain that has the amino acid sequence of SEQ ID NO: 52 and a light chain that has the amino acid sequence of SEQ ID NO: 50, or
ac) a heavy chain that has the amino acid sequence of SEQ ID NO: 53 and a light chain that has the amino acid sequence of SEQ ID NO: 50, or
ad) a heavy chain that has the amino acid sequence of SEQ ID NO: 47 and a light chain that has the amino acid sequence of SEQ ID NO: 78, or
ae) a heavy chain that has the amino acid sequence of SEQ ID NO: 48 and a light chain that has the amino acid sequence of SEQ ID NO: 78, or
af) a heavy chain that has the amino acid sequence of SEQ ID NO: 46 and a light chain that has the amino acid sequence of SEQ ID NO: 50, or
ag) a first heavy chain that has the amino acid sequence of SEQ ID NO: 83, a second heavy chain that has the amino acid sequence of SEQ ID NO: 81, a first light chain that has the amino acid sequence of SEQ ID NO: 84, and a second light chain that has the amino acid sequence of SEQ ID NO: 82, or
ah) a first heavy chain that has the amino acid sequence of SEQ ID NO: 85, a second heavy chain that has the amino acid sequence of SEQ ID NO: 81, a first light chain that has the amino acid sequence of SEQ ID NO: 86, and a second light chain that has the amino acid sequence of SEQ ID NO: 82, or
ai) a first heavy chain that has the amino acid sequence of SEQ ID NO: 89, a second heavy chain that has the amino acid sequence of SEQ ID NO: 87, a first light chain that has the amino acid sequence of SEQ ID NO: 90, and a second light chain that has the amino acid sequence of SEQ ID NO: 88, or
aj) a first heavy chain that has the amino acid sequence of SEQ ID NO: 81, a second heavy chain that has the amino acid sequence of SEQ ID NO: 87, a first light chain that has the amino acid sequence of SEQ ID NO: 92, and a second light chain that has the amino acid sequence of SEQ ID NO: 88.

47. An antibody according to any one of embodiments 1 to 46 for use as a medicament.

48. An antibody according to any one of embodiments 1 to 46 for use in the treatment of an ocular vascular disease.

49. Use of an antibody according to any one of embodiments 1 to 46 for the treatment of eye diseases, especially of ocular vascular diseases.

50. An antibody according to any one of embodiments 1 to 46 for use in treating an eye disease.

51. An antibody according to any one of embodiments 1 to 46 for use in treating eye diseases, especially ocular vascular diseases.

52. A method of treating an individual having an ocular vascular disease comprising administering to the individual an effective amount of an antibody according to any one of embodiments 1 to 46.

53. A pharmaceutical formulation comprising the antibody according to any one of embodiments 1 to 46.

54. A pharmaceutical formulation comprising the antibody according to any one of embodiments 1 to 46 for use in the treatment of ocular vascular diseases.

55. Use of the antibody according to any one of embodiments 1 to 46 for the manufacture of a medicament for the treatment of ocular vascular diseases.

56. A method of treatment of patient suffering from ocular vascular diseases by administering the antibody according to any one of embodiments 1 to 46 to a patient in the need of such treatment.

57. The pharmaceutical formulation according to any one of embodiments 53 to 54, wherein the antibody is administered via intravitreal application.

58. The administering according to any one of embodiments 56 to 57, wherein the administering is an intravitreal application.

59. A nucleic acid encoding the antibody according to any one of embodiments 1 to 46.

60. A cell comprising one or more nucleic acids encoding the antibody according to any one of embodiments 1 to 46.

61. A method for producing an antibody according to any one of embodiments 1 to 46, wherein the method comprises the following steps:
a) optionally transfecting a mammalian cell with one or more nucleic acids encoding the antibody according to any one of embodiments 1 to 46,
b) cultivating the cell to express the antibody, and
c) recovering the antibody from the cell or the cultivation medium and thereby producing the antibody.

V. EXAMPLES

The following are examples of the methods and compositions of the invention. It is understood that various other embodiments may be practiced, given the general description provided above.

Material and Methods

Cloning:

Point mutations have been introduced using the QuikChange® II XL Site-Directed Mutagenesis Kit (Agilent Technologies). Few single colonies were picked and transferred into 4 ml of LB-Amp medium and cultured at 37° C. for 16-18 hours. By centrifugation 2 ml thereof were harvested followed by a plasmid preparation with the High Pure Plasmid Isolation Kit (Roche Diagnostics GmbH, Mannheim, Germany) according to the manufacturer's instructions. After confirmation by sequencing, the plasmids were retransformed in *E. coli* cells (Agilent Technologies). A single colony was transferred into 2 ml of LB-Amp medium and cultured at 37° C. for 6-8 hours. Thereafter 200 µl of this culture was used to inoculate 150 ml LB-Amp medium in a shaker flask. The culture was incubated at 37° C., 300 rpm overnight and subsequently the cells were harvested by centrifugation. Plasmid preparation was performed with the HiSpeed® Plasmid Maxi Kit (Qiagen) according to the manufacturer's instructions.

The mutated CrossFabs have been used as template for cloning via restriction sides by changing the VH-region respectively the VL-region in the CrossFabs and CrossMab-backbone-plasmids. After digestion of the template and backbone-plasmids with the same pair of restriction-enzymes the mixture has been added to a 1% agarose-gel to isolate the donor-DNA (VH- or VL-region) and the acceptor-DNA (plasmid backbone). Thereafter the agarose-pieces have been purified with the High Pure PCR Product Purification Kit (Roche Diagnostics GmbH, Mannheim, Germany). Afterwards the acceptor-DNA has been dephosphorylated by rAPid Alkaline Phosphatase (Roche Diagnostics GmbH, Mannheim, Germany) and then acceptor-DNA and donor-DNA were ligated by using the Rapid DNA Ligation Kit (Roche Diagnostics GmbH, Mannheim, Germany). The ligated DNA has been transformed into *E. coli* cells (Agilent Technologies).

Transient Expression

HEK293F Cells (Invitrogen) have been passaged, by dilution, at least four times (volume 30 ml) after thawing in a 125 ml shake flask (Incubate/Shake at 37° C., 7% $CO_2$, 85% humidity, 135 rpm).

The cells were expanded to $3 \times 10^5$ cells/ml in 250 ml volume. Three days later, cells have been split and newly seeded at a density of $7 \times 10^5$ cells/ml in a 250 ml volume in a 1 liter shake flask. Transfection was done 24 hours later at a cell density around $1.4$-$2.0 \times 10^6$ cells/ml.

Before transfection 250 µg plasmid-DNA (122 µg light chain plasmid and 128 µg heavy chain plasmid) was diluted in a final volume of 10 ml with pre-heated (water bath; 37° C.) Opti-MEM™ medium (Gibco). The solution was gentle mixed and incubated at room temperature for not longer than 5 min. Thereafter 333.3 µl 293-free transfection reagent was added to the DNA-OptiMEM™-solution. The solution was gently mixed and incubated at room temperature for 15-20 minutes. The whole volume of the mixture was added to 1 L shake flask with 250 ml HEK-cell-culture-volume. The flask was incubated/shaken at 37° C., 7% $CO_2$, 85% humidity, 135 rpm for 6 or 7 days. The supernatant was harvested by a first centrifugation-step at 2,000 rpm, 4° C., for 10 minutes. The supernatant was transferred to a new centrifugation-flask for a second centrifugation step at 4,000 rpm, 4° C., for 20 minutes. Thereafter the cell-free-supernatant was filtered through a 0.22 µm bottle-top-filter and stored in a freezer (−20° C.).

Purification

Antibodies and CrossMAbs$^{CH1-CL}$ were purified from cell culture supernatants by affinity chromatography using Mab-Select™ Sure-Sepharose™ (GE Healthcare, Sweden) whereas Fabs, CrossFabs and Ang2VEGF CrossMAbs with AAA mutation were purified using KappaSelect-Agarose (for non Fc-region-containing binding domains) (GE Healthcare, Sweden), followed by hydrophobic interaction chromatography using butyl-Sepharose® (GE Healthcare, Sweden) and Superdex® 200 size exclusion (GE Healthcare, Sweden) chromatography.

Briefly, antibodies and CrossMAbs were captured from sterile filtered cell culture supernatants on a MabSelect™ SuRe™ resin equilibrated with PBS buffer (10 mM $Na_2HPO_4$, 1 mM $KH_2PO_4$, 137 mM NaCl and 2.7 mM KCl, pH 7.4), washed with equilibration buffer and eluted with 25 mM sodium citrate at pH 3.0. The Fabs were captured on a KappaSelect resin equilibrated with 25 mM Tris, 50 mM NaCl, pH 7.2, washed with equilibration buffer and eluted with 25 mM sodium citrate pH 2.9. The eluted antibody or Fab containing fractions were pooled and neutralized with 2 M Tris, pH 9.0. The antibody/Fab pools were prepared for hydrophobic interaction chromatography by adding 1.6 M ammonium sulfate solution to a final concentration of 0.8 M ammonium sulfate. The pH was adjusted to pH 5.0 using acetic acid. After equilibration of the butyl-Sepharose resin with 35 mM sodium acetate, 0.8 M ammonium sulfate, pH 5.0, the antibodies were applied to the resin, washed with equilibration buffer and eluted using a linear gradient from 0 to 35 mM sodium acetate pH 5.0. The bispecific antibody/antibody or Fab containing fractions were pooled and further purified by size exclusion chromatography using a Superdex® 200 26/60 GL (GE Healthcare, Sweden) column equilibrated with 20 mM histidine, 140 mM NaCl, pH 6.0. The antibody or Fab, respectively, containing fractions were pooled, concentrated to the required concentration using Vivaspin® ultrafiltration devices (Sartorius Stedim Biotech S.A., France) and stored at −80° C.

CE-SDS Analytics

Purity and antibody integrity were analyzed after each purification step by CE-SDS using microfluidic Labchip technology (Caliper Life Science, USA). Therefore 5 µl of analyte solution was prepared using the HT Protein Express Reagent Kit according to the manufacturer's instructions and analyzed on LabChip GXII system using a HT Protein Express Chip. Data were analyzed using LabChip GX Software.

Example 1

Crossed Antibodies (CrossMabs) and Crossed Antibody Fab Fragments (CrossFabs) that Bind to Angiopoietin 2 (ANG2).

Crossed antibodies (CrossMab) or crossed fragments antigen binding (CrossFabs) were generated by cloning as described in the methods section by molecular biology techniques and expressed transiently in HEK293 cells as described above.

A general scheme of the generated antibodies and Fabs with specific point mutations in the CDRs is given in Table 1. The crossed antibodies and crossed Fabs were expressed using expression plasmids containing the nucleic acids encoding the amino acid sequences as shown in Table 14.

TABLE 14

Amino acid sequences of anti-ANG2 CrossFabs as reported herein.

| molecule | mutation VH | VH-X Sequence ID | mutation VL | VL-X Sequence ID |
|---|---|---|---|---|
| XAng2-0009 | wt | 46 | wt | 49 |
| XAng2-0015 | S108P | 57 | wt | 49 |
| XAng2-0017 | S-S bridge S55C-D100BC | 59 | wt | 49 |
| XAng2-0021 | G100JA | 60 | wt | 49 |
| XAng2-0026 | T28N, T30A | 62 | wt | 49 |
| XAng2-0029 | S108P, G100JA | 65 | wt | 49 |
| XAng2-0033 | T28N, S108P, G100JA | 68 | wt | 49 |
| XAng2-0041 | T30A, T28N, S108P, G100JA | 47 | wt | 49 |
| XAng2-0075 | T30A, T28N, S108P, G100JA, D100BS | 48 | D50T | 50 |
| XAng2-0090 | T30A, T28N, S108P, G100JA | 47 | D50T | 50 |
| XAng2-0098 | wt | 51 | wt | 49 |
| XAng2-0099 | G100JA, S108P, T28N, T30A | 52 | wt | 49 |
| XAng2-0100 | G100JA, S108P, T28N, T30A | 52 | D50T | 50 |
| XAng2-0101 | G100JA, S108P, T28N, T30A, D100BE | 53 | D50T | 50 |
| Xang2-0154 | wt | 46 | wt | 77 |
| XAng2-0155 | T30A, T28N, S108P, G100JA | 47 | D50T | 78 |
| XAng2-0156 | T30A, T28N, S108P, G100JA, D100BS | 48 | D50T | 78 |
| XAng2-0157 | wt (Ang2i-LC06) | 46 | D50T | 50 |

Example 2

Crossed Bivalent Bispecific Antibodies (CrossMabs) that Bind to Angiopoietin-2 (ANG2) and Vascular Endothelial Growth Factor (VEGF), with CL-CH1 Domain Exchange (CrossMab$^{CH1/CL}$) in the ANG2 Binding ANG2-VEGF CrossMab$^{CH1-CL}$ with CH1-CL crossover in the ANG2 Fab arm were generated by cloning as described above by molecular biology techniques and expressed transiently in HEK293 cells as described above.

A general scheme of the generated ANG2-VEGF CrossMabs$^{CH1-CL}$ with specific point mutations in the CDRs is given in Table 15. The ANG2-VEGF CrossMabs$^{CH1-CL}$ were expressed using expression plasmids containing the nucleic acids encoding the amino acid sequences as shown in Table 15.

TABLE 15

Amino acid sequences of anti-ANG2/VEGF bispecific bivalent CrossMabs$^{CH1-CL}$ as reported herein.

| | ANG2 binding site | | | | VEGF binding site | |
|---|---|---|---|---|---|---|
| Molecule | Mutation VH | <VH-CL-CH2-CH3> Sequence ID # | Mutation VL | <VL-CH1> Sequence ID # | HC Sequence ID # | LC Sequence ID # |
| Xang2-0162 | wt | 79 | wt | 80 | 81 | 82 |
| Xang2-0163 | T30A, T28N, S108P, G100JA | 83 | D50T | 84 | 81 | 82 |
| Xang2-0164 | T30A, T28N, S108P, G100JA, D100BS | 85 | D50T | 86 | 81 | 82 |
| Xang2-0165 | T30A, T28N, S108P, G100JA | 89 | D50T | 90 | 87 | 88 |
| Xang2-0166 | T30A, T28N, S108P, G100JA, D100BS | 91 | D50T | 92 | 87 | 88 |
| Xang2-0167 | wt | 93 | wt | 94 | 87 | 88 |

For all constructs knob-into-hole heterodimerization technology was used with a typical knob (T366W) mutation in the first CH3 domain and the corresponding hole mutations (T366S, L368A and Y407V) in the second CH3 domain (as well as two additional introduced cysteine residues S354C/Y349C) (contained in the respective corresponding heavy chain (HC) sequences depicted above).

Example 3

Transfection and Transient Expression of the ANG2 Binding CrossFabs, Antibodies and Ang2-VEGF CrossMab$^{CH1-CL}$ in HEK Cells Transient expression of antibodies in suspension-adapted HEK293F (FreeStyle 293-F cells; Invitrogen) cells with Transfection Reagent 293-Free™ (Novagen).

Cells have been passaged, by dilution, at least four times (volume 30 ml) after thawing in a 125 ml shake flask (Incubate/Shake at 37° C., 7% CO$_2$, 85% humidity, 135 rpm).

The cells were expanded to 3×10$^5$ cells/ml in 250 ml volume. Three days later, cells have been split and new seeded with a density of 7×10$^5$ cells/ml in a 250 ml volume in a 1 liter shake flask. Transfection will be 24 hours later at a cell density around 1.4-2.0×10$^6$ cells/ml.

Before transfection dilute 250 μg plasmid-DNA (122 μg light and 128 μg heavy chain) in a final volume of 10 ml with pre-heated (water bath; 37° C.) Opti-MEM™ (Gibco). Mix solution gentle and incubate at room temperature for not longer than 5 min. Then add 333.3 μl 293-free transfection reagent to DNA-OptiMEM™ solution. Mix gently and incubate at room temperature for 15-20 minutes. Add whole volume of mixture to 1 L shake flask with 250 ml HEK-cell-culture-volume.

Incubate/Shake at 37° C., 7% CO$_2$, 85% humidity, 135 rpm for 6 or 7 days.

Harvest supernatant by a first centrifugation-step at 2,000 rpm, 4° C., for 10 minutes. Then transfer the supernatant in a new centrifugation-flask for a second centrifuge at 4,000 rpm, 4° C., for 20 minutes. Thereafter the cell-free-supernatant is filtered through a 0.22 μm bottle-top-filter and stored in a freezer (−20° C.).

Example 4

Fab Purification from HEK Supernatant

The antibody-containing cell culture supernatants were filtered and purified by two chromatographic steps. The CrossFabs and CrossMAbs with AAA mutation were captured by affinity chromatography using KappaSelect (GE Healthcare) and polished by an additional HIC and SEC chromatography step. For details, see Material & Methods above.

Example 5

CrossMab$^{CH1-CL}$ Purification from HEK Supernatant

The culture supernatants were filtered and purified by three chromatographic steps. The antibodies were captured by affinity chromatography using HiTrap® MabSelect™ SuRe™ (GE Healthcare) and polished with a HIC and SEC chromatography step. The antibody containing solutions were concentrated with an Ultrafree-CL centrifugal filter unit equipped with a Biomax™-SK membrane (Millipore, Billerica, Mass.) and stored at −80° C.

Example 6

Analytics of CrossFab and CrossMAb$^{CH1-CL}$ Preparations

The protein concentration of the preparations was determined by measuring the optical density (OD) at 280 nm, using the molar extinction coefficient calculated on the basis of the amino acid sequence.

Purity and integrity of the antibodies were analyzed by CE-SDS using a LabChip GX II (PerkinElmer) with Protein Express Chip and HT Protein Express Reagents Kit.

Aggregate content of antibody preparations was determined by high-performance SEC using a TSK-GEL G3000SWXL using 2×PBS, pH 7.4 as running buffer or by high-performance SEC using a BioSuite High Resolution SEC, 250 Å, 5 μm analytical size-exclusion column (Waters GmbH) using 200 mM $K_2HPO_4/KH_2PO_4$, 250 mM KCl, pH 7.0 as running buffer.

Example 7

Preparation of Fab Fragment from an Antibody and Analytics 12 mg antibody (1 mg/ml in 20 mM Histidine, 140 mM NaCl, pH 6.0) were incubated with 240 μl L-cysteine solution (Merck Millipore; 250 mM in 20 mM Histidine, 140 mM NaCl, pH 6.0) and 327 μl Papain (Roche Life Science; 0.001 U/mg antibody) for 120 min at 37° C. After cleavage, affinity chromatography using HiTrap® MabSelect™ SuRe™ (GE Healthcare) equilibrated with PBS (1 mM $KH_2PO_4$, 10 mM $Na_2HPO_4$, 137 mM NaCl, 2.7 mM KCl), pH 7.4 was used for removal of intact IgG and Fc fragment. Subsequently, flow-through of MabSelect™ SuRe™ chromatography was further purified using size exclusion chromatography on Superdex 200™ (GE Healthcare) as second purification step. The size exclusion chromatography was performed in 20 mM histidine buffer, 0.14 M NaCl, pH 6.0. The Fab fragment containing solutions were concentrated with an Ultrafree-CL centrifugal filter unit equipped with a Biomax™-SK membrane (Millipore, Billerica, Mass.) and stored at −80° C.

The protein concentrations of the Fab-fragments were determined by measuring the optical density (OD) at 280 nm, using the molar extinction coefficient calculated on the basis of the amino acid sequence.

Purity and integrity of the Fab-fragments were analyzed by SDS-PAGE (NuPAGE® 4-12% Bis-Tris Gel, Invitrogen) in the presence and absence of a reducing agent (5 mM 1. 4-dithiotreitol) and staining with SimplyBlue™ SafeStain (Invitrogen).

Aggregate content of Fab preparations was determined by high-performance SEC using a BioSuite™ High Resolution SEC, 250 Å, 5 μm analytical size-exclusion column (Waters GmbH) using 200 mM $K_2HPO_4/KH_2PO_4$, 250 mM KCl, pH 7.0 as running buffer.

Example 8

ANG2 Binding Kinetics and Cross-Reactivity of Maturated Cross-Fabs

Binding of the maturated Cross-Fabs to human ANG2-RBD-Fc-region fusion was investigated by surface plasmon resonance using a BIACORE® T200 instrument (GE Healthcare). Around 4000 RU of anti-human antibody (10 μg/ml anti-human IgG (Fc) antibody; ordering code BR-1008-39; GE Healthcare) were coupled on a Series S CM5 chip (GE Healthcare BR-1005-30) at pH 5.0 by using an amine coupling kit supplied by the GE Healthcare. HBS-N (10 mM HEPES, 150 mM NaCl pH 7.4, GE Healthcare) was used as running buffer during the immobilization procedure. For the following kinetic characterization, sample and running buffer was HBS-P (10 mM HEPES, 150 mM NaCl pH 7.4, 0.05% Surfactant P20; GE Healthcare). The flow cell was set to 25° C.—and the sample block was set to 12° C.—and primed with running buffer twice prior to kinetic characterization.

Human or cynomolgus ANG2-RBD-Fc-region fusion was captured by injecting a 1 μg/ml solution for 30 sec. at a flow rate of 5 μl/min. Association was measured by injection of the Cross-Fabs in various concentrations in solution for 90 sec. at a flow rate of 90 μl/min starting with 300 nM in serial 1:3 dilutions. The dissociation phase was monitored for up to 600 sec. and triggered by switching from the sample solution to running buffer. All surfaces were regenerated by 60 sec. washing with a 3 M $MgCl_2$ solution at a flow rate of 5 μl/min. Bulk refractive index differences were corrected by subtracting the response obtained from an anti-human IgG antibody (Fc) surface. Blank injections were also subtracted (=double referencing). For calculation of KD and other kinetic parameters the Langmuir 1:1 model was used.

Example 9

Biological Activity

The method determines the capacity of an antibody to inhibit binding of ANG2 to its receptor Tie2. For expression of the Tie2 receptor tyrosine kinase on the cell surface the HEK293 cell line, a human embryonic kidney cell line, was stably transfected with the expression vector for human Tie2 resulting in the cell line HEK293 Tie2.

The cells are stimulated with ANG2 that binds to the Tie2 receptor and induces the autophosphorylation of the receptor. The binding to Tie2 can be inhibited by addition of an anti-ANG2 antibody as reported herein. The grade of phosphorylation is analyzed by an ELISA. The OD values correlate with the amount of phosphorylated Tie2 and are plotted against the antibody concentrations. The $EC_{50}$ value is determined and reported relative to the reference standard on the same plate as relative biological activity (RBA).

A multi-well plate was coated with antibody against the human Tie2 receptor (100 µl of 10 µg/ml; R&D Systems, Cat# MAB3132; 96 well Maxi Sorp™ immuno plate, incubated overnight at room temperature; coated plates were washed three times, volume 250 µl; thereafter incubated with 200 µl blocking 1-2 hours at room temperature).

Separately the HEK293 Tie2 cells (40 µl; 5×10$^6$ cells/ml; DMEM/F12) were added to a pre-incubated mixture (80 µl) of dilution series of the antibody in question and ANG2 (R&D Systems, Cat#623-CF). After 10 minutes the cells were lysed (60 µl lysis buffer added; incubated for 15 min.) and the cell lysate was transferred to the coated plate for the ELISA.

The Tie2 receptor of the lysate binds to the capture anti-Tie2 antibody (100 µl lysate; incubated for 90 min. at RT). The phosphorylated tyrosins on the Tie2 receptor were detected by anti-phosphotyrosine antibody conjugated to biotin (100 µl; 0.3 µg/ml anti-phosphotyrosine antibody, clone 4G10®, biotin conjugate, Upstate, Cat#16-103; incubated for 60 min. at RT). Biotin residues were bound by the streptavidin-horseradish peroxidase conjugate (100 µl; 100 mU/ml; Roche Diagnostics GmbH, Mannheim, Germany, Cat#11089153001; incubated for 30 min. at RT). The peroxidase substrate TMB (100 µl; Roche Diagnostics GmbH, Mannheim, Germany, Cat#11835033001) was added and the optical density was measured after 5-10 min at 450 nm.

Example 10

Chemical Degradation Test

Samples were split into three aliquots and re-buffered into 20 mM His/His*HCl, 140 mM NaCl, pH 6.0 or into PBS, respectively, and stored at 40° C. (His/NaCl) or 37° C. (PBS). A control sample was stored at −80° C.

After incubation ended, samples were analyzed for relative active concentration (BIAcore®), aggregation (SEC) and fragmentation (capillary electrophoresis or SDS-PAGE) and compared with the untreated control.

Example 11

Thermal Stability

Samples were prepared at a concentration of 1 mg/mL in 20 mM Histidine/Histidine chloride, 140 mM NaCl, pH 6.0, transferred into an optical 384-well plate by centrifugation through a 0.4 µm filter plate and covered with paraffin oil. The hydrodynamic radius was measured repeatedly by dynamic light scattering on a DynaPro® Plate Reader (Wyatt) while the samples were heated with a rate of 0.05° C./min from 25° C. to 80° C.

Alternatively, samples were transferred into a 10 µL micro-cuvette array and static light scattering data as well as fluorescence data upon excitation with a 266 nm laser were recorded with an Optim® 1000 instrument (Avacta Inc.), while they were heated at a rate of 0.1° C./min from 25° C. to 90° C.

The aggregation onset temperature is defined as the temperature at which the hydrodynamic radius (DLS) or the scattered light intensity (Optim® 1000) starts to increase.

Alternatively, samples were transferred in a 9 µL multi-cuvette array. The multi-cuvette array was heated from 35° C. to 90° C. at a constant rate of 0.1° C./minute in an Optim® 1000 instrument (Avacta Analytical Inc.). The instrument continuously records the intensity of scattered light of a 266 nm laser with a data point approximately every 0.5° C. Light scattering intensities were plotted against the temperature. The aggregation onset temperature (T_agg) is defined as the temperature at which the scattered light intensity begins to increase.

The melting temperature is defined as the inflection point in fluorescence intensity vs. wavelength graph.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. An antibody that specifically binds to human ANG2, wherein the antibody comprises a variable heavy (VH) domain comprising (a) a HVR-H1 comprising the amino acid sequence of SEQ ID NO: 20, (b) a HVR-H2 comprising the amino acid sequence of SEQ ID NO: 21, (c) a HVR-H3 comprising the amino acid sequence of SEQ ID NO: 23, and a variable light (VL) domain comprising (d) a HVR-L1 comprising the amino acid sequence of SEQ ID NO: 25; (e) a HVR-L2 comprising the amino acid sequence of SEQ ID NO: 26; and (f) a HVR-L3 comprising the amino acid sequence of SEQ ID NO: 27.

2. The antibody according to claim 1, wherein the antibody is a bispecific antibody.

3. The antibody according to claim 1 or 2, wherein the antibody is of the human subclass IgG1 or the human subclass IgG4.

4. The antibody according to claim 1 or 2, wherein the antibody blocks the biological activity of human ANG2 by inhibiting the binding of human ANG2 to human Tie2 receptor.

5. A pharmaceutical formulation comprising an antibody according to claim 1 or 2 and optionally a pharmaceutically acceptable carrier.

6. The pharmaceutical formulation according to claim 5, further comprising an anti-IL-1beta antibody or an anti-PDGF-B antibody.

* * * * *

SEQUENCE LISTING

```
<160> NUMBER OF SEQ ID NOS: 94

<210> SEQ ID NO 1
<211> LENGTH: 129
<212> TYPE: PRT
<213> ORGANISM: Artificial sequence
<220> FEATURE:
<223> OTHER INFORMATION: Ang2 LC10 VH

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80
```

```
Met Glu Leu Ser Arg Leu Arg Ser Asp Asp Thr Ala Val Tyr Tyr Cys
                85                  90                  95
Ala Arg Ser Pro Asn Pro Tyr Tyr Tyr Asp Ser Ser Gly Tyr Tyr Tyr
            100                 105                 110
Pro Gly Ala Phe Asp Ile Trp Gly Gln Gly Thr Met Val Thr Val Ser
        115                 120                 125
Ser

<210> SEQ ID NO 2
<211> LENGTH: 7
<212> TYPE: PRT
<213> ORGANISM: Artificial sequence
<220> FEATURE:
<223> OTHER INFORMATION: Ang2 LC10 HVR-H1

<400> SEQUENCE: 2

Gly Tyr Thr Phe Thr Gly Tyr
1               5

<210> SEQ ID NO 3
<211> LENGTH: 3
<212> TYPE: PRT
<213> ORGANISM: Artificial sequence
<220> FEATURE:
<223> OTHER INFORMATION: Ang2 LC10 HVR-H2s

<400> SEQUENCE: 3

Asn Ser Gly
1

<210> SEQ ID NO 4
<211> LENGTH: 17
<212> TYPE: PRT
<213> ORGANISM: Artificial sequence
<220> FEATURE:
<223> OTHER INFORMATION: Ang2 LC10 HVR-H2

<400> SEQUENCE: 4

Trp Ile Asn Pro Asn Ser Gly Gly Thr Asn Tyr Ala Gln Lys Phe Gln
1               5                   10                  15
Gly

<210> SEQ ID NO 5
<211> LENGTH: 18
<212> TYPE: PRT
<213> ORGANISM: Artificial sequence
<220> FEATURE:
<223> OTHER INFORMATION: Ang2 LC10 HVR-H3

<400> SEQUENCE: 5

Pro Asn Pro Tyr Tyr Tyr Asp Ser Ser Gly Tyr Tyr Tyr Pro Gly Ala
1               5                   10                  15
Phe Asp

<210> SEQ ID NO 6
<211> LENGTH: 110
<212> TYPE: PRT
<213> ORGANISM: Artificial sequence
<220> FEATURE:
<223> OTHER INFORMATION: Ang2 LC10 VL

<400> SEQUENCE: 6

Ser Tyr Val Leu Thr Gln Pro Pro Ser Val Ser Val Ala Pro Gly Gln
```

```
                1               5                  10                 15
            Thr Ala Arg Ile Thr Cys Gly Gly Asn Asn Ile Gly Ser Lys Ser Val
                            20                 25                 30
            His Trp Tyr Gln Gln Lys Pro Gly Gln Ala Pro Val Leu Val Val Tyr
                        35                 40                 45
            Asp Asp Ser Asp Arg Pro Ser Gly Ile Pro Glu Arg Phe Ser Gly Ser
                50                 55                 60
            Asn Ser Gly Asn Thr Ala Thr Leu Thr Ile Ser Arg Val Glu Ala Gly
             65                 70                 75                 80
            Asp Glu Ala Asp Tyr Tyr Cys Gln Val Trp Asp Ser Ser Ser Asp His
                            85                 90                 95
            Trp Val Phe Gly Gly Gly Thr Lys Leu Thr Val Leu Ser Ser
                        100                105                110
```

<210> SEQ ID NO 7
<211> LENGTH: 7
<212> TYPE: PRT
<213> ORGANISM: Artificial sequence
<220> FEATURE:
<223> OTHER INFORMATION: Ang2 LC10 HVR-L1

<400> SEQUENCE: 7

```
Asn Asn Ile Gly Ser Lys Ser
1               5
```

<210> SEQ ID NO 8
<211> LENGTH: 3
<212> TYPE: PRT
<213> ORGANISM: Artificial sequence
<220> FEATURE:
<223> OTHER INFORMATION: Ang2 LC10 HVR-L2

<400> SEQUENCE: 8

```
Asp Asp Ser
1
```

<210> SEQ ID NO 9
<211> LENGTH: 8
<212> TYPE: PRT
<213> ORGANISM: Artificial sequence
<220> FEATURE:
<223> OTHER INFORMATION: Ang2 LC10 HVR-L3

<400> SEQUENCE: 9

```
Trp Asp Ser Ser Ser Asp His Trp
1               5
```

<210> SEQ ID NO 10
<211> LENGTH: 129
<212> TYPE: PRT
<213> ORGANISM: Artificial sequence
<220> FEATURE:
<223> OTHER INFORMATION: Ang2 LC06 VH

<400> SEQUENCE: 10

```
                1               5                  10                 15
            Gln Val Gln Leu Val Gln Ser Gly Ala Glu Val Lys Lys Pro Gly Ala
                            20                 25                 30
            Ser Val Lys Val Ser Cys Lys Ala Ser Gly Tyr Thr Phe Thr Gly Tyr
                        35                 40                 45
            Tyr Met His Trp Val Arg Gln Ala Pro Gly Gln Gly Leu Glu Trp Met
            Gly Trp Ile Asn Pro Asn Ser Gly Gly Thr Asn Tyr Ala Gln Lys Phe
```

```
                 50                  55                  60
Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Pro Asn Pro Tyr Tyr Asp Ser Ser Gly Tyr Tyr
            100                 105                 110

Pro Gly Ala Phe Asp Ile Trp Gly Gln Gly Thr Met Val Thr Val Ser
        115                 120                 125

Ser

<210> SEQ ID NO 11
<211> LENGTH: 7
<212> TYPE: PRT
<213> ORGANISM: Artificial sequence
<220> FEATURE:
<223> OTHER INFORMATION: Ang2 LC06 HVR-H1

<400> SEQUENCE: 11

Gly Tyr Thr Phe Thr Gly Tyr
1               5

<210> SEQ ID NO 12
<211> LENGTH: 3
<212> TYPE: PRT
<213> ORGANISM: Artificial sequence
<220> FEATURE:
<223> OTHER INFORMATION: Ang2 LC06 HVR-H2s

<400> SEQUENCE: 12

Asn Ser Gly
1

<210> SEQ ID NO 13
<211> LENGTH: 17
<212> TYPE: PRT
<213> ORGANISM: Artificial sequence
<220> FEATURE:
<223> OTHER INFORMATION: Ang2 LC06 HVR-H2

<400> SEQUENCE: 13

Trp Ile Asn Pro Asn Ser Gly Gly Thr Asn Tyr Ala Gln Lys Phe Gln
1               5                   10                  15

Gly

<210> SEQ ID NO 14
<211> LENGTH: 18
<212> TYPE: PRT
<213> ORGANISM: Artificial sequence
<220> FEATURE:
<223> OTHER INFORMATION: Ang2 LC06 HVR-H3

<400> SEQUENCE: 14

Pro Asn Pro Tyr Tyr Tyr Asp Ser Ser Gly Tyr Tyr Tyr Pro Gly Ala
1               5                   10                  15

Phe Asp

<210> SEQ ID NO 15
<211> LENGTH: 108
<212> TYPE: PRT
<213> ORGANISM: Artificial sequence
<220> FEATURE:
<223> OTHER INFORMATION: Ang2 LC06 VL
```

```
<400> SEQUENCE: 15

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Tyr Val Phe Gly Thr Gly Thr Lys Val Thr Val Leu
            100                 105

<210> SEQ ID NO 16
<211> LENGTH: 7
<212> TYPE: PRT
<213> ORGANISM: Artificial sequence
<220> FEATURE:
<223> OTHER INFORMATION: Ang2 LC06 HVR-L1

<400> SEQUENCE: 16

Asn Asn Ile Gly Ser Lys Ser
1               5

<210> SEQ ID NO 17
<211> LENGTH: 3
<212> TYPE: PRT
<213> ORGANISM: Artificial sequence
<220> FEATURE:
<223> OTHER INFORMATION: Ang2 LC06 HVR-L2

<400> SEQUENCE: 17

Asp Asp Ser
1

<210> SEQ ID NO 18
<211> LENGTH: 8
<212> TYPE: PRT
<213> ORGANISM: Artificial sequence
<220> FEATURE:
<223> OTHER INFORMATION: Ang2 LC06 HVR-L3

<400> SEQUENCE: 18

Trp Asp Ser Ser Ser Asp His Tyr
1               5

<210> SEQ ID NO 19
<211> LENGTH: 129
<212> TYPE: PRT
<213> ORGANISM: Artificial sequence
<220> FEATURE:
<223> OTHER INFORMATION: Ang2 LC10 wt + G114A, S360P, T28N, T30A (HC) VH

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30
```

```
Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Pro Asn Pro Tyr Tyr Tyr Asp Ser Pro Gly Tyr Tyr Tyr
                100                 105                 110

Pro Ala Ala Phe Asp Ile Trp Gly Gln Gly Thr Met Val Thr Val Ser
            115                 120                 125

Ser
```

<210> SEQ ID NO 20
<211> LENGTH: 7
<212> TYPE: PRT
<213> ORGANISM: Artificial sequence
<220> FEATURE:
<223> OTHER INFORMATION: Ang2 LC10 wt + G114A, S360P, T28N, T30A (HC) HVR-H1

<400> SEQUENCE: 20

```
Gly Tyr Asn Phe Ala Gly Tyr
 1               5
```

<210> SEQ ID NO 21
<211> LENGTH: 3
<212> TYPE: PRT
<213> ORGANISM: Artificial sequence
<220> FEATURE:
<223> OTHER INFORMATION: Ang2 LC10 wt + G114A, S360P, T28N, T30A (HC) HVR-H2s

<400> SEQUENCE: 21

```
Asn Ser Gly
 1
```

<210> SEQ ID NO 22
<211> LENGTH: 17
<212> TYPE: PRT
<213> ORGANISM: Artificial sequence
<220> FEATURE:
<223> OTHER INFORMATION: Ang2 LC10 wt + G114A, S360P, T28N, T30A (HC) HVR-H2

<400> SEQUENCE: 22

```
Trp Ile Asn Pro Asn Ser Gly Gly Thr Asn Tyr Ala Gln Lys Phe Gln
 1               5                  10                  15

Gly
```

<210> SEQ ID NO 23
<211> LENGTH: 18
<212> TYPE: PRT
<213> ORGANISM: Artificial sequence
<220> FEATURE:
<223> OTHER INFORMATION: Ang2 LC10 wt + G114A, S360P, T28N, T30A (HC) HVR-H3

<400> SEQUENCE: 23

```
Pro Asn Pro Tyr Tyr Tyr Asp Ser Pro Gly Tyr Tyr Tyr Pro Ala Ala
 1               5                  10                  15

Phe Asp
```

-continued

```
<210> SEQ ID NO 24
<211> LENGTH: 110
<212> TYPE: PRT
<213> ORGANISM: Artificial sequence
<220> FEATURE:
<223> OTHER INFORMATION: Ang2 LC10 wt + G114A, S360P, T28N, T30A (HC) VL

<400> SEQUENCE: 24

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser
            100                 105                 110

<210> SEQ ID NO 25
<211> LENGTH: 7
<212> TYPE: PRT
<213> ORGANISM: Artificial sequence
<220> FEATURE:
<223> OTHER INFORMATION: Ang2 LC10 wt + G114A, S360P, T28N, T30A (HC)
      HVR-L1

<400> SEQUENCE: 25

Asn Asn Ile Gly Ser Lys Ser
1               5

<210> SEQ ID NO 26
<211> LENGTH: 3
<212> TYPE: PRT
<213> ORGANISM: Artificial sequence
<220> FEATURE:
<223> OTHER INFORMATION: Ang2 LC10 wt + G114A, S360P, T28N, T30A (HC)
      HVR-L2

<400> SEQUENCE: 26

Asp Asp Ser
1

<210> SEQ ID NO 27
<211> LENGTH: 8
<212> TYPE: PRT
<213> ORGANISM: Artificial sequence
<220> FEATURE:
<223> OTHER INFORMATION: Ang2 LC10 wt + G114A, S360P, T28N, T30A (HC)
      HVR-L3

<400> SEQUENCE: 27

Trp Asp Ser Ser Ser Asp His Trp
1               5

<210> SEQ ID NO 28
<211> LENGTH: 129
<212> TYPE: PRT
<213> ORGANISM: Artificial sequence
```

```
<220> FEATURE:
<223> OTHER INFORMATION: Ang2 LC10 wt + G114A, S360P, T28N, T30A (HC) +
      D50T (LC) VH

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Pro Gly Tyr Tyr Tyr
            100                 105                 110

Pro Ala Ala Phe Asp Ile Trp Gly Gln Gly Thr Met Val Thr Val Ser
        115                 120                 125

Ser

<210> SEQ ID NO 29
<211> LENGTH: 7
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) HVR-H1

<400> SEQUENCE: 29

Gly Tyr Asn Phe Ala Gly Tyr
1               5

<210> SEQ ID NO 30
<211> LENGTH: 3
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) HVR-H2s

<400> SEQUENCE: 30

Asn Ser Gly
1

<210> SEQ ID NO 31
<211> LENGTH: 17
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) HVR-H2

<400> SEQUENCE: 31

Trp Ile Asn Pro Asn Ser Gly Gly Thr Asn Tyr Ala Gln Lys Phe Gln
1               5                   10                  15

Gly

<210> SEQ ID NO 32
<211> LENGTH: 18
```

<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) HVR-H3

<400> SEQUENCE: 32

Pro Asn Pro Tyr Tyr Tyr Asp Ser Pro Gly Tyr Tyr Tyr Pro Ala Ala
1               5                   10                  15

Phe Asp

<210> SEQ ID NO 33
<211> LENGTH: 110
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) VL

<400> SEQUENCE: 33

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Trp Val Phe Gly Gly Gly Thr Lys Leu Thr Val Leu Ser Ser
            100                 105                 110

<210> SEQ ID NO 34
<211> LENGTH: 7
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) HVR-L1

<400> SEQUENCE: 34

Asn Asn Ile Gly Ser Lys Ser
1               5

<210> SEQ ID NO 35
<211> LENGTH: 3
<212> TYPE: PRT
<213> ORGANISM: Artificial sequence
<220> FEATURE:
<223> OTHER INFORMATION: Ang2 LC10 wt + G114A, S360P, T28N, T30A (HC) +
      D50T (LC) HVR-L2

<400> SEQUENCE: 35

Asp Thr Ser
1

<210> SEQ ID NO 36
<211> LENGTH: 8
<212> TYPE: PRT
<213> ORGANISM: Artificial sequence
<220> FEATURE:

<223> OTHER INFORMATION: Ang2 LC10 wt + G114A, S360P, T28N, T30A (HC) +
      D50T (LC) HVR-L3

<400> SEQUENCE: 36

Trp Asp Ser Ser Ser Asp His Trp
1               5

<210> SEQ ID NO 37
<211> LENGTH: 129
<212> TYPE: PRT
<213> ORGANISM: Artificial sequence
<220> FEATURE:
<223> OTHER INFORMATION: Ang2 LC10 wt + G114A, S360P, T28N, T30A, D106S
      (HC) + D50T (in LC) VH

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Ser Ser Pro Gly Tyr Tyr Tyr
            100                 105                 110

Pro Ala Ala Phe Asp Ile Trp Gly Gln Gly Thr Met Val Thr Val Ser
        115                 120                 125

Ser

<210> SEQ ID NO 38
<211> LENGTH: 7
<212> TYPE: PRT
<213> ORGANISM: Artificial sequence
<220> FEATURE:
<223> OTHER INFORMATION: Ang2 LC10 wt + G114A, S360P, T28N, T30A, D106S
      (HC) + D50T (in LC) HVR-H1

<400> SEQUENCE: 38

Gly Tyr Asn Phe Ala Gly Tyr
1               5

<210> SEQ ID NO 39
<211> LENGTH: 3
<212> TYPE: PRT
<213> ORGANISM: Artificial sequence
<220> FEATURE:
<223> OTHER INFORMATION: Ang2 LC10 wt + G114A, S360P, T28N, T30A, D106S
      (HC) + D50T (in LC) HVR-H2s

<400> SEQUENCE: 39

Asn Ser Gly
1

<210> SEQ ID NO 40
<211> LENGTH: 17
<212> TYPE: PRT
<213> ORGANISM: Artificial sequence
<220> FEATURE:

<223> OTHER INFORMATION: Ang2 LC10 wt + G114A, S360P, T28N, T30A, D106S
      (HC) + D50T (in LC) HVR-H2

<400> SEQUENCE: 40

Trp Ile Asn Pro Asn Ser Gly Gly Thr Asn Tyr Ala Gln Lys Phe Gln
1               5                   10                  15

Gly

<210> SEQ ID NO 41
<211> LENGTH: 18
<212> TYPE: PRT
<213> ORGANISM: Artificial sequence
<220> FEATURE:
<223> OTHER INFORMATION: Ang2 LC10 wt + G114A, S360P, T28N, T30A, D106S
      (HC) + D50T (in LC) HVR-H3

<400> SEQUENCE: 41

Pro Asn Pro Tyr Tyr Tyr Ser Ser Pro Gly Tyr Tyr Tyr Pro Ala Ala
1               5                   10                  15

Phe Asp

<210> SEQ ID NO 42
<211> LENGTH: 110
<212> TYPE: PRT
<213> ORGANISM: Artificial sequence
<220> FEATURE:
<223> OTHER INFORMATION: Ang2 LC10 wt + G114A, S360P, T28N, T30A, D106S
      (HC) + D50T (in LC) VL

<400> SEQUENCE: 42

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser
            100                 105                 110

<210> SEQ ID NO 43
<211> LENGTH: 7
<212> TYPE: PRT
<213> ORGANISM: Artificial sequence
<220> FEATURE:
<223> OTHER INFORMATION: Ang2 LC10 wt + G114A, S360P, T28N, T30A, D106S
      (HC) + D50T (in LC) HVR-L1

<400> SEQUENCE: 43

Asn Asn Ile Gly Ser Lys Ser
1               5

<210> SEQ ID NO 44
<211> LENGTH: 3
<212> TYPE: PRT
<213> ORGANISM: Artificial sequence
<220> FEATURE:
<223> OTHER INFORMATION: Ang2 LC10 wt + G114A, S360P, T28N, T30A, D106S (HC) + D50T (in LC) HVR-L2

<400> SEQUENCE: 44

Asp Thr Ser
1

<210> SEQ ID NO 45
<211> LENGTH: 8
<212> TYPE: PRT
<213> ORGANISM: Artificial sequence
<220> FEATURE:
<223> OTHER INFORMATION: Ang2 LC10 wt + G114A, S360P, T28N, T30A, D106S
      (HC) + D50T (in LC) HVR-L3

<400> SEQUENCE: 45

Trp Asp Ser Ser Ser Asp His Trp
1               5

<210> SEQ ID NO 46
<211> LENGTH: 236
<212> TYPE: PRT
<213> ORGANISM: Artificial sequence
<220> FEATURE:
<223> OTHER INFORMATION: Ang2_wt VHVL cross LC kappa

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 47
<211> LENGTH: 236

<212> TYPE: PRT
<213> ORGANISM: Artificial sequence
<220> FEATURE:
<223> OTHER INFORMATION: Ang2-wt mut4 + D50T VHVL cross kappa LC

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Pro Gly Tyr Tyr Tyr
            100                 105                 110

Pro Ala Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 48
<211> LENGTH: 236
<212> TYPE: PRT
<213> ORGANISM: Artificial sequence
<220> FEATURE:
<223> OTHER INFORMATION: Ang2-mut4 + D50T + D106S VHVL cross kappa LC

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

```
Ala Arg Ser Pro Asn Pro Tyr Tyr Ser Ser Pro Gly Tyr Tyr
            100                 105                 110

Pro Ala Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 49
<211> LENGTH: 213
<212> TYPE: PRT
<213> ORGANISM: Artificial sequence
<220> FEATURE:
<223> OTHER INFORMATION: Ang2_wt CHCk cross LC kappa

<400> SEQUENCE: 49

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210
```

<210> SEQ ID NO 50
<211> LENGTH: 213
<212> TYPE: PRT
<213> ORGANISM: Artificial sequence
<220> FEATURE:
<223> OTHER INFORMATION: Ang2-wt mut4 + D50T CHCk cross LC

<400> SEQUENCE: 50

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210

<210> SEQ ID NO 51
<211> LENGTH: 461
<212> TYPE: PRT
<213> ORGANISM: Artificial sequence
<220> FEATURE:
<223> OTHER INFORMATION: Xang2-0098 Ang2 LC 10 VH wt IgG1

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys

```
                    85                  90                  95
Ala Arg Ser Pro Asn Pro Tyr Tyr Asp Ser Ser Gly Tyr Tyr Tyr
                100                 105                 110

Pro Gly Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Asp Glu Leu Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro
    450                 455                 460

<210> SEQ ID NO 52
<211> LENGTH: 461
<212> TYPE: PRT
<213> ORGANISM: Artificial sequence
<220> FEATURE:
<223> OTHER INFORMATION: Xang2-0099Ang2 LC10 wt + G114A, S360P, T28N,
      T30A (HC)
```

<400> SEQUENCE: 52

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Pro Gly Tyr Tyr Tyr
            100                 105                 110

Pro Ala Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Asp Glu Leu Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
```

-continued

```
                405                 410                 415
Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro
    450                 455                 460

<210> SEQ ID NO 53
<211> LENGTH: 461
<212> TYPE: PRT
<213> ORGANISM: Artificial sequence
<220> FEATURE:
<223> OTHER INFORMATION: Xang2-0101

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Glu Ser Pro Gly Tyr Tyr Tyr
            100                 105                 110

Pro Ala Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
```

```
                305                 310                 315                 320
Val Leu Thr Val Leu His Gln Asp Trp Leu Asn Gly Lys Glu Tyr Lys
                    325                 330                 335

Cys Lys Val Ser Asn Lys Ala Leu Pro Ala Pro Ile Glu Lys Thr Ile
                340                 345                 350

Ser Lys Ala Lys Gly Gln Pro Arg Glu Pro Gln Val Tyr Thr Leu Pro
                355                 360                 365

Pro Ser Arg Asp Glu Leu Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                    405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
                435                 440                 445

His Asn His Tyr Thr Gln Lys Ser Leu Ser Leu Ser Pro
    450                 455                 460

<210> SEQ ID NO 54
<211> LENGTH: 496
<212> TYPE: PRT
<213> ORGANISM: Homo sapiens

<400> SEQUENCE: 54

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
                20                  25                  30

Gln Tyr Gln Val Gln His Gly Ser Cys Ser Tyr Thr Phe Leu Leu Pro
            35                  40                  45

Glu Met Asp Asn Cys Arg Ser Ser Ser Ser Pro Tyr Val Ser Asn Ala
        50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
                100                 105                 110

Gln Gln Asn Ala Val Gln Asn Gln Thr Ala Val Met Ile Glu Ile Gly
            115                 120                 125

Thr Asn Leu Leu Asn Gln Thr Ala Glu Gln Thr Arg Lys Leu Thr Asp
        130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
                180                 185                 190

Lys Lys Val Leu Ala Met Glu Asp Lys His Ile Ile Gln Leu Gln Ser
            195                 200                 205

Ile Lys Glu Glu Lys Asp Gln Leu Gln Val Leu Val Ser Lys Gln Asn
        210                 215                 220
```

-continued

```
Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
            245                 250                 255

Asn Leu Leu Thr Met Met Ser Thr Ser Asn Ser Ala Lys Asp Pro Thr
        260                 265                 270

Val Ala Lys Glu Glu Gln Ile Ser Phe Arg Asp Cys Ala Glu Val Phe
    275                 280                 285

Lys Ser Gly His Thr Thr Asn Gly Ile Tyr Thr Leu Thr Phe Pro Asn
290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495
```

<210> SEQ ID NO 55
<211> LENGTH: 129
<212> TYPE: PRT
<213> ORGANISM: Artificial sequence
<220> FEATURE:
<223> OTHER INFORMATION: Ang2 LC10 wt + G114A, S360P, T28N, T30A, D106E (HC) VH

<400> SEQUENCE: 55

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg Ser Pro Asn Pro Tyr Tyr Glu Ser Pro Gly Tyr Tyr Tyr
            100                 105                 110

Pro Ala Ala Phe Asp Ile Trp Gly Gln Gly Thr Met Val Thr Val Ser
            115                 120                 125

Ser
```

<210> SEQ ID NO 56
<211> LENGTH: 18
<212> TYPE: PRT
<213> ORGANISM: Artificial sequence
<220> FEATURE:
<223> OTHER INFORMATION: ANg2 D106E HVR-H3

<400> SEQUENCE: 56

```
Pro Asn Pro Tyr Tyr Tyr Glu Ser Pro Gly Tyr Tyr Pro Ala Ala
1               5                   10                  15

Phe Asp
```

<210> SEQ ID NO 57
<211> LENGTH: 236
<212> TYPE: PRT
<213> ORGANISM: Artificial sequence
<220> FEATURE:
<223> OTHER INFORMATION: 0015 HC

<400> SEQUENCE: 57

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Pro Gly Tyr Tyr Tyr
            100                 105                 110

Pro Gly Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235
```

<210> SEQ ID NO 58
<211> LENGTH: 236
<212> TYPE: PRT
<213> ORGANISM: Artificial sequence
<220> FEATURE:
<223> OTHER INFORMATION: 0016 HC

<400> SEQUENCE: 58

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Pro Gly Thr Tyr Tyr
                100                 105                 110

Pro Gly Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 59
<211> LENGTH: 236
<212> TYPE: PRT
<213> ORGANISM: Artificial sequence
<220> FEATURE:
<223> OTHER INFORMATION: 0017 HC

<400> SEQUENCE: 59

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Cys Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80
```

```
Met Glu Leu Ser Arg Leu Arg Ser Asp Asp Thr Ala Val Tyr Tyr Cys
                85                  90                  95

Ala Arg Ser Pro Asn Pro Tyr Tyr Cys Ser Ser Gly Tyr Tyr Tyr
            100                 105                 110

Pro Gly Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 60
<211> LENGTH: 236
<212> TYPE: PRT
<213> ORGANISM: Artificial sequence
<220> FEATURE:
<223> OTHER INFORMATION: 0021 HC

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Ser Gly Tyr Tyr Tyr
            100                 105                 110

Pro Ala Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205
```

```
Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 61
<211> LENGTH: 236
<212> TYPE: PRT
<213> ORGANISM: Artificial sequence
<220> FEATURE:
<223> OTHER INFORMATION: 0025 HC

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Val Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Ser Gly Tyr Tyr Tyr
                100                 105                 110

Pro Gly Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 62
<211> LENGTH: 236
<212> TYPE: PRT
<213> ORGANISM: Artificial sequence
<220> FEATURE:
<223> OTHER INFORMATION: 0026 HC

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
                20                  25                  30

Tyr Met His Trp Val Arg Gln Ala Pro Gly Gln Gly Leu Glu Trp Met
```

```
            35                  40                  45
Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Pro Asn Pro Tyr Tyr Tyr Asp Ser Ser Gly Tyr Tyr Tyr
                100                 105                 110

Pro Gly Ala Phe Asp Ile Trp Gly Gln Gly Thr Met Val Thr Val Ser
                115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 63
<211> LENGTH: 236
<212> TYPE: PRT
<213> ORGANISM: Artificial sequence
<220> FEATURE:
<223> OTHER INFORMATION: 0027 HC

<400> SEQUENCE: 63

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Asn Phe Lys Gly Tyr
                 20                  25                  30

Tyr Met His Trp Val Arg Gln Ala Pro Gly Gln Gly Leu Glu Trp Met
             35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Pro Asn Pro Tyr Tyr Tyr Asp Ser Ser Gly Tyr Tyr Tyr
                100                 105                 110

Pro Gly Ala Phe Asp Ile Trp Gly Gln Gly Thr Met Val Thr Val Ser
                115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
```

165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 64
<211> LENGTH: 236
<212> TYPE: PRT
<213> ORGANISM: Artificial sequence
<220> FEATURE:
<223> OTHER INFORMATION: 0028 HC

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Lys Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 65
<211> LENGTH: 236
<212> TYPE: PRT
<213> ORGANISM: Artificial sequence
<220> FEATURE:
<223> OTHER INFORMATION: 0029 HC

<400> SEQUENCE: 65

-continued

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Pro Gly Tyr Tyr Tyr
            100                 105                 110

Pro Ala Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 66
<211> LENGTH: 213
<212> TYPE: PRT
<213> ORGANISM: Artificial sequence
<220> FEATURE:
<223> OTHER INFORMATION: 0031 HC

<400> SEQUENCE: 66

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Trp
        35                  40                  45

Asp Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
            115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
            195                 200                 205

Glu Pro Lys Ser Cys
    210

<210> SEQ ID NO 67
<211> LENGTH: 213
<212> TYPE: PRT
<213> ORGANISM: Artificial sequence
<220> FEATURE:
<223> OTHER INFORMATION: 0032 HC

<400> SEQUENCE: 67

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Ser Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
            195                 200                 205

Glu Pro Lys Ser Cys
    210

<210> SEQ ID NO 68
<211> LENGTH: 236
<212> TYPE: PRT
<213> ORGANISM: Artificial sequence
<220> FEATURE:
<223> OTHER INFORMATION: 0033 HC

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Ser Pro Asn Pro Tyr Tyr Tyr Asp Ser Pro Gly Tyr Tyr Tyr
            100                 105                 110

Pro Ala Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Cys
225                 230                 235

<210> SEQ ID NO 69
<211> LENGTH: 236
<212> TYPE: PRT
<213> ORGANISM: Artificial sequence
<220> FEATURE:
<223> OTHER INFORMATION: 0039 HC

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Ser Pro Asn Pro Tyr Tyr Tyr Thr Ser Ser Gly Tyr Tyr Tyr
            100                 105                 110

Pro Gly Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 70
<211> LENGTH: 236
<212> TYPE: PRT
<213> ORGANISM: Artificial sequence
<220> FEATURE:
<223> OTHER INFORMATION: 0040 HC

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Val Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Pro Gly Tyr Tyr Tyr
                100                 105                 110

Pro Ala Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 71

<211> LENGTH: 236
<212> TYPE: PRT
<213> ORGANISM: Artificial sequence
<220> FEATURE:
<223> OTHER INFORMATION: 0042 HC

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Lys Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Pro Gly Tyr Tyr Tyr
            100                 105                 110

Pro Ala Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 72
<211> LENGTH: 236
<212> TYPE: PRT
<213> ORGANISM: Artificial sequence
<220> FEATURE:
<223> OTHER INFORMATION: 0057 HC

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys

```
            85                  90                  95
Ala Arg Ser Pro Asn Pro Tyr Tyr Tyr Glu Ser Pro Gly Tyr Tyr Tyr
            100                 105                 110

Pro Ala Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 73
<211> LENGTH: 236
<212> TYPE: PRT
<213> ORGANISM: Artificial sequence
<220> FEATURE:
<223> OTHER INFORMATION: 0058 HC

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Thr Ser Pro Gly Tyr Tyr Tyr
            100                 105                 110

Pro Ala Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
```

Ser Pro Val Thr Lys Ser Phe Asn Arg Gly Glu Cys
225                 230                 235

<210> SEQ ID NO 74
<211> LENGTH: 236
<212> TYPE: PRT
<213> ORGANISM: Artificial sequence
<220> FEATURE:
<223> OTHER INFORMATION: 0076 HC

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Ser Ser Gly Tyr Tyr Tyr
                100                 105                 110

Pro Gly Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
    195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 75
<211> LENGTH: 459
<212> TYPE: PRT
<213> ORGANISM: Artificial sequence
<220> FEATURE:
<223> OTHER INFORMATION: ANG2 ref HC

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

```
Gly Trp Ile Asn Pro Asn Ser Gly Gly Thr Asn Tyr Ala Gln Lys Phe
     50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
                 85                  90                  95
Ala Arg Ser Pro Asn Pro Tyr Tyr Asp Ser Ser Gly Tyr Tyr Tyr
                100                 105                 110
Pro Gly Ala Phe Asp Ile Trp Gly Gln Gly Thr Met Val Thr Val Ser
            115                 120                 125
Ser Ala Ser Thr Lys Gly Pro Ser Val Phe Pro Leu Ala Pro Ser Ser
130                 135                 140
Lys Ser Thr Ser Gly Gly Thr Ala Ala Leu Gly Cys Leu Val Lys Asp
145                 150                 155                 160
Tyr Phe Pro Glu Pro Val Thr Val Ser Trp Asn Ser Gly Ala Leu Thr
                165                 170                 175
Ser Gly Val His Thr Phe Pro Ala Val Leu Gln Ser Ser Gly Leu Tyr
            180                 185                 190
Ser Leu Ser Ser Val Val Thr Val Pro Ser Ser Ser Leu Gly Thr Gln
            195                 200                 205
Thr Tyr Ile Cys Asn Val Asn His Lys Pro Ser Asn Thr Lys Val Asp
    210                 215                 220
Lys Lys Val Glu Pro Lys Ser Cys Asp Lys Thr His Thr Cys Pro Pro
225                 230                 235                 240
Cys Pro Ala Pro Glu Leu Leu Gly Gly Pro Ser Val Phe Leu Phe Pro
                245                 250                 255
Pro Lys Pro Lys Asp Thr Leu Met Ile Ser Arg Thr Pro Glu Val Thr
            260                 265                 270
Cys Val Val Val Asp Val Ser His Glu Asp Pro Glu Val Lys Phe Asn
            275                 280                 285
Trp Tyr Val Asp Gly Val Glu Val His Asn Ala Lys Thr Lys Pro Arg
    290                 295                 300
Glu Glu Gln Tyr Asn Ser Thr Tyr Arg Val Val Ser Val Leu Thr Val
305                 310                 315                 320
Leu His Gln Asp Trp Leu Asn Gly Lys Glu Tyr Lys Cys Lys Val Ser
                325                 330                 335
Asn Lys Ala Leu Pro Ala Pro Ile Glu Lys Thr Ile Ser Lys Ala Lys
            340                 345                 350
Gly Gln Pro Arg Glu Pro Gln Val Tyr Thr Leu Pro Pro Ser Arg Asp
            355                 360                 365
Glu Leu Thr Lys Asn Gln Val Ser Leu Thr Cys Leu Val Lys Gly Phe
370                 375                 380
Tyr Pro Ser Asp Ile Ala Val Glu Trp Glu Ser Asn Gly Gln Pro Glu
385                 390                 395                 400
Asn Asn Tyr Lys Thr Thr Pro Pro Val Leu Asp Ser Asp Gly Ser Phe
                405                 410                 415
Phe Leu Tyr Ser Lys Leu Thr Val Asp Lys Ser Arg Trp Gln Gln Gly
            420                 425                 430
Asn Val Phe Ser Cys Ser Val Met His Glu Ala Leu His Asn His Tyr
            435                 440                 445
Thr Gln Lys Ser Leu Ser Leu Ser Pro Gly Lys
    450                 455
```

-continued

<210> SEQ ID NO 76
<211> LENGTH: 217
<212> TYPE: PRT
<213> ORGANISM: Artificial sequence
<220> FEATURE:
<223> OTHER INFORMATION: ANG2 ref LC

<400> SEQUENCE: 76

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 77
<211> LENGTH: 213
<212> TYPE: PRT
<213> ORGANISM: Artificial Sequence
<220> FEATURE:
<223> OTHER INFORMATION: 0154 LC

<400> SEQUENCE: 77

```
Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95
```

```
Tyr Val Phe Gly Thr Gly Thr Lys Val Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210

<210> SEQ ID NO 78
<211> LENGTH: 213
<212> TYPE: PRT
<213> ORGANISM: Artificial Sequence
<220> FEATURE:
<223> OTHER INFORMATION: 0155 LC

<400> SEQUENCE: 78

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210

<210> SEQ ID NO 79
<211> LENGTH: 453
```

```
<212> TYPE: PRT
<213> ORGANISM: Artificial Sequence
<220> FEATURE:
<223> OTHER INFORMATION: VEGF ref1 HC

<400> SEQUENCE: 79
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 |
| Ser | Leu | Arg | Leu | Ser | Cys | Ala | Ala | Ser | Gly | Tyr | Thr | Phe | Thr | Asn | Tyr |
| | | | 20 | | | | | 25 | | | | | 30 | |
| Gly | Met | Asn | Trp | Val | Arg | Gln | Ala | Pro | Gly | Lys | Gly | Leu | Glu | Trp | Val |
| | | 35 | | | | | 40 | | | | | 45 | | |
| Gly | Trp | Ile | Asn | Thr | Tyr | Thr | Gly | Glu | Pro | Thr | Tyr | Ala | Ala | Asp | Phe |
| 50 | | | | | 55 | | | | | 60 | | | | | |
| Lys | Arg | Arg | Phe | Thr | Phe | Ser | Leu | Asp | Thr | Ser | Lys | Ser | Thr | Ala | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Tyr | Pro | His | Tyr | Tyr | Gly | Ser | Ser | His | Trp | Tyr | Phe | Asp | Val |
| | | | 100 | | | | | 105 | | | | | 110 | | |
| Trp | Gly | Gln | Gly | Thr | Leu | Val | Thr | Val | Ser | Ser | Ala | Ser | Thr | Lys | Gly |
| | | | 115 | | | | | 120 | | | | | 125 | | |
| Pro | Ser | Val | Phe | Pro | Leu | Ala | Pro | Ser | Ser | Lys | Ser | Thr | Ser | Gly | Gly |
| 130 | | | | | 135 | | | | | 140 | | | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Ser | Leu | Gly | Thr | Gln | Thr | Tyr | Ile | Cys | Asn | Val |
| | | | 195 | | | | | 200 | | | | | 205 | | |
| Asn | His | Lys | Pro | Ser | Asn | Thr | Lys | Val | Asp | Lys | Lys | Val | Glu | Pro | Lys |
| | | 210 | | | | | 215 | | | | | 220 | | | |
| Ser | Cys | Asp | Lys | Thr | His | Thr | Cys | Pro | Pro | Cys | Pro | Ala | Pro | Glu | Leu |
| 225 | | | | | 230 | | | | | 235 | | | | | 240 |
| Leu | Gly | Gly | Pro | Ser | Val | Phe | Leu | Phe | Pro | Pro | Lys | Pro | Lys | Asp | Thr |
| | | | | 245 | | | | | 250 | | | | | 255 | |
| Leu | Met | Ile | Ser | Arg | Thr | Pro | Glu | Val | Thr | Cys | Val | Val | Val | Asp | Val |
| | | | 260 | | | | | 265 | | | | | 270 | | |
| Ser | His | Glu | Asp | Pro | Glu | Val | Lys | Phe | Asn | Trp | Tyr | Val | Asp | Gly | Val |
| | | 275 | | | | | 280 | | | | | 285 | | | |
| Glu | Val | His | Asn | Ala | Lys | Thr | Lys | Pro | Arg | Glu | Glu | Gln | Tyr | Asn | Ser |
| | 290 | | | | | 295 | | | | | 300 | | | | |
| Thr | Tyr | Arg | Val | Val | Ser | Val | Leu | Thr | Val | Leu | His | Gln | Asp | Trp | Leu |
| 305 | | | | | 310 | | | | | 315 | | | | | 320 |
| Asn | Gly | Lys | Glu | Tyr | Lys | Cys | Lys | Val | Ser | Asn | Lys | Ala | Leu | Pro | Ala |
| | | | | 325 | | | | | 330 | | | | | 335 | |
| Pro | Ile | Glu | Lys | Thr | Ile | Ser | Lys | Ala | Lys | Gly | Gln | Pro | Arg | Glu | Pro |
| | | | 340 | | | | | 345 | | | | | 350 | | |
| Gln | Val | Tyr | Thr | Leu | Pro | Pro | Cys | Arg | Asp | Glu | Leu | Thr | Lys | Asn | Gln |
| | | | 355 | | | | | 360 | | | | | 365 | | |
| Val | Ser | Leu | Trp | Cys | Leu | Val | Lys | Gly | Phe | Tyr | Pro | Ser | Asp | Ile | Ala |
| | | 370 | | | | | 375 | | | | | 380 | | | |

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Lys
    450

<210> SEQ ID NO 80
<211> LENGTH: 214
<212> TYPE: PRT
<213> ORGANISM: Artificial Sequence
<220> FEATURE:
<223> OTHER INFORMATION: VEGF ref1 LC

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 81
<211> LENGTH: 463
<212> TYPE: PRT
<213> ORGANISM: Artificial Sequence
<220> FEATURE:
<223> OTHER INFORMATION: ANG2 ref1 HC

<400> SEQUENCE: 81

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Gly Tyr
         20                  25                  30
Tyr Met His Trp Val Arg Gln Ala Pro Gly Gln Gly Leu Glu Trp Met
         35                  40                  45
Gly Trp Ile Asn Pro Asn Ser Gly Gly Thr Asn Tyr Ala Gln Lys Phe
 50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
             85                  90                  95
Ala Arg Ser Pro Asn Pro Tyr Tyr Tyr Asp Ser Ser Gly Tyr Tyr Tyr
                100                 105                 110
Pro Gly Ala Phe Asp Ile Trp Gly Gln Gly Thr Met Val Thr Val Ser
            115                 120                 125
Ser Ala Ser Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys Asp Lys Thr His
225                 230                 235                 240
Thr Cys Pro Pro Cys Pro Ala Pro Glu Leu Leu Gly Gly Pro Ser Val
                245                 250                 255
Phe Leu Phe Pro Pro Lys Pro Lys Asp Thr Leu Met Ile Ser Arg Thr
            260                 265                 270
Pro Glu Val Thr Cys Val Val Val Asp Val Ser His Glu Asp Pro Glu
        275                 280                 285
Val Lys Phe Asn Trp Tyr Val Asp Gly Val Glu Val His Asn Ala Lys
    290                 295                 300
Thr Lys Pro Arg Glu Glu Gln Tyr Asn Ser Thr Tyr Arg Val Val Ser
305                 310                 315                 320
Val Leu Thr Val Leu His Gln Asp Trp Leu Asn Gly Lys Glu Tyr Lys
                325                 330                 335
Cys Lys Val Ser Asn Lys Ala Leu Pro Ala Pro Ile Glu Lys Thr Ile
            340                 345                 350
Ser Lys Ala Lys Gly Gln Pro Arg Glu Pro Gln Val Cys Thr Leu Pro
        355                 360                 365
Pro Ser Arg Asp Glu Leu Thr Lys Asn Gln Val Ser Leu Ser Cys Ala
    370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Val Leu Asp Ser
                405                 410                 415
Asp Gly Ser Phe Phe Leu Val Ser Lys Leu Thr Val Asp Lys Ser Arg
            420                 425                 430
```

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
    450                 455                 460

<210> SEQ ID NO 82
<211> LENGTH: 213
<212> TYPE: PRT
<213> ORGANISM: Artificial Sequence
<220> FEATURE:
<223> OTHER INFORMATION: ANG2 ref1 LC

<400> SEQUENCE: 82

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210

<210> SEQ ID NO 83
<211> LENGTH: 463
<212> TYPE: PRT
<213> ORGANISM: Artificial Sequence
<220> FEATURE:
<223> OTHER INFORMATION: 0163 ANG2 HC

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

```
Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Pro Asn Pro Tyr Tyr Tyr Asp Ser Pro Gly Tyr Tyr Tyr
            100                 105                 110

Pro Ala Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Cys Thr Leu Pro
        355                 360                 365

Pro Ser Arg Asp Glu Leu Thr Lys Asn Gln Val Ser Leu Ser Cys Ala
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
450                 455                 460
```

<210> SEQ ID NO 84
<211> LENGTH: 213

```
<212> TYPE: PRT
<213> ORGANISM: Artificial Sequence
<220> FEATURE:
<223> OTHER INFORMATION: 0163 ANG2 LC

<400> SEQUENCE: 84

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210

<210> SEQ ID NO 85
<211> LENGTH: 463
<212> TYPE: PRT
<213> ORGANISM: Artificial Sequence
<220> FEATURE:
<223> OTHER INFORMATION: 0164 ANG2 HC

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Ser Ser Pro Gly Tyr Tyr Tyr
            100                 105                 110
```

```
Pro Ala Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
    195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
            245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
            275                 280                 285

Val Lys Phe Asn Trp Tyr Val Asp Gly Val Glu Val His Asn Ala Lys
            290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Cys Thr Leu Pro
    355                 360                 365

Pro Ser Arg Asp Glu Leu Thr Lys Asn Gln Val Ser Leu Ser Cys Ala
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
    435                 440                 445

His Asn His Tyr Thr Gln Lys Ser Leu Ser Leu Ser Pro Gly Lys
450                 455                 460

<210> SEQ ID NO 86
<211> LENGTH: 213
<212> TYPE: PRT
<213> ORGANISM: Artificial Sequence
<220> FEATURE:
<223> OTHER INFORMATION: 0164 ANG2 LC

<400> SEQUENCE: 86

Gln Pro Gly Leu Thr Gln Pro Pro Ser Val Ser Val Ala Pro Gly Gln
1               5                   10                  15
```

```
Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Thr Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                85                  90                  95

Tyr Val Phe Gly Thr Gly Thr Lys Val Thr Val Leu Ser Ser Ala Ser
                100                 105                 110

Thr Lys Gly Pro Ser Val Phe Pro Leu Ala Pro Ser Ser Lys Ser Thr
            115                 120                 125

Ser Gly Gly Thr Ala Ala Leu Gly Cys Leu Val Lys Asp Tyr Phe Pro
130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
                180                 185                 190

Cys Asn Val Asn His Lys Pro Ser Asn Thr Lys Val Asp Lys Lys Val
                195                 200                 205

Glu Pro Lys Ser Cys
        210

<210> SEQ ID NO 87
<211> LENGTH: 453
<212> TYPE: PRT
<213> ORGANISM: Artificial Sequence
<220> FEATURE:
<223> OTHER INFORMATION: VEGF ref2 HC

<400> SEQUENCE: 87

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Ala
225                 230                 235                 240
Ala Gly Gly Pro Ser Val Phe Leu Phe Pro Pro Lys Pro Lys Asp Thr
                245                 250                 255
Leu Met Ala Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Gly Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Cys Arg Asp Glu Leu Thr Lys Asn Gln
        355                 360                 365
Val Ser Leu Trp Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn Ala Tyr Thr Gln Lys Ser Leu Ser
        435                 440                 445
Leu Ser Pro Gly Lys
    450

<210> SEQ ID NO 88
<211> LENGTH: 214
<212> TYPE: PRT
<213> ORGANISM: Artificial Sequence
<220> FEATURE:
<223> OTHER INFORMATION: VEGF ref2 LC

<400> SEQUENCE: 88

Asp Ile Gln Leu Thr Gln Ser Pro Ser Ser Leu Ser Ala Ser Val Gly
1               5                   10                  15
Asp Arg Val Thr Ile Thr Cys Ser Ala Ser Gln Asp Ile Ser Asn Tyr
            20                  25                  30
Leu Asn Trp Tyr Gln Gln Lys Pro Gly Lys Ala Pro Lys Val Leu Ile
        35                  40                  45
Tyr Phe Thr Ser Ser Leu His Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 89
<211> LENGTH: 463
<212> TYPE: PRT
<213> ORGANISM: Artificial Sequence
<220> FEATURE:
<223> OTHER INFORMATION: 0165 ANG2 HC

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Pro Gly Tyr Tyr Tyr
            100                 105                 110

Pro Ala Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

```
Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ala Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
                325                 330                 335

Cys Lys Val Ser Asn Lys Ala Leu Gly Ala Pro Ile Glu Lys Thr Ile
            340                 345                 350

Ser Lys Ala Lys Gly Gln Pro Arg Glu Pro Gln Val Cys Thr Leu Pro
        355                 360                 365

Pro Ser Arg Asp Glu Leu Thr Lys Asn Gln Val Ser Leu Ser Cys Ala
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn Ala Tyr Thr Gln Lys Ser Leu Ser Leu Ser Pro Gly Lys
    450                 455                 460

<210> SEQ ID NO 90
<211> LENGTH: 213
<212> TYPE: PRT
<213> ORGANISM: Artificial Sequence
<220> FEATURE:
<223> OTHER INFORMATION: 0165 ANG2 LC

<400> SEQUENCE: 90

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110
```

```
Thr Lys Gly Pro Ser Val Phe Pro Leu Ala Pro Ser Ser Lys Ser Thr
            115                 120                 125

Ser Gly Gly Thr Ala Ala Leu Gly Cys Leu Val Lys Asp Tyr Phe Pro
        130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
            195                 200                 205

Glu Pro Lys Ser Cys
    210
```

<210> SEQ ID NO 91
<211> LENGTH: 463
<212> TYPE: PRT
<213> ORGANISM: Artificial Sequence
<220> FEATURE:
<223> OTHER INFORMATION: 0166 ANG2 HC

<400> SEQUENCE: 91

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Ser Ser Pro Gly Tyr Tyr Tyr
            100                 105                 110

Pro Ala Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Ala Ala Gly Gly Pro Ser Val
                245                 250                 255
```

```
Phe Leu Phe Pro Pro Lys Pro Lys Asp Thr Leu Met Ala Ser Arg Thr
            260                 265                 270

Pro Glu Val Thr Cys Val Val Val Asp Val Ser His Glu Asp Pro Glu
275                 280                 285

Val Lys Phe Asn Trp Tyr Val Asp Gly Val Glu Val His Asn Ala Lys
        290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
                325                 330                 335

Cys Lys Val Ser Asn Lys Ala Leu Gly Ala Pro Ile Glu Lys Thr Ile
            340                 345                 350

Ser Lys Ala Lys Gly Gln Pro Arg Glu Pro Gln Val Cys Thr Leu Pro
        355                 360                 365

Pro Ser Arg Asp Glu Leu Thr Lys Asn Gln Val Ser Leu Ser Cys Ala
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn Ala Tyr Thr Gln Lys Ser Leu Ser Leu Ser Pro Gly Lys
    450                 455                 460

<210> SEQ ID NO 92
<211> LENGTH: 213
<212> TYPE: PRT
<213> ORGANISM: Artificial Sequence
<220> FEATURE:
<223> OTHER INFORMATION: 0166 ANG2 LC

<400> SEQUENCE: 92

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160
```

```
His Thr Phe Pro Ala Val Leu Gln Ser Ser Gly Leu Tyr Ser Leu Ser
                165                 170                 175

Ser Val Val Thr Val Pro Ser Ser Leu Gly Thr Gln Thr Tyr Ile
            180                 185                 190

Cys Asn Val Asn His Lys Pro Ser Asn Thr Lys Val Asp Lys Lys Val
            195                 200                 205

Glu Pro Lys Ser Cys
    210
```

<210> SEQ ID NO 93
<211> LENGTH: 463
<212> TYPE: PRT
<213> ORGANISM: Artificial Sequence
<220> FEATURE:
<223> OTHER INFORMATION: ANG2 ref2 HC

<400> SEQUENCE: 93

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ala Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300
```

-continued

```
Thr Lys Pro Arg Glu Glu Gln Tyr Asn Ser Tyr Arg Val Val Ser
305                 310                 315                 320

Val Leu Thr Val Leu Ala Gln Asp Trp Leu Asn Gly Lys Glu Tyr Lys
                325                 330                 335

Cys Lys Val Ser Asn Lys Ala Leu Gly Ala Pro Ile Glu Lys Thr Ile
                340                 345                 350

Ser Lys Ala Lys Gly Gln Pro Arg Glu Pro Gln Val Cys Thr Leu Pro
                355                 360                 365

Pro Ser Arg Asp Glu Leu Thr Lys Asn Gln Val Ser Leu Ser Cys Ala
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
                420                 425                 430

Trp Gln Gln Gly Asn Val Phe Ser Cys Ser Val Met His Glu Ala Leu
                435                 440                 445

His Asn Ala Tyr Thr Gln Lys Ser Leu Ser Leu Ser Pro Gly Lys
    450                 455                 460

<210> SEQ ID NO 94
<211> LENGTH: 213
<212> TYPE: PRT
<213> ORGANISM: Artificial Sequence
<220> FEATURE:
<223> OTHER INFORMATION: ANG2 ref2 LC

<400> SEQUENCE: 94

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
                100                 105                 110

Thr Lys Gly Pro Ser Val Phe Pro Leu Ala Pro Ser Ser Lys Ser Thr
            115                 120                 125

Ser Gly Gly Thr Ala Ala Leu Gly Cys Leu Val Lys Asp Tyr Phe Pro
        130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175
```

```
Ser Val Val Thr Val Pro Ser Ser Ser Leu Gly Thr Gln Thr Tyr Ile
            180             185                 190

Cys Asn Val Asn His Lys Pro Ser Asn Thr Lys Val Asp Lys Lys Val
            195             200             205

Glu Pro Lys Ser Cys
    210
```